(12) United States Patent
Wolfe et al.

(10) Patent No.: US 9,340,584 B2
(45) Date of Patent: May 17, 2016

(54) ENGINEERED THIOREDOXIN-LIKE FOLD PROTEINS

(75) Inventors: Jia Liu Wolfe, Winchester, MA (US); Glen S. Cho, Newton, MA (US); Brian Seed, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 64 days.

(21) Appl. No.: 14/006,237

(22) PCT Filed: Mar. 29, 2012

(86) PCT No.: PCT/US2012/031212
§ 371 (c)(1),
(2), (4) Date: Jan. 2, 2014

(87) PCT Pub. No.: WO2012/135500
PCT Pub. Date: Oct. 4, 2012

(65) Prior Publication Data
US 2014/0113832 A1    Apr. 24, 2014

Related U.S. Application Data

(60) Provisional application No. 61/468,836, filed on Mar. 29, 2011.

(51) Int. Cl.
| | | |
|---|---|---|
| *C07K 14/01* | (2006.01) | |
| *C12N 15/10* | (2006.01) | |
| *G01N 33/68* | (2006.01) | |
| *G01N 33/53* | (2006.01) | |
| *C07K 14/00* | (2006.01) | |

(52) U.S. Cl.
CPC .......... *C07K 14/001* (2013.01); *C12N 15/1044* (2013.01); *G01N 33/68* (2013.01); *C07K 2319/35* (2013.01); *G01N 33/53* (2013.01)

(58) Field of Classification Search
None
See application file for complete search history.

(56) References Cited

U.S. PATENT DOCUMENTS

| | | | |
|---|---|---|---|
| 5,858,714 A | 1/1999 | Hillman et al. | |
| 5,968,737 A | 10/1999 | Ali-Osman et al. | |
| 6,143,524 A * | 11/2000 | McCoy et al. | 435/69.7 |
| 6,171,816 B1 | 1/2001 | Yu et al. | |
| 6,444,425 B1 | 9/2002 | Reed et al. | |
| 6,461,822 B2 | 10/2002 | Gabel et al. | |
| 6,635,468 B2 | 10/2003 | Ashkenazi et al. | |
| 6,753,314 B1 | 6/2004 | Giot et al. | |
| 6,812,339 B1 | 11/2004 | Venter et al. | |
| 6,913,919 B2 | 7/2005 | Botstein et al. | |
| 6,916,648 B2 | 7/2005 | Goddard et al. | |
| 6,936,436 B2 | 8/2005 | Baker et al. | |
| 6,936,692 B2 | 8/2005 | Edwards et al. | |
| 6,943,241 B2 | 9/2005 | Isogai et al. | |
| 6,979,557 B2 | 12/2005 | Isogai et al. | |
| 6,984,519 B2 | 1/2006 | Desnoyers et al. | |
| 6,994,857 B2 | 2/2006 | Rosen et al. | |
| 7,060,479 B2 | 6/2006 | Edwards et al. | |
| 7,129,324 B2 | 10/2006 | Goddard et al. | |
| 7,129,338 B1 | 10/2006 | Ota et al. | |
| 7,189,817 B2 | 3/2007 | Goddard et al. | |
| 7,193,069 B2 | 3/2007 | Isogai et al. | |
| 7,345,142 B2 | 3/2008 | Cohen et al. | |
| 7,368,531 B2 | 5/2008 | Rosen et al. | |
| 7,411,051 B2 | 8/2008 | Rosen et al. | |
| 7,452,678 B2 | 11/2008 | Durham et al. | |
| 7,473,531 B1 | 1/2009 | Domon et al. | |
| 7,521,195 B1 | 4/2009 | Joseloff et al. | |
| 7,547,532 B2 | 6/2009 | Urade et al. | |
| 7,553,492 B2 | 6/2009 | Al-Mahmood et al. | |
| 7,560,233 B2 | 7/2009 | Volkert et al. | |
| 7,582,293 B2 | 9/2009 | Goddard et al. | |
| 7,601,505 B2 | 10/2009 | Monahan et al. | |
| 7,608,413 B1 | 10/2009 | Joseloff et al. | |
| 7,625,699 B2 | 12/2009 | Devlin et al. | |
| 7,638,238 B2 | 12/2009 | Kim et al. | |
| 7,638,288 B2 | 12/2009 | Van Rompaey et al. | |
| 7,691,599 B2 | 4/2010 | Rubin | |
| 2003/0113749 A1 | 6/2003 | Brent et al. | |
| 2006/0148057 A1* | 7/2006 | Min | C12N 9/0036 435/191 |

OTHER PUBLICATIONS

U.S. Appl. No. 61/468,836, Wolfe et al., filed Mar. 29, 2011.
Atkinson and Babbitt, "An Atlas of the Thioredoxin Fold Class Reveals the Complexity of Function-Enabling Enabling Adaptations," PloS Comput. Biol., Oct. 2009, 5(10):e1000541.
Bloom and Arnold, "In the light of directed evolution: Pathways of adaptive protein evolution," Proc. Natl. Acad. Sci., Jun. 2009, 106:9995-10000.
Brown et al., "Rational Design and Biophysical Characterization of Thioredoxin-Based Aptamers: Insights into Peptide Grafting," J. Mol. Biol., Jan. 2010, 395(4):871-883.
Cho et al., "Constructing High Complexity Synthetic Libraries of Long ORFs Using in Vitro Selection," J. Mol. Biol., 2000, 297(2):309-19.
Copley et al., "Divergence of function in the thioredoxin fold suprafamily: evidence for evolution of peroxiredoxins from a thioredoxin-like ancestor," Biochemistry, Nov. 2004, 43:13981-13995.

(Continued)

*Primary Examiner* — Suzanne M Noakes
*Assistant Examiner* — Jae W Lee
(74) *Attorney, Agent, or Firm* — Fish & Richardson P.C.

(57) ABSTRACT

The invention features compositions based on thioredoxin-like fold protein domains described as engineered thioredoxin-like fold proteins (ETRXs). These proteins include one or more artificially diversified thioredoxin-like fold protein domains; each domain may be originated from the same or different thioredoxin-like fold protein domains. Features of the invention also include methods for identifying and preparing an enriched composition of target binding, loop-diversified ETRXs with additional sequence variations to improve affinity, stability, selectivity, or solubility. The invention also features compositions of ETRXs substituted with prosthetic groups, polymers, proteins, nucleic acids, carbohydrates, metals, natural or synthetic small molecules and toxins.

7 Claims, 23 Drawing Sheets

(56) References Cited

OTHER PUBLICATIONS

Gebauer and Skerra, "Engineered protein scaffolds as next-generation antibody therapeutics," A. Curr. Opin. Chem. Biol., Jun. 2009, 3:245-255.

International Preliminary Report on Patentability in International Application No. PCT/US2012/031212, dated Oct. 1, 2013, 6 pages.

International Search Report and Written Opinion in International Application No. PCT/US2012/031212, dated Aug. 9, 2012, 8 pages.

Keefe et al., "One-Step Purification of Recombinant Proteins Using a Nanomolar-Affinity Streptavidin-Binding Peptide, the SBP-Tag," Protein Expr. Purif., 2001, (23):440-446.

Khersonsky et al., "Enzyme promiscuity: evolutionary and mechanistic aspects," Curr. Opin. Chem. Biol., 2006, 10:498-508.

Lillig and Holmgren, "Thioredoxin and related molecules—from biology to health and disease," Antioxid. Redox Signal., 2007, 9(1):25-47.

Loening et al., "Consensus guided mutagenesis of Renilla luciferase yields enhanced stability and light output," Protein Engineering, Design & Selection, Jul. 2006, 19(9):391-400.

Martin, "Thioredoxin—a fold for all reasons," Curr. Biol., Mar. 1995, 3:245-250.

Nakamura et al., "Thioredoxin 1 delivery as new therapeutics," Adv. Drug Deliv. Rev., Apr. 2009, 61(4):303-309.

Pan and Bardwell, "The origami of thioredoxin-like folds," Protein Sci., 2006, 15:2217-2227.

Pedone et al., "Multiple catalytically active thioredoxin folds: a winning strategy for many functions," Cell. Mol. Life Sci., Nov. 2010, 67(22):3797-814.

Qi and Grishin, "Structural Classification of Thioredoxin-Like Fold Proteins," Proteins, 2005, 58:376-388.

Tonikian et al., "Identifying specificity profiles for peptide recognition modules from phage-displayed peptide libraries," Nature protocols, 2007, (2):1368-1386.

Wilson et al., "The use of mRNA display to select high-affinity protein-binding peptides," Proc. Nat. Acad. Sci., Mar. 2001, (98):3750-3755.

Zahnd et al., "Efficient Tumor Targeting with High-Affinity Designed Ankyrin Repeat Proteins: Effects of Affinity and Molecular Size," Cancer Res., Feb. 2010, 70(4):1595-1605.

\* cited by examiner

Figure 1. Thioredoxin-like fold and its observed circular permutations.

Figure 3. Subfamilies of proteins of the Thioredoxin superfamily Pfam cd01659.
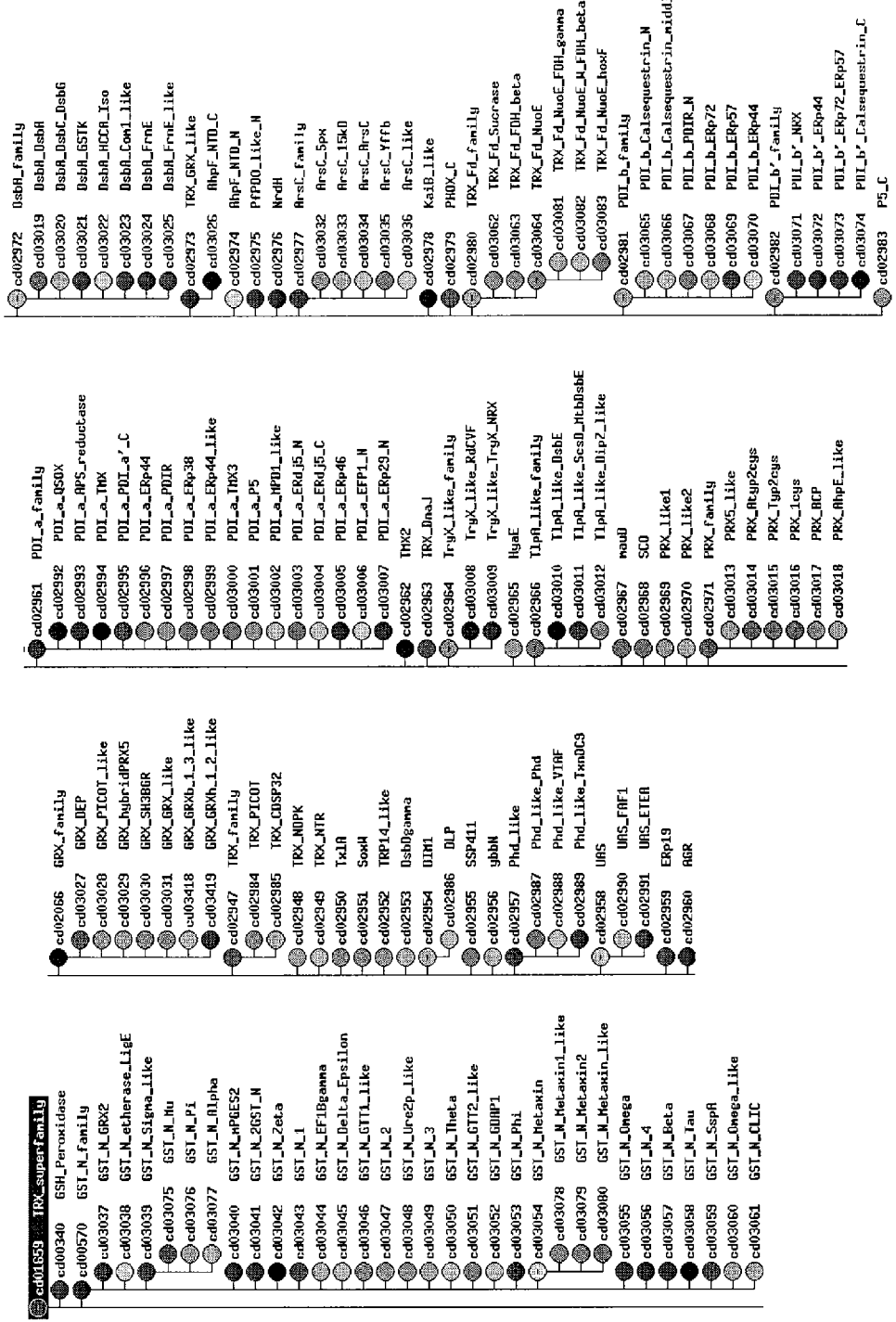

Figure 4. Listings of the Homo sapiens protein domains of the TRX superfamily. The underlined protein GI numbers correspond to protein domains associated with issued US patents.

Cd00340
GSH_Peroxidase
Homo sapiens(5)
- 121672
- 4467837
- 13124748
- 20810223
- 33516901

Cd02066
GRX_family
Homo sapiens(26)
- 1B4Q_A
- 6840947
- 6840947
- 28193244
- 1SJ6_A
- 1WRY_A
- 6010105
- 31418324
- 51464459
- 1JHB
- 5107031
- 37537704
- 37542493

Cd00570
GST_N_family
Homo sapiens(67)
- 1EEM_A
- 1GSE_B
- 1YJD
- 1XW5_B
- 3LJR_B
- 3PGT_B
- 1KON_A
- 1XWK_A
- 3GTU_D
- 5GSS_A
- 1K3Y_B
- 1TDI_A
- 1PW1_A
- 1LJR_B
- 1RK4_B
- 38257679
- 56203088
- 55961098
- 119165
- 38257738
- 52632405
- 57997510
- 56789715
- 2570009
- 55962678
- 20141285

Cd02947
TRX_family
Homo sapiens(7)
- 1AUC
- 1ERT
- 1GH2_A
- 6840947
- 20455529
- 33340051

Cd02948
TRX_NDPK
Homo sapiens(2)
- 31543836
- 47606157

Cd02952
TRP14_Like
Homo sapiens(1)
- 1WOU_A

Cd02954
DIM1
Homo sapiens(4)
- 1QGV_A
- 1PQN_A
- 51702156

Cd02955
SSP411
Homo sapiens(1)
- 31542723

Cd02957
PhD_like
Homo sapiens(10)
- 50401164
- 5430701
- 27808673
- 21706735
- 23503035

Cd02958
UAS
Homo sapiens(5)
- 20454906
- 24414114
- 3882309

Cd02959
ERp19
Homo sapiens(1)
- 1SEN_A

Cd02961 (30)
PDI_a_family
Homo sapiens(56)
- 1MEK
- 29839560
- 2507460
- 24308127
- 24308127
- 31077035
- 47117631
- 2501205
- 54633317
- 38505222
- 20521894
- 119530
- 1208427
- 30842594
- 1203965
- 30173124
- 54633317
- 28372543
- 1208427
- 119530
- 2501208
- 2501208
- 2501208
- 37182420
- 2501205
- 24308127
- 24308127
- 29839560
- 29839560
- 49456295

Figure 4. continued.

*Cd02960* (2)
AGR
Homo sapiens(2)
5453541
66774045

*Cd02962* (1)
TMX2
Homo sapiens(1)
7705726

*Cd02963* (1)
TRX_DnaJ
Homo sapiens(1)
55960250

*Cd02964* (3)
TryX_like_family
Homo sapiens(5)
⊞ 19923987
⊞ 55662334
⊞ 33149331

*Cd02966* (1)
TlpA_like_family
Homo sapiens(2)
⊞ 42476013

*Cd02968* (2)
SCO
Homo sapiens(2)
1WP0 C
8134662

*Cd02970* (3)
PRX_like2
Homo sapiens(3)
33150834
37183236
46957720

*Cd02971* (4)
PRX_family
Homo sapiens(8)
⊞ 1QMV A
⊞ 1PRX A
⊞ 1OC3 B
⊞ 1H4O H

*Cd02972* (1)
DsbA_family
Homo sapiens(2)
⊞ 33150564

*Cd02980* (1)
TRX_Fd_family
Homo sapiens(2)
⊞ 20455499

*Cd02981* (15)
PDI_b_family
Homo sapiens(25)
2BJX A
1BJX
⊞ 119530
⊞ 2501208
⊞ 31077035
21264492
21757251
37182195
⊞ 4557409
⊞ 55957226
⊞ 34531342
⊞ 4557409
⊞ 55957226
⊞ 34531342
⊞ 2507461

*Cd02982* (11)
PDI_b'-family
Homo sapiens(18)
2507460
21264492
27502832
37182195
⊞ 119530
⊞ 31077035
⊞ 33149331
⊞ 1208427
⊞ 4557409
⊞ 55957226
⊞ 34531342

*Cd02983* (1)
P5_C
Homo sapiens(1)
2501205

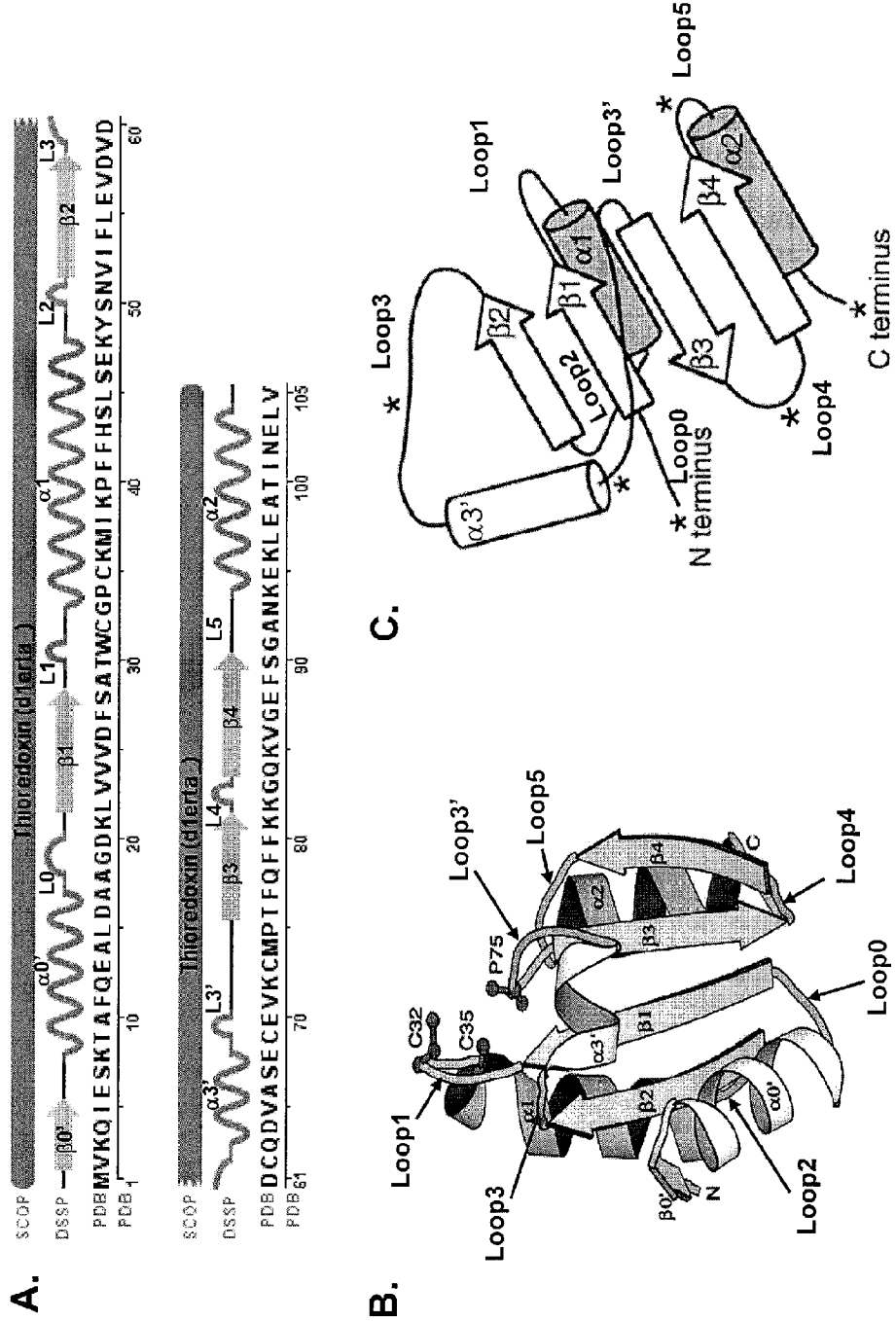
Figure 5. Loops in human thioredoxin: loops 1, 3, 3', & 5 are on the catalytic side of the molecule, and loops 0, 2 & 4 are on the opposite side.

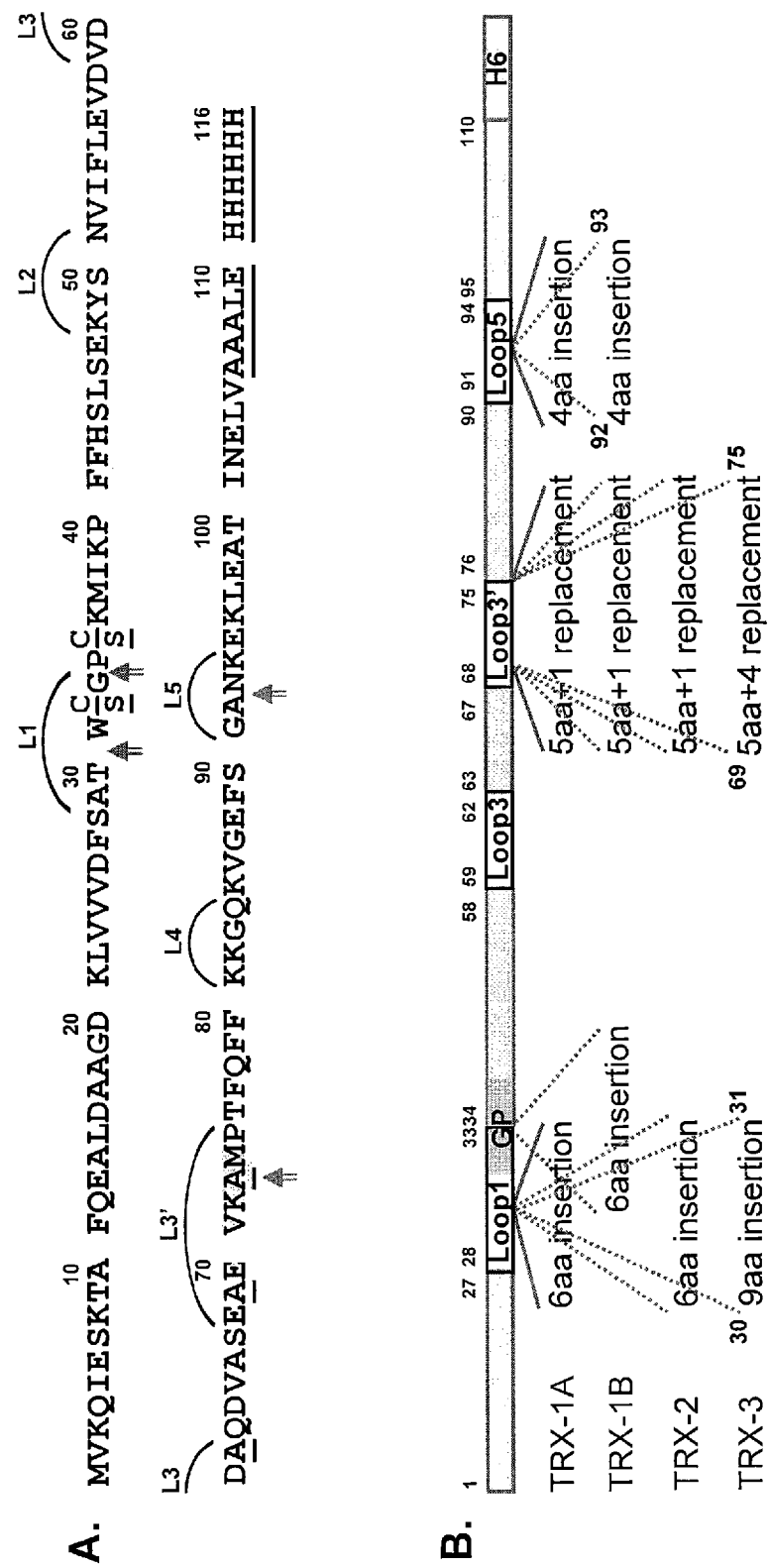
Figure 6. Solubility and stability screen on loop diversified libraries.

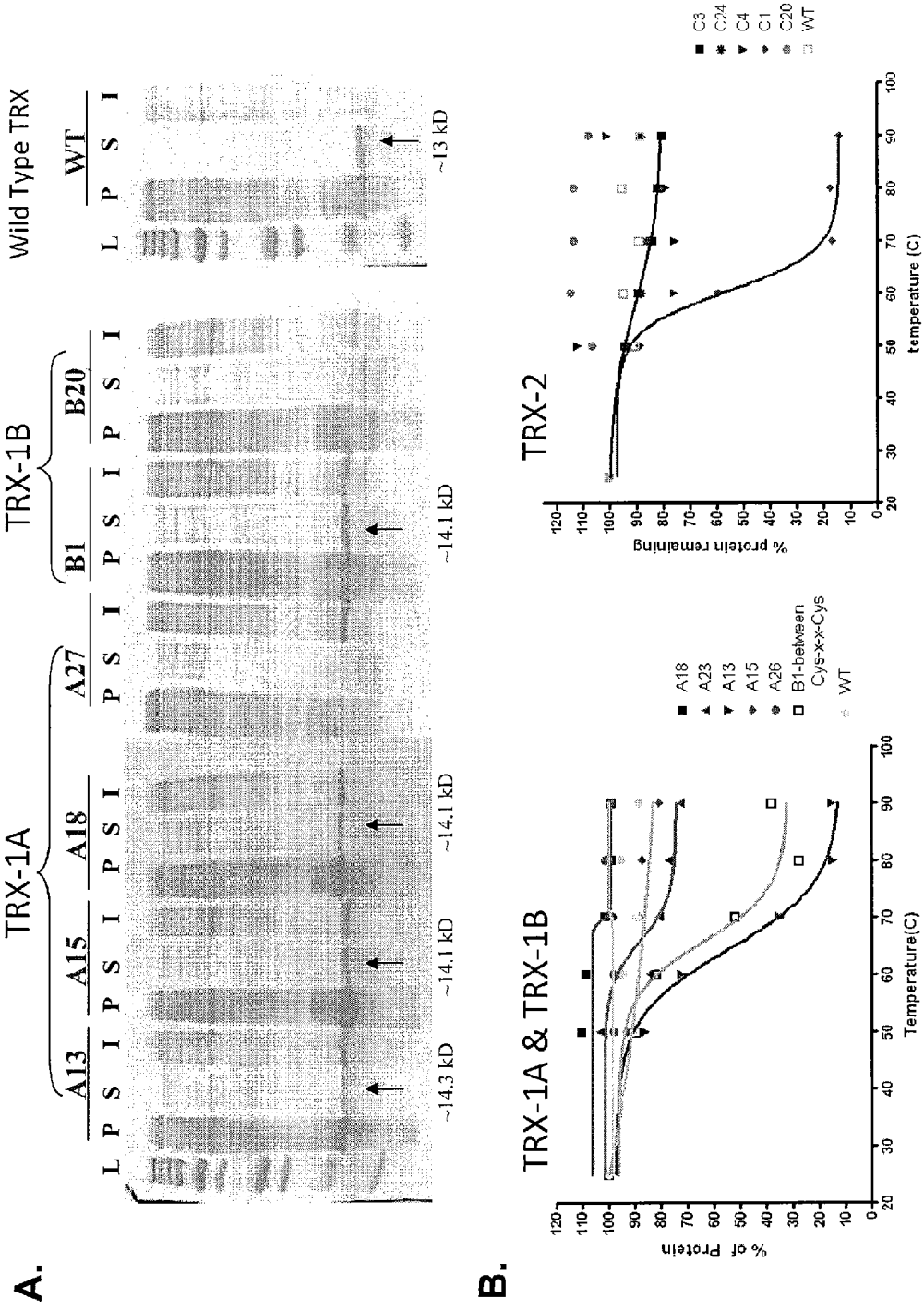
Figure 7. Solubility and thermostability screen of TRX-1A, TRX-1B, and TRX-2.

Figure 8. Phage display selection for CD5 binders from loop-diversified library TRX-3.

A.

MPMGSLQPLATLYLLGMLVASCLGRLSWYDPDFQARLTRSNSKCQGQLEV
YLKDGWHMVCSQSWGRSSKQWEDPSQASKVCQRLNCGVPLSLGPFLVTYT
PQSSIICYGQLGSFSNCSHSRNDMCHSLGLTCLEPQKTTPPTTRPPTTT
PEPTAPPRLQLVAQSGGQHCAGVVEFYSGSLGGTISYEAQDKTQDLENFL
CNNLQCGSFLKHLPETEAGRAQDPGEPREHQPLPIQWKIQNSSCTSLEHC
FRKIKPQKSGRVLALLCSGFQPKVQSRLVGGSICEGTVEVRQGAQWAAL
CDSSSARSSLRWEEVCREQQCGSVNSYRVLDAGDPTSRGLFCPHQKLSQC
HELWERNSYCKKVFVTCQDPGPSGGGPGGSPGGSGENLYFQSGSGGPGS
GENLYFQGGSPSGGGAGGGGGSGGEFGGGSMDEKTTGWRGGHVVEGLAGE
LEQLRARLEHHPQGQREPGTGGGSHHHHHHPA

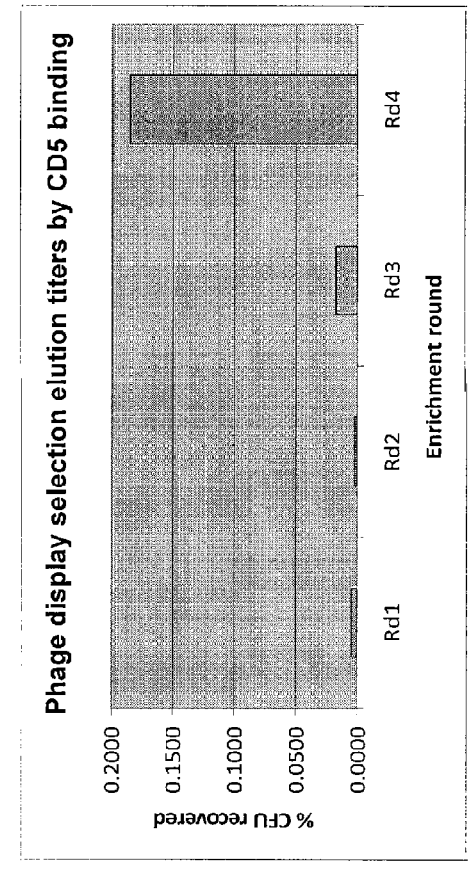

B.

Figure 9. Selected CD5 binders from loop-diversified library TRX-3.
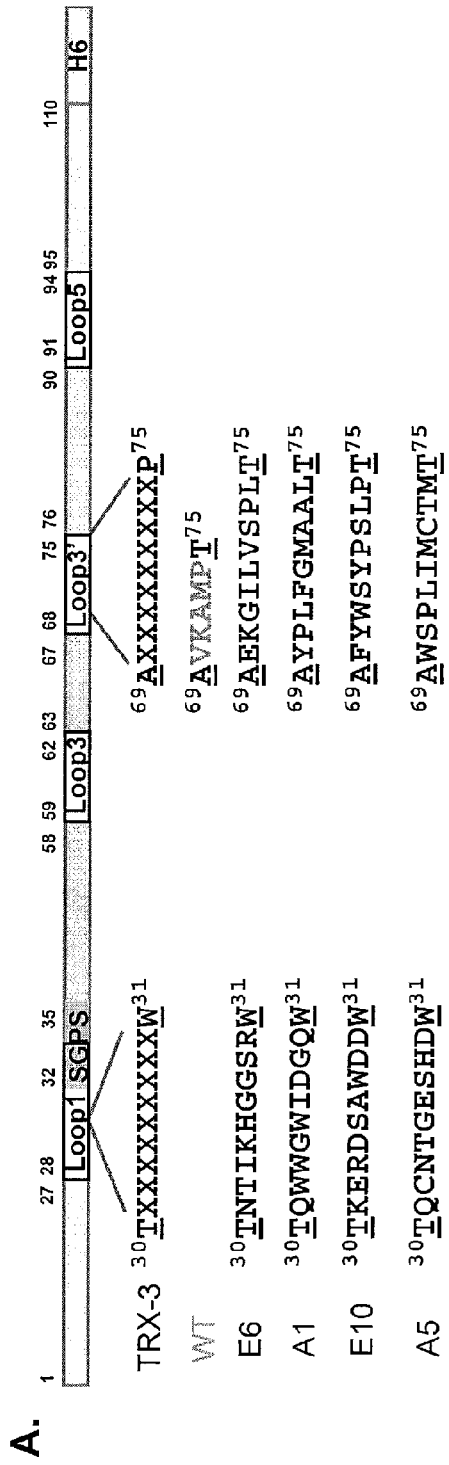
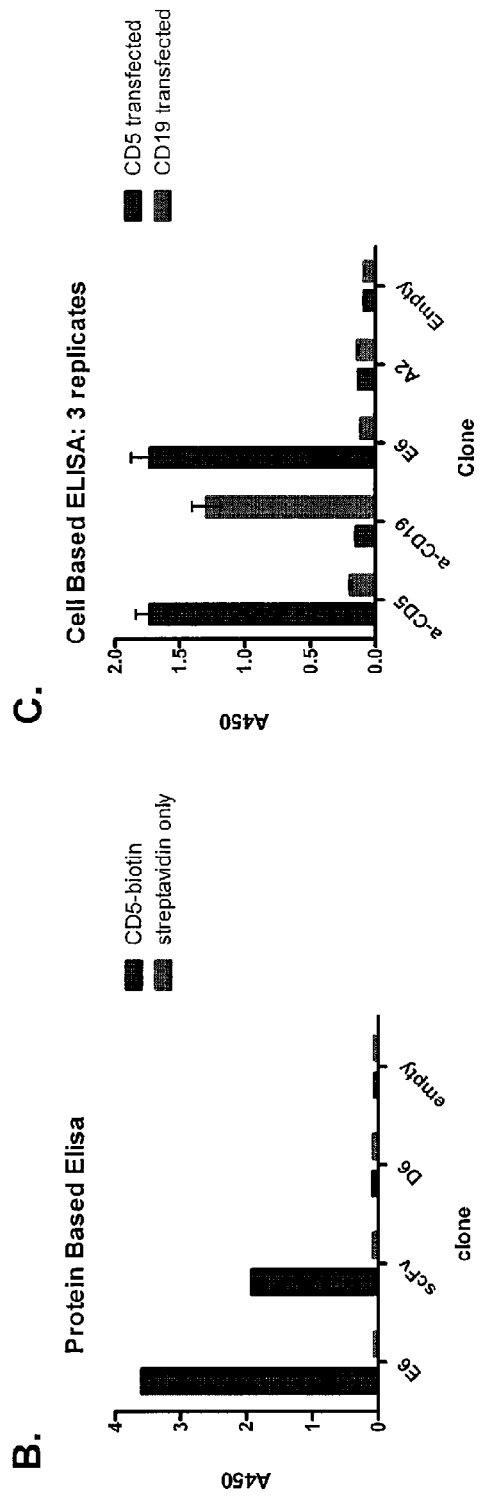

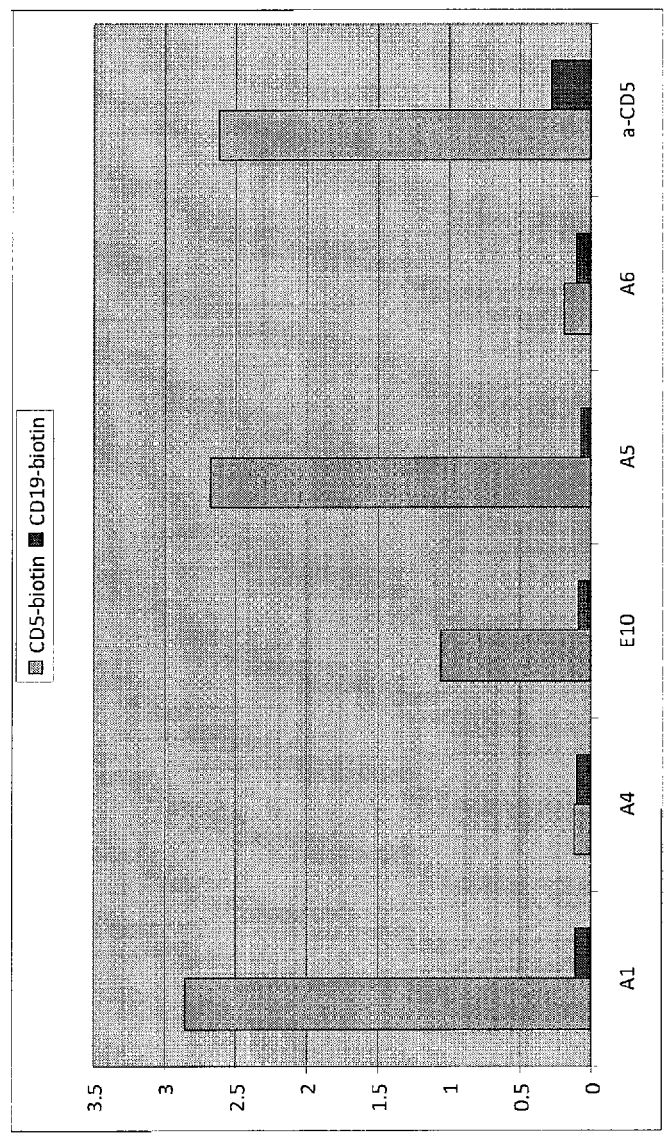
Figure 9. D.

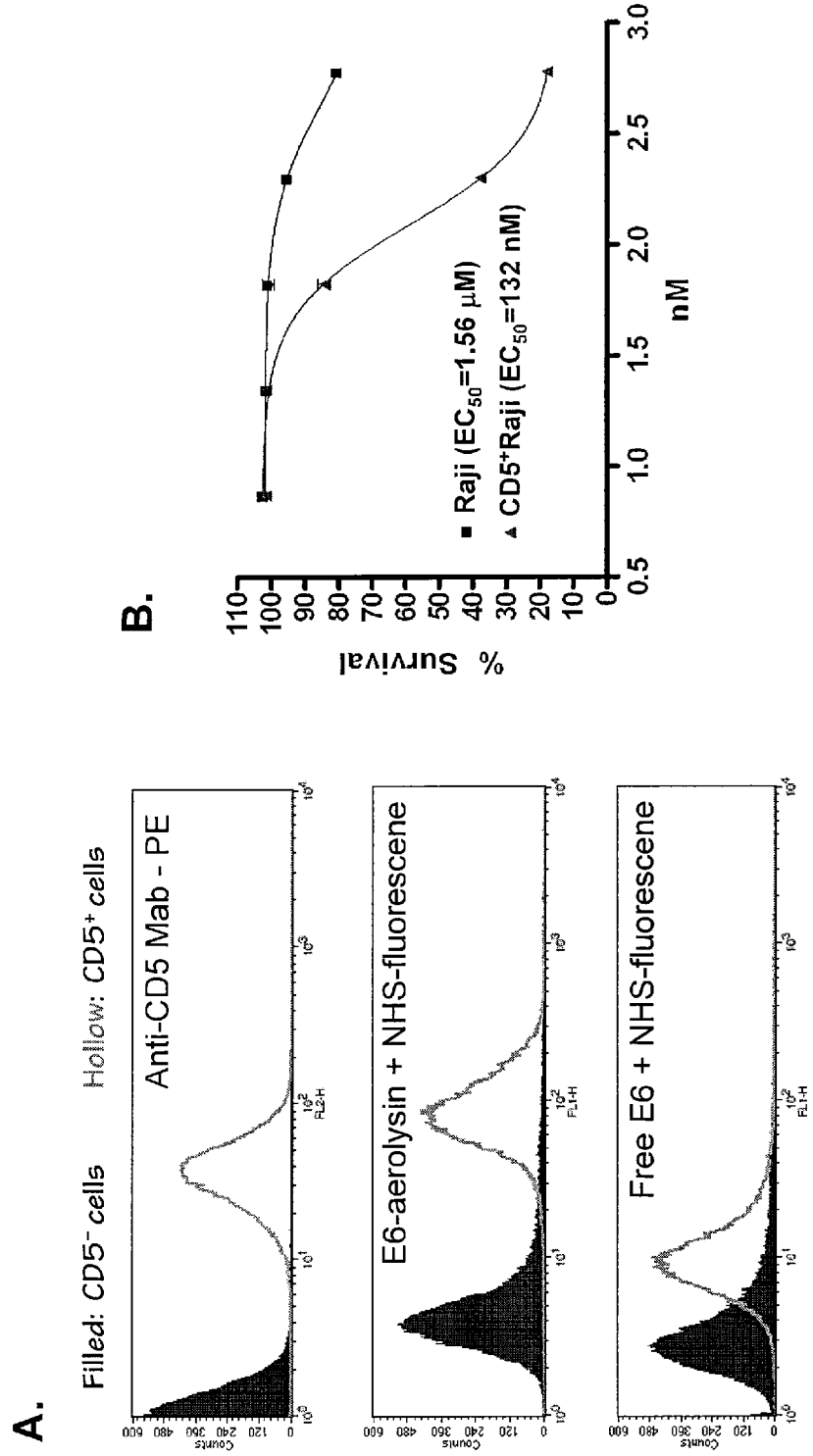
Figure 10. Specific binding and intoxication of E6-aerolysin fusion to CD5+ cells.

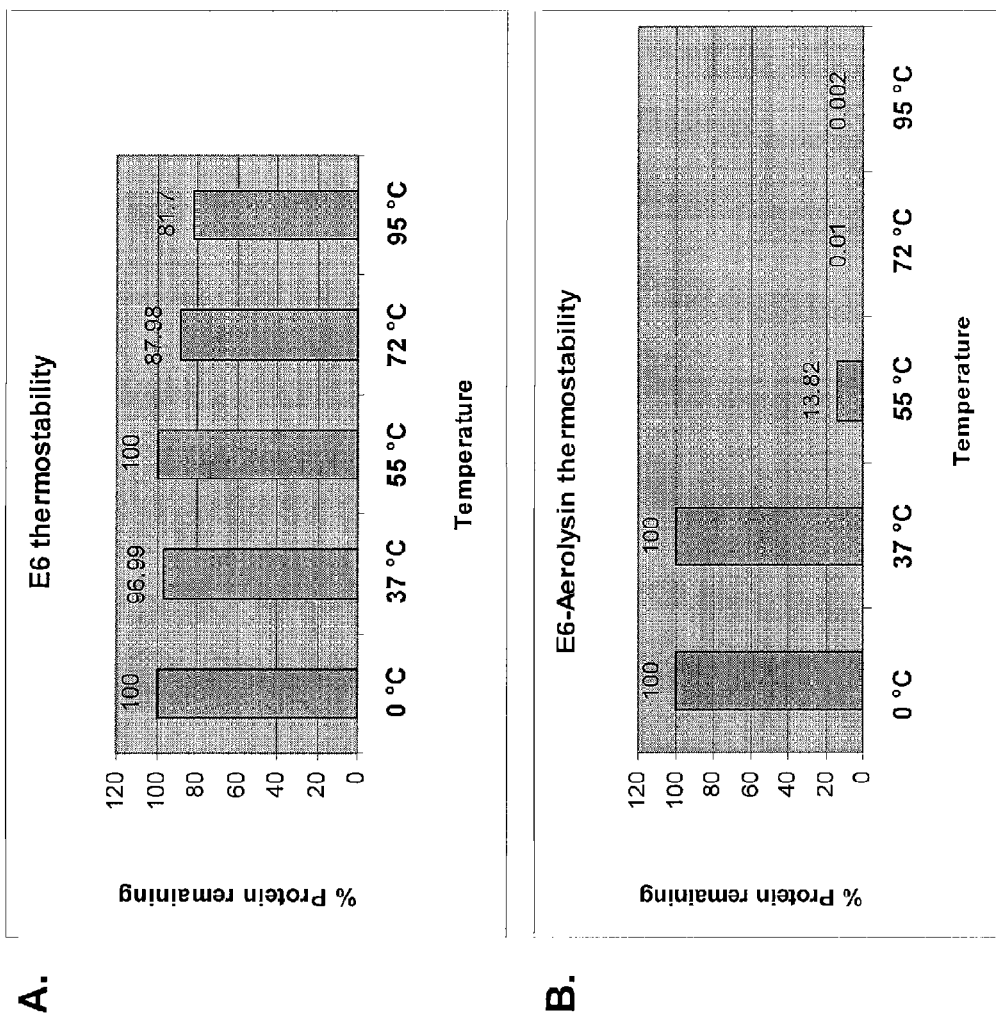
Figure 11. Thermostability screen of E6 free protein and E6-aerolysin fusion protein.

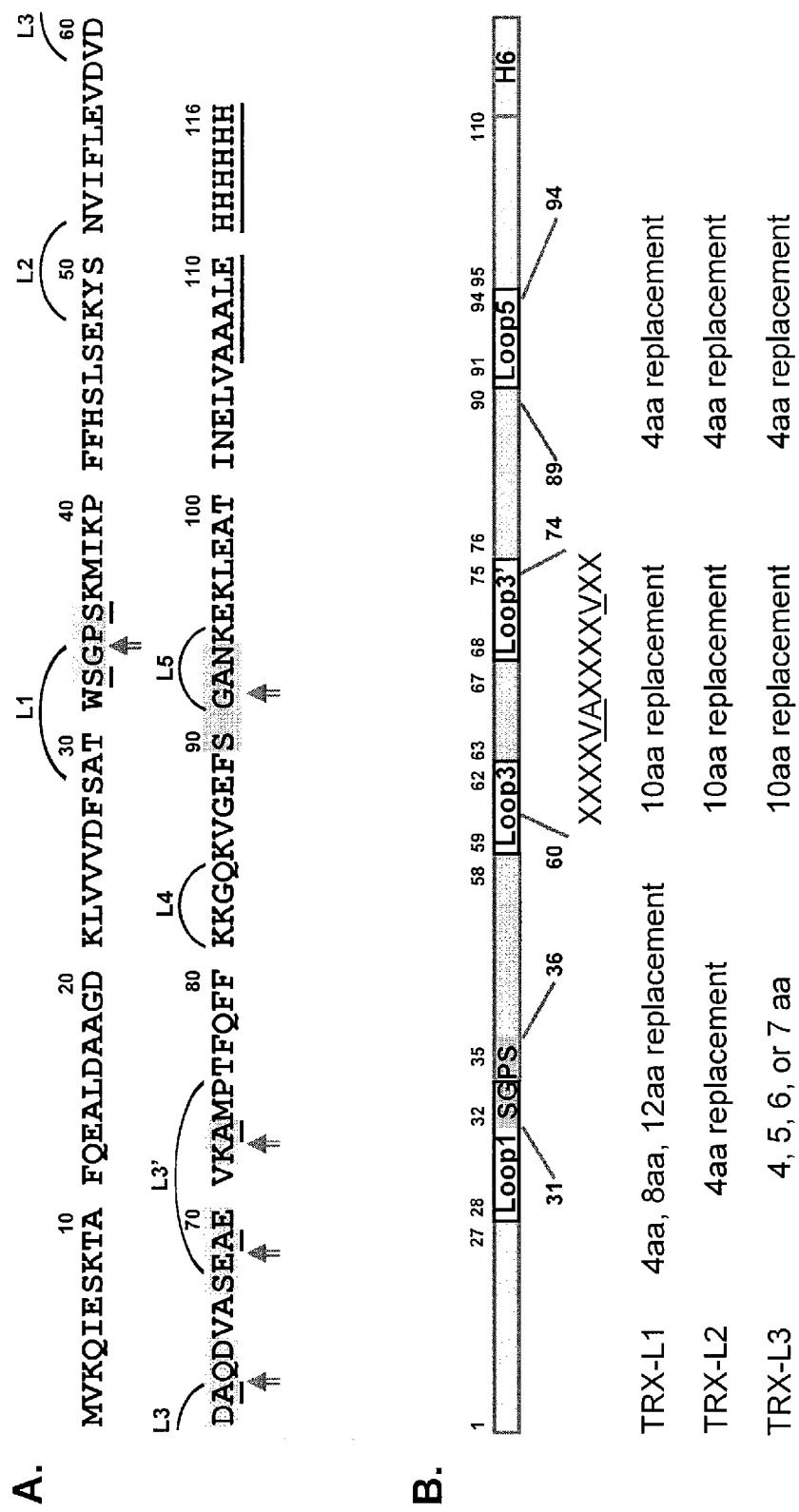
Figure 12. Loop diversified libraries used for EpCAM binder selections.

Figure 16.

```
     27 28  32  35       58 59   62 63  67 68  75 76              90 91   94 95        110
  1 |   Loop1 SGPS     |   Loop3    |  Loop3'  |                 | Loop5 |              H6 |

30T XXXXXXXXW31                    69A XXXXXXXXX P75
```

| Protein<br>Targets | In vivo Protein<br>Expression | # of Unique<br>Clones | Representative Binders | |
|---|---|---|---|---|
| | | | Loop 1 | Loop 3' |
| CD3ε | T cell receptor | 5 | C4: VTCDHEGCK | SNFAVTFFF |
| CD5 | T cells, B-CLL cells | 4 | E6: NTIKHGGSR | EKGILVSPL |
| CD19 | B cells | 2 | A1: KRNDNTSDT | FRRWNSRWG |
| CD22 | B cells | 3 | A4: RDPNNCRGT | CVLYSVGYA |
| EpCAM | Carcinoma-associated antigen | 22 | A6: NRNGEKHAH | GLLWSIPFR |
| LGR5 | Colon cancer stem cells | 5 | D2: RYEETTRQH | RVASKRSAF |
| HSA | Human plasma | 8 | E2: KNEKRDVAE | FGFFGFPVL |

Figure 17.

| Clone | Loop 1 | Loop 3' | Sequence Frequency | Round of Selection |
|---|---|---|---|---|
| WT TRX | -------- | AEV---KAM | | |
| A11 (HSA) | ANEQATKA* | FCFFCFPTF | 2/42 | R3 |
| C6 (HSA) | CQTGTKQLP | FGHFGFPTL | 1/42 | R3 |
| E1 (HSA) | RSENDRWNE | LIAGPFWYS | 3/42 | R3 |
| E2 (HSA) | KNEKRDVAE | FGFFGFPVL | 25/42 | R3 |
| E5 (HSA) | RRNERARDW | LAAGPFYLL | 5/42 | R3 |
| F3 (HSA) | GGTPGRRNR | FCEFCFPFL | 2/42 | R3 |
| G5 (HSA) | RLRTGGHPY | VYVSLSRHR | 3/42 | R3 |
| H6 (HSA) | DRKPWKTRG | FGLFSFPLL | 1/42 | R3 |
| F-rich Motif | XXXXXXXXX | FXXFXFPXX | | |
| AGPF Motif | XXXXXXXXX | LXAGPFXXX | | |

X represents any amino acid, * is a stop codon, - indicates that there is no amino acid at this position Biacore analysis of TRX-based HSA binders (TRX) and Renilla luciferase fusions (Rluc-TRX)

ENGINEERED THIOREDOXIN-LIKE FOLD PROTEINS

CROSS-REFERENCE TO RELATED APPLICATIONS

This application is the U.S. National Stage of International Application No. PCT/US2012/031212, filed Mar. 29, 2012, which claims benefit of U.S. Provisional Application No. 61/468,836, filed Mar. 29, 2011.

FIELD OF THE INVENTION

The present invention relates to engineered polypeptides comprising a thioredoxin-like fold protein domain with multiple disjoined regions of non-native sequences, methods for their production and for their use in binding or recognizing ligands of interest.

The instant application includes a sequence listing in electronic medium and submitted to the United States Patent and Trademark Office via the electronic filing system. The ASCII text file, which is incorporated-by-reference herein, is titled "29539-0191US1 ST25.txt," was created on Dec. 3, 2015, has a size of 136 kilobytes.

BACKGROUND OF THE INVENTION

The adaptive immune system is a highly evolved, flexible system for the recognition and neutralization of foreign organisms and macromolecules. At the core of adaptive immunity is an engine for the creation of a vast variety of different similar structures that have been diversified by combinatorial assembly of varied building blocks with highly random linker segments. The two principle recognition complexes of the higher vertebrate adaptive immune system, antibodies and the T cell antigen receptor, are similarly assembled, and function through their cognate cell types, B cells and T cells, to produce a coordinated resistance to pathogens. Although all elements of the adaptive recognition system of higher vertebrates are based on assemblies of monomer domains of the immunoglobulin fold, in cyclostomes, convergent evolution has created an adaptive immune system that is constructed by the assembly of recognition elements derived from leucine rich repeats.

The effector proteins of the B cell arm of the adaptive immune system, particularly antibodies of the IgG subtype, have many attractive properties as candidate therapeutic agents. IgG antibodies are highly soluble proteins with a long in vivo half-life that have weak immunogenicity within a given species. They often can be selected to have high affinities for their targets and are known to have few intrinsic safety liabilities. As a class IgG antibodies have relatively predictable behavior in vitro and in vivo, and in recent years recombinant antibodies of substantially human sequence have played a major role in therapeutic medicine as universal recognition moieties for a number of targets in different diseases. Human monospecific antibodies of the IgG subtype provide high specificity, bivalency, fully human composition, and long plasma half-life. The known limitations of antibodies relate largely to their biophysical properties (high molecular weight, multi-domain assemblage, disulfide bonds, glycosylation), which require eukaryotic manufacturing processes that are more complex and more expensive than their prokaryotic counterparts.

Scaffolds based on different human or non-human proteins or protein domains have emerged as an independent class of alternative therapeutic molecules. The status of alternative scaffolds and selection procedures used to identify high affinity binding proteins based on those scaffolds has been reviewed (Gebauer, M. & Skerra, A. Curr. Opin. Chem. Biol. 2009, 13:245-255). Different proteins have been investigated as frameworks for bringing the diversified sequences to targets, including affibodies, lipocalins, ankyrin-repeat proteins, natural peptide binding domains, enzymes, GFP, small disulfide-bonded peptides, protease inhibitors, and others.

Although for prospective therapeutic applications to date, alternative scaffolds have largely been employed as neutralizing agents for ligand-receptor interaction, cytokine, toxin, or Fc-fusions are being investigated to confer on the binding protein a cytostatic or cytotoxic effect similar to that achieved through antibody-dependent cellular cytotoxicity (ADCC). The potential role of alternative scaffolds in diagnosis is important since large arrays of specific small reagents could be produced to many different targets. Compared to antibodies, small scaffolds should have better tissue penetration which could be advantageous for solid tumor targets (Zahnd C., et al. *Cancer Res.* 2010, 70(4):1595-1605).

Even though it has not heretofore been emphasized in the development of antibody-like binders using engineered scaffold proteins, the evolvability of a parent protein has been recognized as a key factor for successful directed evolution of enzymatic activities (Bloom, J. D. & Arnold, F. H, *Proc. Natl. Acad. Sci.,* 2009, 106:9995-10000). Two evolutionary concepts have been used to provide rational basis for increased evolvability of enzymes: (i) the conservation of catalytic mechanisms, and (ii) the functional promiscuity. First, the knowledge of the catalytic motifs responsible for conserved aspects of catalysis in mechanistically diverse superfamilies could be used to identify promising templates for protein engineering. Second, protein evolutions often proceed through promiscuous intermediates, suggesting that naturally promiscuous templates (for a target reaction) could enhance protein engineering strategies (Khersonsky, O., et al., *Curr. Opin. Chem. Biol.* 2006, 10:498-508).

Catalysis of different chemical reactions by evolutionarily related proteins has been observed in several protein fold classes. The thioredoxin fold is found in thioredoxin superfamily of proteins that serve a wide variety of functions, including protein disulfide isomerases, DsbAs, the glutaredoxins, glutathione S-transferases, calsequestrins, and glutathione peroxidases and peroxiredoxins (Copley, S. D. et al. *Biochemistry,* 2004, 43:13981-13995). These proteins have been shown to interact with many different types of protein substrates, demonstrating the ability of the thioredoxin fold to recognize diverse targets. Moreover, based on combined sequence, structural, and functional evidence for homology, more than 723 proteins have been identified to possess a thioredoxin-like fold (containing different circular permutations including that of thioredoxin fold) and may be divided into at least eleven different evolutionary families (Qi, Y. & Grishin, N. V., *Proteins* 2005, 58:376-388). Further computational analysis revealed that the thioredoxin-like fold class, as described in Qi, Y. & Grishin, N. V., *Proteins* 2005, 58:376-388, is the largest sets of proteins likely to have evolved from a common ancestor, incorporating at least eighteen individual superfamilies and comprising 29,206 sequences (Atkinson, H. J. & Babbitt, P. C., *PloS Comput. Biol.* 2009, 5(10): e1000541). The evolutionary relationships among some of these protein families have been documented. The observed flexibility and adaptation of thioredoxin-like fold makes it extremely suitable for the construction of proteins with novel functions. Sequence alignment of proteins from the thioredoxin-like fold families also reveals the high degree of sequence variations in the fold, implying its potential to allow large numbers of mutations to be explored during directed evolution experiments for the selection of prospective binders.

Many members of the thioredoxin superfamily share two features in common: they contain a short sequence motif that includes a -CPGC- sequence (the active site) and an overall structure containing this motif that bears the same topology as thioredoxin. Laboratory evolution of the proteins with thioredoxin fold further demonstrates the flexibility of the fold and helps illustrate how various functions can be acquired by individual members that did not possess these functions prior to the imposed selection (Pan, J. L. & Bardwell, J. C., *Protein Sci.*, 2006, 15:2217-2227). For example, substitution of thioredoxin's active site CGPC to DsbA's active site CPHC can result in a protein that functions very similarly to DsbA. Another example of in vitro evolution is the selection of thioredoxin mutants that can compensate for the whole DsbA-DsbB pathway. A mutation from CGPC to CACC in exported versions of thioredoxin was capable of complementing null mutations in the DsbA-DsbB pathway. They do so by acquiring a 2Fe-2S iron-sulfur cluster, and presumably a whole new mechanism of action. This shows that thioredoxin is extremely amenable to mutation, conferring the protein with new catalytic properties and the ability to participate in new redox reactions. Conversion of a peroxiredoxin into a disulfide reductase was accomplished by a single TCT insertion in the gene ahpC, which allowed the AhpC protein product to function as a disulfide reductase as opposed to the peroxiredoxin role that it normally participates in within the cell. AhpC has lost its peroxidase activity while gaining a disulfide reductase activity. Additionally, some multi-domain thioredoxin super family proteins contain a non-catalytic thioredoxin-like domain that involves in substrate binding (Pedone, E. et al. *Cell. Mol. Life Sci.*, 2010, July 13, Epub ahead of print). For example, human protein disulfide isomerase (PDI) contains two catalytic domains, a and a', and two non-catalytic domains, b and b'. Biochemical studies have established that the b' domain is sufficient for binding small peptide substrates, even though catalytic domains a and a' are also involved in binding of larger protein substrates. Within the b' domain, the implicated ligand binding site is a small hydrophobic pocket located in a position homologous to that of the active site in the catalytic domains.

These examples show that thioredoxin and thioredoxin-like proteins can evolve, both in function and substrate specificity, with only a few amino acid changes in the protein. Although the function and specificity has changed, the thioredoxin fold is still conserved.

Thioredoxin (Trx) is the founding member of the thioredoxin superfamily (Martin, J. L. *Curr. Biol.*, 1995, 3:245-250). It is a 12-kDa protein that is involved in many reactions including reducing improper disulfides that have formed in the cytosol, donating reductive equivalents to ribonucleotide reductase, and being an indicator of the intracellular redox status. The function of thioredoxin has been implicated in numerous pathways; principally, it provides a protective role against many different types of damaging stresses (Lillig, C. H. & Holmgren, A., *Antioxid. Redox Signal.*, 2007, 9(1):25-47). In addition to its anti-oxidative effect by dithiol-disulfide exchange in its active site, Trx has anti-apoptotic and anti-inflammatory effects. Trx overexpression has been shown to be effective in a wide variety of animal models for oxidative and inflammatory disorders. An administration of recombinant Trx protein is also effective in animal models for severe acute lung diseases where Trx is likely to act with its anti-inflammatory properties (Nakamura H. et al., *Adv. Drug Deliv. Rev.* 2009, 61(4):303-309). Although it has no signal peptide, Trx is released from cells in response to oxidative stress. Trx is found in circulation and shows anti-chemotactic effects for neutrophils and inhibitory effects against macrophage migration inhibitory factor (MIF). Neovascularization is also suppressed by Trx via inhibition of the complement activation. The anti-inflammatory effects of Trx suggest that it is not likely to elicit immunogenic responses in vivo.

Pharmacokinetics of Trx has also been studied (Nakamura H. et al., *Adv. Drug Deliv. Rev.* 2009, 61(4):303-309). When recombinant human Trx was injected intravenously, its half-life in plasma was measured to be roughly 1 h in mouse, 2 h in rat, and 8 h in monkey. In healthy volunteers, Trx is circulating in plasma at the concentrations of 10-30 ng/ml and, in the kidney it is excreted through the glomerulus and mostly reabsorbed by the proximal tubules, such that Trx levels in the urine of healthy volunteers are quite low and usually undetectable. When an excess amount of Trx such as 10 mg/kg is injected into animals, Trx protein is excreted into the urine as an immunologically intact form, suggesting that this protein is not likely to be metabolized. Tissue deposition of Trx after intravenous injection was limited. Five plasma proteins were identified to interact with recombinant Trx: apolipoprotein A-I, scavenger receptor (cysteine rich domain), fibrinogen (gamma polypeptide), complement factor H, and albumin. Interaction with albumin may be particularly beneficial for prolonged half-life in plasma.

SUMMARY OF THE INVENTION

In one aspect, the invention features an engineered thioredoxin-like fold protein with at least one of its domains comprising two or more loops being modified through loop-diversification.

In another aspect, the invention features a method for preparing an enriched composition of target-binding, loop-diversified engineered thioredoxin-like fold proteins by (i) providing a collection of nucleic acids encoding the loop-diversified engineered thioredoxin-like fold proteins in a display-conducive context, (ii) expressing the collection of nucleic acids in vivo or in vitro to provide a collection of loop-diversified engineered thioredoxin-like fold proteins operably linked to the nucleic acid that encodes them, (iii) contacting the expressed engineered thioredoxin-like fold proteins with a target; (iv) removing expressed engineered thioredoxin-like fold proteins that do not bind to the target; and (v) recovering the engineered thioredoxin-like fold proteins enriched for binding to the target.

In another aspect, the invention features another method for preparing an enriched composition of target-binding, loop-diversified engineered thioredoxin-like fold proteins by: (i) providing a collection of nucleic acids encoding the loop-diversified engineered thioredoxin-like fold proteins, (ii) expressing the collection of nucleic acids in vivo or in vitro to provide a collection of loop-diversified engineered thioredoxin-like fold proteins, (iii) contacting the expressed engineered thioredoxin-like fold proteins with a target; and (iv) identifying collections of expressed engineered thioredoxin-like fold proteins that bind to the target.

The invention also features a method for identifying individual target-binding, loop-diversified engineered thioredoxin-like fold proteins by: (i) providing a collection of nucleic acids encoding the loop-diversified engineered thioredoxin-like fold proteins, (ii) expressing the collection of nucleic acids in vivo or in vitro to provide a collection of optionally individually indexed, loop-diversified engineered thioredoxin-like fold proteins, (iii) contacting the optionally individually indexed engineered thioredoxin-like fold proteins with a target; and (iv) identifying collections or individual engineered thioredoxin-like fold proteins that bind to the target.

In yet another aspect, the invention features an isolated nucleic acid encoding an engineered thioredoxin-like fold protein or a loop-diversified engineered thioredoxin-like fold protein in an expression-conducive context.

Another aspect of the invention features the conjugates of a protein including at least one optionally engineered thioredoxin-like fold protein domain to one or more small molecule drugs or toxins.

Still another feature of the invention is a fusion protein between a protein including at least one optionally engineered thioredoxin-like fold protein domain and another protein such as a protein toxin or protoxin, an antibody, and an enzyme.

The invention also features a method for chemically modifying and purifying a protein including at least one optionally engineered thioredoxin-like fold protein domain to achieve optimal in vivo pharmacokinetic properties of the protein by: (i) modifying the protein with a single cysteine near the c-terminus that is then modified with polyethelene glycol, and (ii) purifying the modified protein by anion exchange chromatography.

Another feature of this invention include modification with polyethelene glycol achieved by: (i) modifying the protein near its c-terminus with a peptide tag that is a substrate of a microbial transglutaminase (e.g., LLQG; SEQ ID NO:1) or a substrate of a microbial sortase (e.g., LPETG; SEQ ID NO:2), and (ii) conjugate the protein with amino-modified polyethelene glycol using the corresponding microbial transglutaminase or sortase.

The invention also features engineered thioredoxin-like fold proteins as high affinity binding proteins to the selected targets of Tables 2 and 3, and cited in Supplementary Tables S1-S9 of U.S. Provisional Application No. 61/468,836, specifically incorporated herein by reference.

One preferred embodiment of the present invention is an engineered thioredoxin-like fold protein comprising an engineered protein domain of the thioredoxin superfamily. A further preferred embodiment is an engineered thioredoxin-like fold protein comprising an engineered human protein domain of the thioredoxin superfamily.

Another preferred embodiment is an engineered thioredoxin-like fold protein comprising an engineered protein domain of the thioredoxin family. A further preferred embodiment is an engineered thioredoxin-like fold protein comprising an engineered human protein domain of the thioredoxin family.

A still preferred embodiment is an engineered thioredoxin-like fold protein comprising an engineered thioredoxin domain, preferably that of *Homo sapiens*.

In another embodiment, the invention features a sample containing a plurality of engineered thioredoxin-like fold proteins (e.g., $10^2$, $10^3$, $10^4$, $10^5$, $10^6$, $10^7$, $10^8$, $10^9$, or more distinct engineered thioredoxin-like fold proteins).

A further preferred embodiment of the invention features an engineered protein of the thioredoxin super family comprising a multiple loop-diversification within at least one of its thioredoxin-like fold domains.

In any of the foregoing aspects, the thioredoxin-like fold protein domain may contain additional point mutations, including mutations at the active site, e.g., -$^{32}$CGPC$^{35}$ (SEQ ID NO:3)- to -$^{32}$SGPS$^{35}$ (SEQ ID NO:4)- in a thioredoxin molecule.

In any of the foregoing aspects where the engineered thioredoxin-like fold protein is an engineered protein of the thioredoxin superfamily, the engineered thioredoxin-like fold protein preferably does not contain a peptide insertion at the active site corresponding to -CGPC- or its mutant -SGPS- to afford a protein comprising, e.g., -CG-peptide-PC- or its mutant -SG-peptide-PS-.

In any of the foregoing aspects of the invention, the engineered thioredoxin-like fold protein binds (e.g., specifically binds) a particular target (e.g., a target listed in Tables S1-S9 of U.S. Provisional Application No. 61/468,836, specifically incorporated herein by reference, 2, or 3).

By "branched polyalkylene glycol" is meant a branched polymer created by the joining of one or more optionally substituted oligomers or polymers of units of the form —(O—CR$_1$R$_2$—CR$_3$R$_4$)$_n$—O—R$_5$, where R$_1$, R$_2$, R$_3$, R$_4$, and R$_5$ are the same or different and selected from H, F, or lower alkyl optionally substituted with one or more F; and n is 3 or greater. A branched polyalkylene glycol contains one or more linker structures (branches) of the form A-Y-linker-(X$_1$X$_2$) where X$_1$=—(O—CR$_1$R$_2$—CR$_3$R$_4$)$_n$—O—R$_5$ and Y may be a bond or a linear polyalkylene glycol and A is a group selected to provide covalent or stable noncovalent linkage to a protein. As used, the term branched polyalkylene glycol includes block or random copolymers of units corresponding to the formula above, wherein the substituents R$_1$, R$_2$, R$_3$, R$_4$, and R$_5$ may vary from block to block or from monomer to monomer, for example as in a block or random copolymer of polyethylene and polypropylene glycols.

By "coding sequence" is meant the sequence of nucleic acid residues that upon translation give rise to a polypeptide.

By "display" is meant any system that permits the enrichment or identification of a target-binding protein by (i) contacting a mixture of target-binding and target-nonbinding proteins each operably linked to a nucleic acid encoding said target-binding or target-nonbinding protein and (ii) separating said target-binding proteins from said target-nonbinding proteins to provide a composition enriched in the target-binding proteins compared to the initial composition.

By "display-conducive context" means any form in which a target-binding protein can be expressed such that it is available to both bind to a target and retain an operable linkage or physical relationship (for example, by association with the same host cell, phage, or fusion construct) to a nucleic acid encoding said target-binding protein.

By "engineered protein of the thioredoxin superfamily" is meant a protein comprising one or more domains derived from a protein of the thioredoxin superfamily that have been modified by addition, deletion, replacement, or substitution of one or more amino acid residues.

By "engineered thioredoxin-like fold protein" is meant a protein comprising one or more domains derived from a thioredoxin-like fold protein that have been modified by addition, deletion, replacement, or substitution of one or more amino acid residues.

By "expressible clone" is meant a recombinant nucleic acid construct bearing an open reading frame that can be translated from N-terminus to C-terminus without termination. A "non-expressible clone" is a recombinant nucleic acid construct bearing an open reading frame that contains either frameshift or termination mutations that prevent complete translation of the coding sequence.

By "expression-conducive context" is meant the appropriate combination of flanking sequences, vector elements, regulatory sequences, or other nucleic acid sequences empirically determined to support, improve, or regulate the production of a polypeptide chain from the sequence that encodes it. The production of the polypeptide chain can be either in vitro or in vivo. For example, an expression-conducive context for a prokaryotic expression system might comprise an optionally regulated promoter of bacterial or bacteriophage origin, a ribosome binding sequence, the coding sequence of the protein to be expressed, and an optional transcriptional termination sequence. An expression-conducive context for prokaryotic in vitro expression might comprise an RNA or translatable nucleic acid comprising a ribosome binding sequence and the coding sequence of the protein to be expressed, or such expression-conducive context for prokaryotic in vitro expression might comprise a DNA or transcribable nucleic acid encoding such RNA or translatable nucleic acid as well as regulatory sequences permitting the transcription of said DNA or transcribable nucleic acid to afford said RNA or translatable nucleic acid. An expression-conducive context for eukaryotic in vitro expression might comprise an RNA or translatable nucleic acid bearing the coding sequence of the protein to be expressed and optionally bearing 5' and 3' flanking sequences that provide RNA stability or improve the efficiency of translation.

By "extension-diversified" as applied to a thioredoxin-like fold protein is meant a thioredoxin-like fold protein wherein at least one terminus, either the N-terminus or the C-terminus, of a beta barrel has been replaced and/or extended with an amino acid sequence of no greater than 30% (e.g., less than 25%, 20%, 15%, 10%, 5%, 1%, 0.1%, or less) identity to the original sequence. An extension-diversified engineered thioredoxin-fold like protein may have one or both termini extended or modified.

By "individually indexed collection" is meant any collection of species constituted as mixtures or not, so composed that the activity of any individual member can be inferred from the analysis of the activities of all mixtures.

By "linear polyalkylene glycol" is meant an optionally substituted oligomer or polymer of units of the form A-(O-$CR_1R_2$—$CR_3R_4)_n$—O—$R_5$, where $R_1$, $R_2$, $R_3$, $R_4$, and $R_5$ are the same or different and selected from H, F, or lower alkyl optionally substituted with one or more F; A is a group selected to provide covalent or stable noncovalent linkage to a protein; and n is 3 or greater. As used the term linear polyalkylene glycol includes linear block or random copolymers of units corresponding to the formula above, wherein the substituents $R_1$, $R_2$, $R_3$, $R_4$, and $R_5$ may vary from block to block or from monomer to monomer.

By "library" or "pool" is meant a collection of two or more species constituted as a single mixed entity. Preferably, a "library" or "pool" includes at least $10^2$, $10^5$, $10^{10}$, $10^{13}$, or $10^{15}$ members or some range within these numbers.

By "loop-diversification" as applied to a thioredoxin-like fold protein domain or a protein domain of the thioredoxin superfamily is meant a thioredoxin-like fold protein or a protein of the thioredoxin superfamily wherein at least one loop connecting beta strands and alpha helices of the fold has been replaced with an amino acid sequence of no greater than 30% identity (e.g., less than 25%, 20%, 15%, 10%, 5%, 1%, 0.1%, or less identity) to the original sequence.

By "multiple loop-diversifications" as applied to a thioredoxin-like fold protein domain or a protein domain of the thioredoxin superfamily is meant a thioredoxin-like fold protein or a protein of the thioredoxin superfamily wherein more than one loop connecting beta strands and alpha helices of the fold have been replaced with an amino acid sequence of no greater than 30% identity (e.g., less than 25%, 20%, 15%, 10%, 5%, 1%, 0.1%, or less identity) to the original sequence.

By "nucleic acid" is meant an optionally substituted deoxyribonucleic acid or ribonucleic acid or homologous polymer of nucleic acid bases or base analogs that can be either copied to provide an image or replica of itself or that can be translated to form a peptide, polypeptide, or protein.

By "operably linked" or "operable linkage" is meant a stable, covalent or noncovalent attachment of two or more species so described that is capable of providing a statistical association of the operably linked species sufficiently powerful that the identification or extraction of one element permits the identification or recovery of the other element in at least 10% (e.g., at least 20%, 30%, 40%, 50%, 75%, 90%, 95%, 99%, or more) of attempts.

By "peptide" is meant an optionally substituted oligomer or polymer of naturally occurring or unnatural amino acids covalently linked by one or more amide bonds.

By "protein domain of the thioredoxin superfamily" is meant a member of the thioredoxin superfamily, a large, diverse group of proteins containing a thioredoxin fold, identified by databases of conserved protein domains, e.g., Pfam, as family cd01659. Many members contain a classic Trx domain with a redox active CXXC motif (SEQ ID NO:5). They function as protein disulfide oxidoreductases (PDOs), altering the redox state of target proteins via the reversible oxidation of their active site dithiol. The PDO members of this family include Trx, protein disulfide isomerase (PDI), tlpA-like, glutaredoxin, NrdH redoxin, and the bacterial Dsb (DsbA, DsbC, DsbG, DsbE, DsbDgamma) protein families. Members of the family that do not function as PDOs but contain a Trx-fold domain include phosducins, peroxiredoxins and glutathione (GSH) peroxidases, SCO proteins, GSH transferases (GST, N-terminal domain), arsenic reductases, Trx-like ferredoxins and calsequestrin, among others.

By "protein domain of the thioredoxin family" is meant a thioredoxin fold domain of member of the thioredoxin family identified by Pfam as family cd02947. It is composed of two groups: Group I, which includes proteins that exclusively encode a Trx domain; and Group II, which are composed of fusion proteins of Trx and additional domains. Group I Trx is a small, ancient protein that can alter the redox state of target proteins via the reversible oxidation of an active site dithiol, present in a CXXC motif, partially exposed at the protein's surface. Trx reduces protein disulfide bonds, resulting in a disulfide bond at its active site. Oxidized Trx is converted to the active form by Trx reductase, using reducing equivalents derived from either NADPH or ferredoxins. By altering their redox state, Trx regulates the functions of at least 30 target proteins, some of which are enzymes and transcription factors. It also plays an important role in the defense against oxidative stress by directly reducing hydrogen peroxide and certain radicals, and by serving as a reductant for peroxiredoxins. At least two major types of functional Trxs have been reported in most organisms; in eukaryotes, they are located in the cytoplasm and the mitochondria. Higher plants contain more types (at least 20 Trx genes have been detected in the genome of *Arabidopsis thaliana*), two of which (types f and m) are located in the same compartment, the chloroplast. Also included in the alignment are TRX-like domains which show sequence homology to Trx but do not contain the redox active CXXC motif. Group II proteins, in addition to either a redox active Trx or a Trx-like domain, also contain additional domains, which may or may not possess homology to known proteins.

By "protein toxin or protoxin" is meant a polypeptide that has the latent (protoxin) or manifest (toxin) ability to inhibit cell growth (cytostasis) or to cause cell death (cytotoxicity). Examples of such toxins or protoxins include, without limitation, Diphtheria toxin, *Pseudomonas* exotoxin A, Shiga toxin, and Shiga-like toxin, anthrax toxin PA, pore-forming toxins or protoxins such as Proaerolysin, hemolysins, pneumolysin, Cryl toxins, *Vibrio* pro-cytolysin, or listeriolysin; Cholera toxin, *Clostridium septicum* alpha-toxin, Clostridial neurotoxins including tetanus toxin and *botulinum* toxin; gelonin; nucleic acid modifying agents such as ribonuclease A, human pancreatic ribonuclease, angiogenin, and pierisin-1, apoptosis-inducing enzymes such as caspases, and ribosome-inactivating proteins (RIPs) such as Ricin, Abrin, and Modeccin. A protoxin is a form of toxin precursor that must undergo modification to become an active toxin. Preferable forms of protoxins for the present invention include those that can be activated by a proteolytic cleavage event.

By "small molecule drug or toxin" is meant a non-polymer (e.g., non-protein or nucleic acid) compound that exhibits cycotoxicity to mammalian cells.

By "stable noncovalent linkage" is meant a noncovalent association that permits the continued proximity of the two or more elements such that after a period of time encompassing the expected duration of use of the two or more associated elements, no more than 50% (e.g., less than 40%, 30%, 25%, 20%, 15%, lo %, 5%, I %, 0.1%, or less) of the elements have disassociated. For example, a stable noncovalent linkage for a complex intended to persist for 3 hours at 37° C. will have a half-life of at least 3 hours at 37° C. The term "substitution" in the context of an amino acid sequence is taken to mean the chemical or enzymatic modification of one or more amino acid residues of a polypeptide to afford a substituted polypeptide. Common forms of substitution include attachment of prosthetic groups, polymers, nucleic acids, linkers, small natural or synthetic molecules or fragments thereof, such as modifying radicals, for example methyl or other lower alkyl, formyl, acetyl, or other lower acyl, phosphoryl, or sulfonyl.

By "thioredoxin-like fold protein" is meant a protein comprising one or more domains of the thioredoxin-like fold, a three-layer $\alpha/\beta/\alpha$ sandwich with a central four-stranded $\beta$-sheet flanked by $\alpha$-helices on each side, as described in Qi, Y. & Grishin, N. V., *Proteins.,* 2005, 58:376-388.

By "thioredoxin protein" is meant a protein comprising one or more domains derived from a thioredoxin protein of the thioredoxin family cd02947; thioredoxin is a single Trx domain protein containing a CXXC motif capable of reducing protein disulfide bonds.

BRIEF DESCRIPTION OF THE DRAWINGS

FIG. 1A is the topological diagram of the thioredoxin-like fold. The lines connecting different $\alpha$-helices (cylinders) and $\beta$-strands (arrows) represent loop regions. Dotted loops indicate the termini positions of the four types of circular permutations observed. No termini were observed at solid loop locations. Note that FIG. 1A is from FIG. 1A of Qi and Grishin, "Structural Classification of Thioredoxin-Like Fold Proteins," Proteins, 58:376-388 (2005).

FIGS. 1B-1E are a series three dimensional structures of the indicated proteins with a thioredoxin-like fold. Note that FIGS. 1B-E are from FIGS. 1C-F of Qi and Grishin, "Structural Classification of Thioredoxin-Like Fold Proteins," Proteins, 58:376-388 (2005).

FIG. 2 is the structure-based multiple sequence alignment of representative thioredoxin-like protein domains (SEQ ID NOs: 129-218, in descending order). Sequences are grouped according to 11 evolutionary families. The sequences corresponding to the four structures in FIG. 1 are indicated. Conserved residues within each family are highlighted in black. The diagram of secondary structures ($\alpha$-helices as cylinders and $\beta$-strands as arrows) is shown above the alignment. The termini of proteins of circular permutations different from that of thioredoxin are shown by a "|". Note that FIG. 2 is based, in part, on FIG. 2 of Qi and Grishin, "Structural Classification of Thioredoxin-Like Fold Proteins," Proteins, 58:376-388 (2005).

FIG. 3 shows the list of protein domain subfamilies of the thioredoxin superfamily (Pfam cd01659) that encompass protein domains containing the thioredoxin-like fold. The list is obtained from NCBI's "Conserved Domains" database.

FIG. 4 presents a compiled list of the GI numbers of the human proteins comprising a protein domain of the thioredoxin superfamily based on data obtained from the NCBI database. The GI numbers corresponding to proteins associated with US patents are underlined.

FIG. 5A shows the sequence of human thioredoxin aligned with corresponding secondary structures.

FIG. 5B is a schematic showing the three dimensional structure of human thioredoxin with all loops specified. Loop1, loop3, loop3', and loop5 are at the same side as the active site. Note that FIG. 2 is based, in part, on FIG. 1C of Qi and Grishin, "Structural Classification of Thioredoxin-Like Fold Proteins," Proteins, 58:376-388 (2005).

FIG. 5C is the schematic showing the three dimensional structure of human thioredoxin (minus the $\alpha0'$ and $\beta0'$ motifs) with all loops specified. Note that FIG. 5C is based, in part, on FIG. 2 of Martin, "Thioredoxin—a fold for all reasons," Curr. Biol., 3:245-250 (1995).

FIG. 6A shows the mutated human thioredoxin sequence (SEQ ID NO:220) that was used as template for generating the loop diversified protein libraries; mutations (relative to SEQ ID NO:219) are highlighted by underlined amino acids. The loops are indicated by arches across the peptide sequences. The loop-diversification schemes were shown by the arrows pointing between the amino acids (three insertion sites), or an arrow pointing to a shaded stretch of amino acids (the replacement of shaded peptide with random peptide sequences in loop3'). Library TRX-1B was generated using the template with wild type active site CGPC, and the other libraries were generated using the template with mutated SGPS sequence.

FIG. 6B is the schematic presentation of four loop-diversified libraries. For example, in TRX-1B library the insertion in loop1 is done at the active site between $C^{32}G^{33}$ and $P^{34}C^{35}$. In TRX-1A library contains a 6 amino acid insertion between $T^{30}$ and $W^{31}$ in loop1, 6 amino acids replacing the 5 amino acids in loop3', and a 4 amino acid insertion between $A^{93}$ and $N^{94}$ in loop5. Both TRX-2 and TRX-3 libraries contain loop-diversifications in loop1 and loop3', as indicated.

FIG. 7A shows the solubility screen of protein samples from randomly selected in-frame members of TRX-1A and TRX-1B, with wild type thioredoxin (WT) as a reference using PAGE. The expressed proteins were separated into soluble and insoluble fractions after high speed centrifugation. L: Protein Ladder, P: Post Induction, S: Soluble, I: Insoluble.

FIG. 7B is a graph showing the thermostability analysis results of all the clones tested along with the wild type thioredoxin (WT). Protein samples that remained in the supernatant after heat treatment and centrifugation were quantified and the % remained soluble plotted. A clones are the soluble members of TRX-1A, the B clone is from TRX-1B, and C clones are from TRX-2.

FIG. 8A is the amino acid sequence (SEQ ID NO:221) of a fusion protein containing the extracellular domain (ECD) of CD5, ECD-CD5-SBP-H8, which was used as the target for phage display selections for CD5 binders from loop-diversified library TRX-3. The underlined N-terminus sequence is the signal peptide, and the bold C-terminus sequence comprises the streptavidin binding protein (SBP) sequence and a His8 tag.

FIG. 8B is a graph showing the phage display selection elution titers after each round of selection from loop-diversified library TRX-3.

FIG. 9A is a graph showing the sequences of CD5 binders E6 (SEQ ID NOs:39 and 40), A1 (SEQ ID NOs:35 and 36), E10 (SEQ ID NOs:41 and 42), and A5 (SEQ ID NOs:37 and 38) selected from library TRX-3 and its alignment with wild type thioredoxin and TRX-3 library. Underlined amino acids adjacent to the randomized/selected sequences are shown to indicate the specific locations of the amino acid insertion and/or replacement within SEQ ID NOs:222 or 223.

FIG. 9B is a graph showing ELISA assay results with the selected CD5 binder E6, anti-CD5 scFv, non-CD5 binding control D6, or buffer alone, using CD5-biotin conjugate immobilized to wells of streptavidin plates.

FIG. 9C is a graph showing cell-based ELISA results. Binding to the surface of CD5 expressing cells and CD19 expressing cells were tested with anti-CD5 scFv, anti-CD19 scFv, TRX-based CD5 binder E6, non-CD5 binding control A2, and buffer alone.

FIG. 9D is a graph showing ELISA assay results with the selected CD5 binders A1, E10, and A5, anti-CD5 scFv, and non-CD5 binding clones A4 and A6, using CD5-biotin conjugate immobilized to wells of streptavidin plates.

FIG. 10A is a graph showing FACS analysis results in the selective binding of anti-CD5 antibody (top panel), E6 (bottom panel), as well as an E60-aerolysin fusion protein (middle panel) to CD5+Raji cells, but not to CD5-Raji cells.

FIG. 10B is a graph showing MTS cytotoxicity assay results of E6-aerolysin (wt) fusion protein on Raji cells and CD5+ Raji cells. The cells were plated at 50,000 cells per well, the fusion protein was pre-treated with furin for 6 hr before applying to the cells. After a 48 hr incubation with the E6-aerolysin fusion, the cells were stained with MTS for 3 hr and percentage of live cells calculated.

FIG. 11A is a graph showing thermostability analysis results on CD5 binding E6 protein. The percentages of E6 protein that remained soluble after heating for 30 min. at each temperature are shown.

FIG. 11B is a graph showing thermostability analysis results on E6-aerolysin fusion protein. The percentages of the fusion protein that remained soluble after heating for 30 min. at each temperature are shown.

FIG. 12A shows the mutated human thioredoxin sequence (SEQ ID NO:220) that was used as template for generating loop diversified protein libraries; mutations are highlighted by underlined amino acids. The loops are indicated by arches across the peptide sequences. For loop diversifications the grey shaded amino acids, 4 in loop 1, 4 in loop3, 6 in loop3', and 4 in loop5, are replaced with random peptide sequences as indicated in FIG. 12B.

FIG. 12B is a schematic presentation of three loop-diversified libraries, TRX-L1, TRX-L2, and TRX-L3. The differences among them are around loop 1, where different numbers/variations of amino acids are used to replace the active site amino acids $^{32}$SGPS$^{35}$ (SEQ ID NO:4). All three libraries contain the same additional loop diversifications in loop3, loop3' (residues common to SEQ ID NOs:225-227), and loop5, as indicated here and in FIG. 12A.

Figure 13:
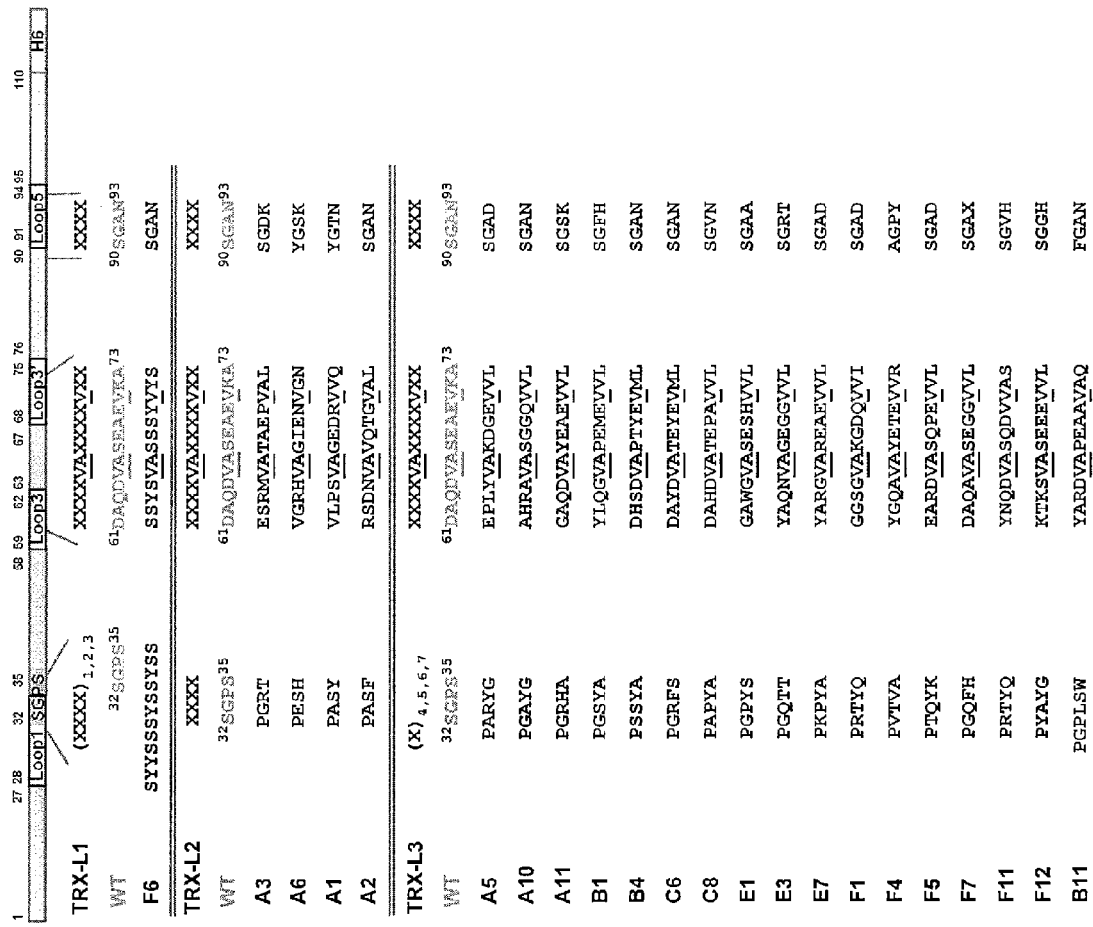

FIG. 13 shows the EpCAM binding clones selected by phage display using TRX-L1 (SEQ ID NO:225), TRX-L2 (SEQ ID NO:226), and TRX-L3 (SEQ ID NO:227), respectively. The selected sequences are aligned with the template sequence from human thioredoxin (residues a-b, c-d, and e-f of SEQ ID NO:169). Clones shown include F6 (SEQ ID NO:228), A3 (SEQ ID NO:229), A6 (SEQ ID NO:230), A1 (SEQ ID NO:231), A2 (SEQ ID NO:232), A5 (SEQ ID NO:233), A10 (SEQ ID NO:234), A11 (SEQ ID NO:235), B1 (SEQ ID NO:236), B4 (SEQ ID NO:237), C6 (SEQ ID NO:238), C8 (SEQ ID NO:239), E1 (SEQ ID NO:240), E3 (SEQ ID NO:241), E7 (SEQ ID NO:242), F1 (SEQ ID NO:243), F4 (SEQ ID NO:244), F5 (SEQ ID NO:245), F7 (SEQ ID NO:246), F11 (SEQ ID NO:247), F12 (SEQ ID NO:248), and B11 (SEQ ID NO:249).

Figure 14:
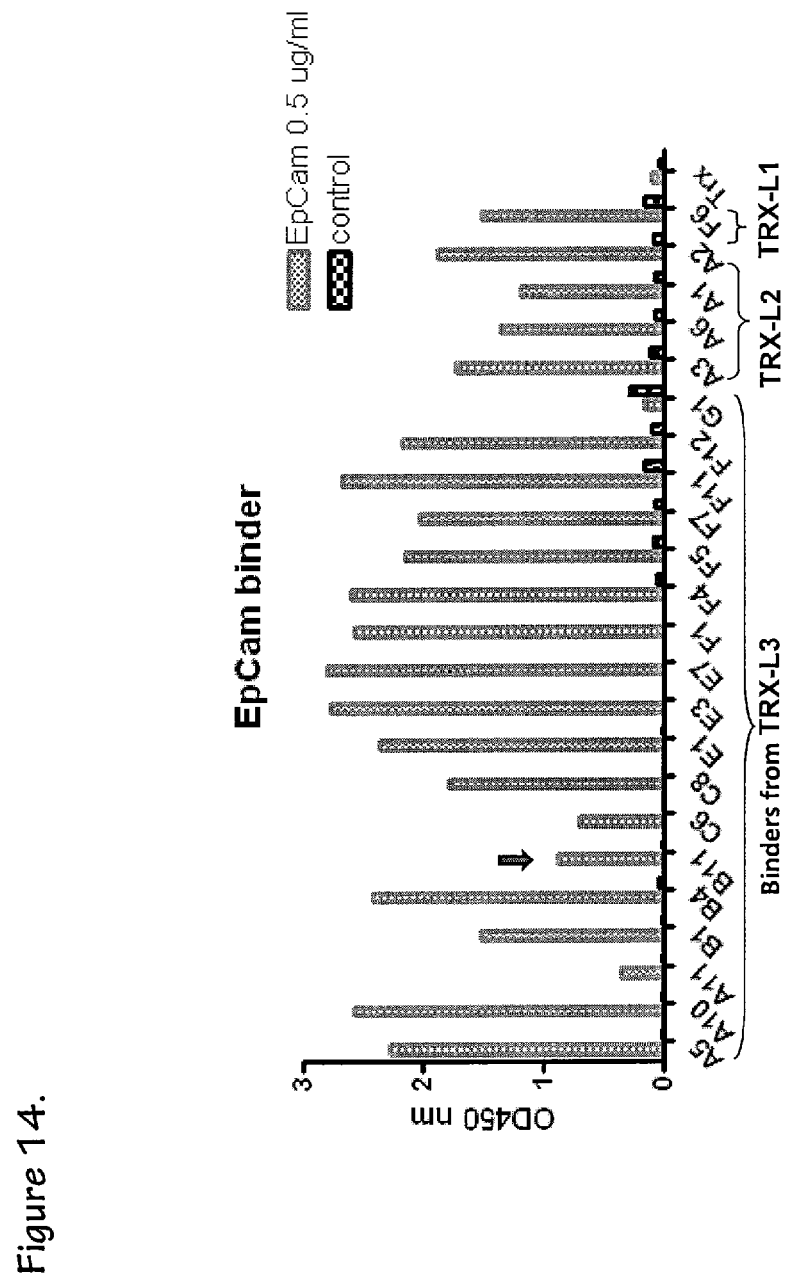

FIG. 14 is a graph showing the phage ELISA assay of EpCAM-Fc and BSA (control) binding with phages that display the selected, discrete EpCAM binders from libraries TRX-L1, TRX-L2, TRX-L3.

Figure 15:
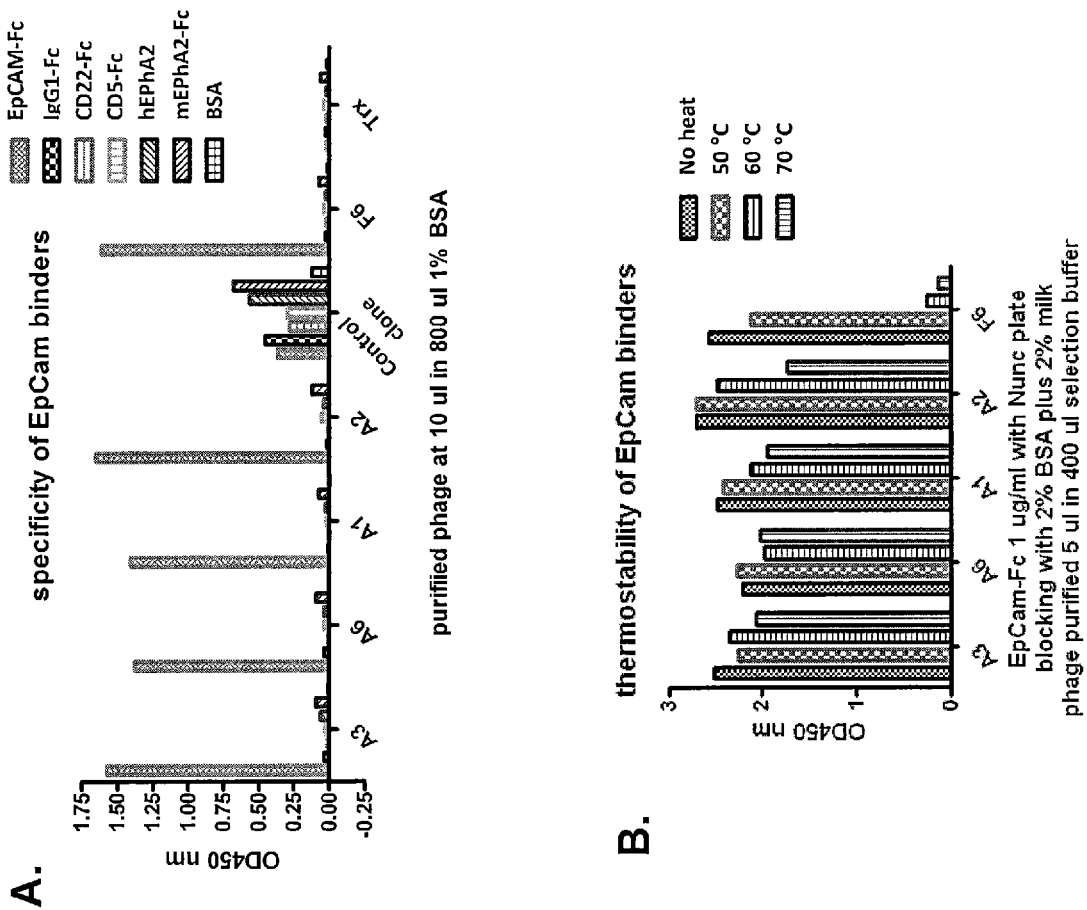

FIG. 15A is a graph showing the phage ELISA assay results with phages that display the selected, discrete EpCAM binders from libraries TRX-L1 and TRX-L2. The following proteins were immobilized on wells of nunc plates and reacted with phage: EpCAM-Fc, IgG1-Fc, CD22-Fc, CD5-Fc, hEphA2, mEphA2-Fc, BSA. Bound phage was detected with an anti-M13 pVlll antibody conjugated to HRP.

FIG. 15B is a graph showing the phage ELISA assays of EpCAM-Fc binding after the phages were heated at indicated temperatures for 10 min. The clones from the TRX-L2 library are more stable than those selected from the TRX-L1 library.

FIG. 16 shows a summary on phage display selection of mutated TRX proteins from the TRX-3 library for specific binders to various protein targets, including CD3ε, CD5, CD19, CD22, EpCAM, LGR5, and HSA. An example of the selected sequences for each target from randomized loop 1 (SEQ ID NO:250), including the SGPS (SEQ ID NO:4) active site, and loop3' (SEQ ID NO:251) are shown, demonstrating the large variability of the sequences selected for the divergent protein targets. Representative binders shown include C4 (SEQ ID NOs:45 and 46), E6 (SEQ ID NOs:39 and 40), A1 (SEQ ID NOs:53 and 54), A4 (SEQ ID NOs:56 and 57), A6 (SEQ ID NOs:62 and 63), D2 (SEQ ID NOs:111 and 112), and E2 (SEQ ID NOs:119 and 120).

FIG. 17 shows a summary of phage display selection of mutated TRX proteins that bind specifically to human serum albumin. The alignment of selected loop 1 and loop3' sequences with that of wild type TRX (SEQ ID NO:252) at corresponding sites revealed two sets of loop3' motifs specific for HSA binding, i.e., the F-rich motif (FXXFXFPXX; residues 10-18 of SEQ ID NO:6) and the AGPF motif (LXAGPFXXX; residues 10-18 of SEQ ID NO:7). Clones shown include A11 (SEQ ID NOs:253 and 254), C6 (SEQ ID NOs: 115 and 116), E1 (SEQ ID NOs:117 and 118), E2 (SEQ ID NOs:119 and 120), E5 (SEQ ID NOs:121 and 122), F3 (SEQ ID NOs:123 and 124), G5 (SEQ ID NOs:125 and 126), and H6 (SEQ ID NOs:127 and 128).

Figure 18:
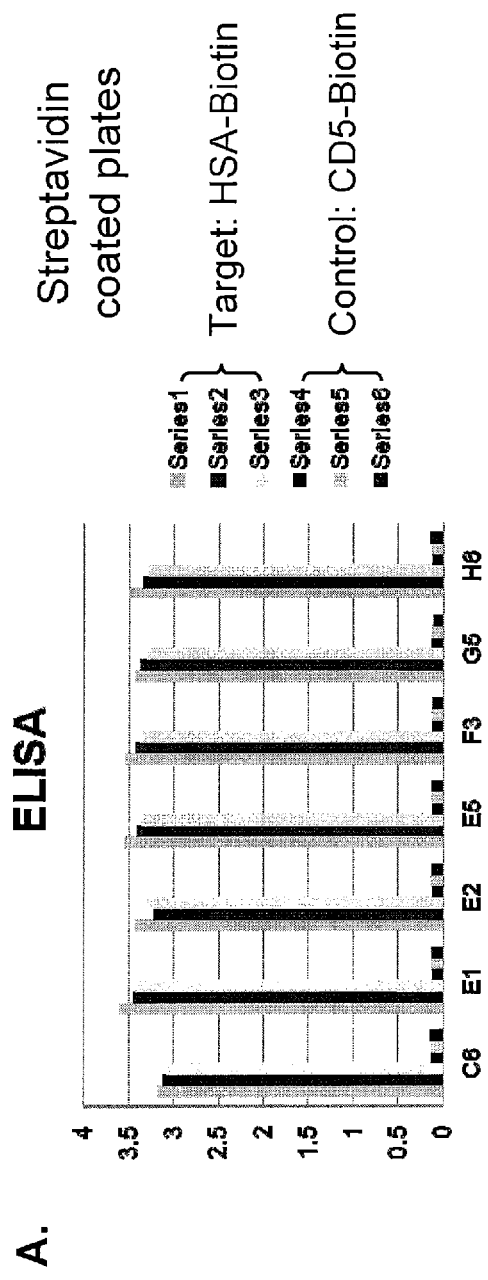
Figure 18:
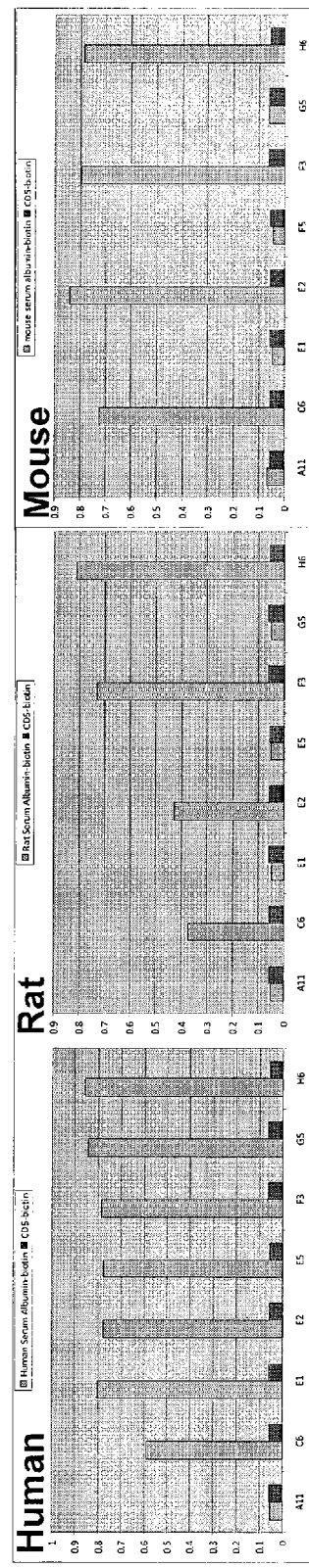

FIG. 18A is a graph depicting phage ELISA results of phage selected HSA binders listed in FIG. 17. The ELISA experiments were performed in triplets on 96-well streptavidin coated plates immobilized with either HSA-biotin or CD5-biotin. The phage display selected clones only showed strong binding to HSA, demonstrating target specificity of these TRX-based binders.

FIG. 18B shows bar graphs depicting phage ELISA assay results using human, rat, and mouse serum albumin as target proteins. The ELISA experiments were performed on 96-well streptavidin coated plates, immobilized with HSA-biotin, RSA-biotin, and MSA-biotin, respectively. The selected clones described in FIG. 17 were tested and showed Loop3' motif dependent affinity to RSA and MSA.

FIG. 18C summarizes the ELISA results of the phage selected HSA binders. The binders comprising an F-rich motif in loop3' are capable of binding to all three different serum albumins. The binders comprising an AGPF motif (residues 10-18 of SEQ ID NO:7) in loop3' or a unique loop3' sequence of VYVSLSRHR (SEQ ID NO:126) only showed significant affinity for HSA, not to RSA or MSA.

Figure 19:
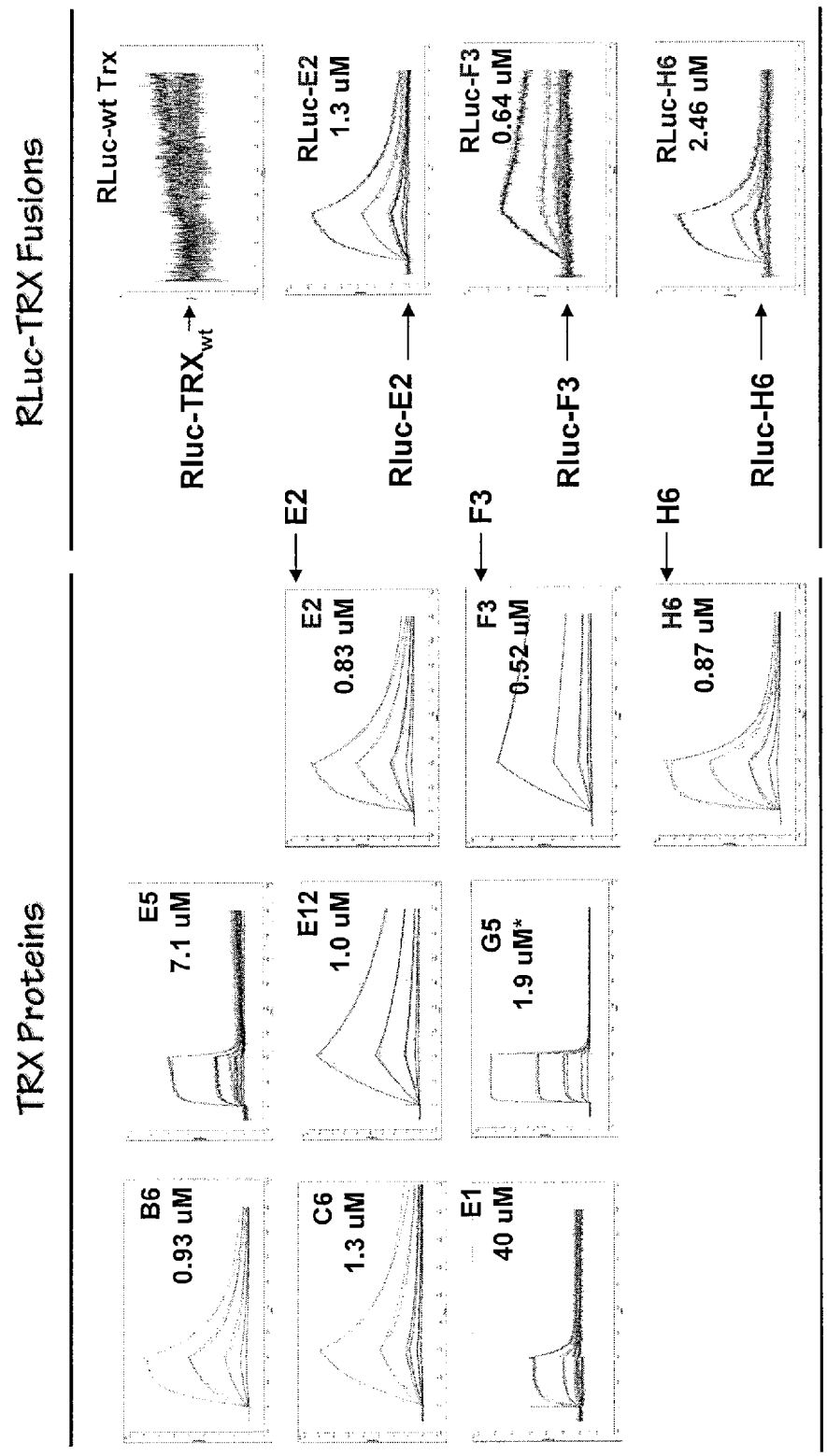

FIG. 19 shows the surface plasmon resonance (SPR) sensorgrams depicting the interactions between HSA and several selected HSA binding mutant TRX proteins (left panel) and their fusion with Renilla Luciferase (right panel). The mutant TRX proteins E2, F3, and H6 (all with F-rich loop3') showed slightly higher affinity to HSA (sub uMs) than the corresponding N-terminus fusion proteins with Renilla Luciferase RLuc-E2, RLuc-F3, and RLuc-H6 (sub to low uMs). The fusion protein of wild type TRX with RLuc (RLuc-TRX$_{wt}$) did not exhibit strong binding to HSA.

Figure 20:
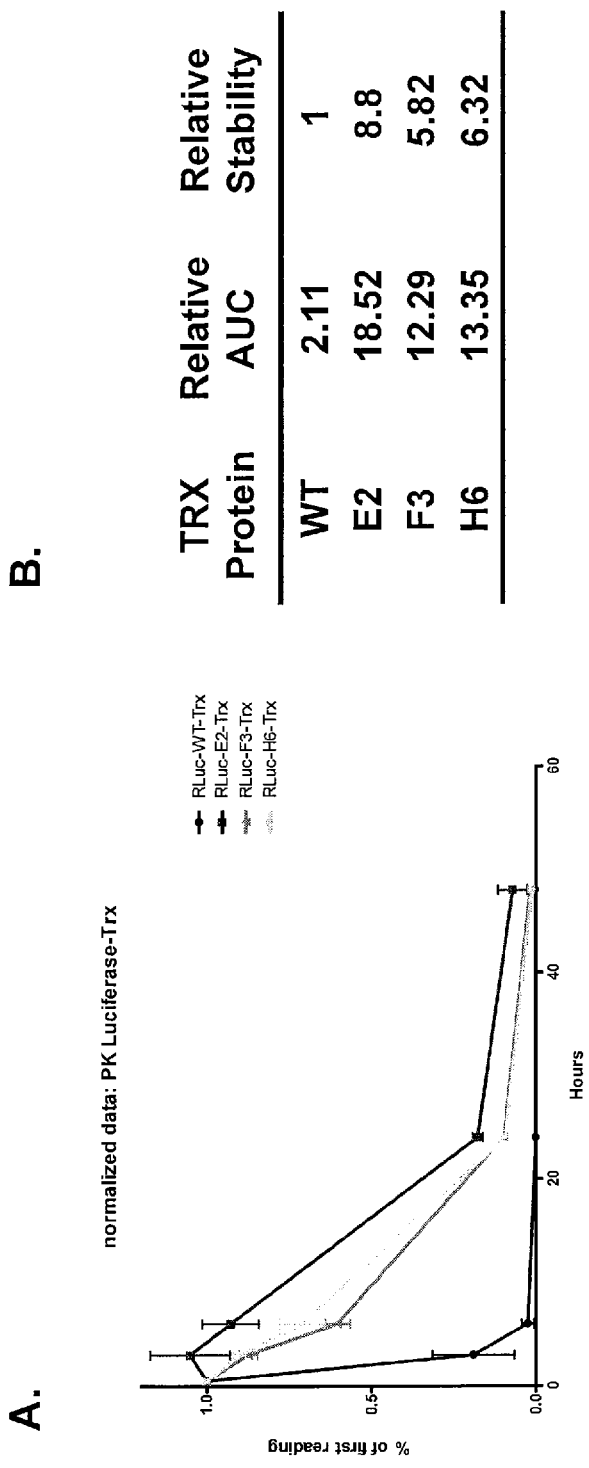

FIG. 20A shows the time courses of four RLuc-TRX fusion proteins after intravascular injection into individual mice. The amount of RLuc-E2, RLuc-F3, and RLuc-H6 fusion proteins in plasma decreased significantly slower compared with Rluc-TRX$_{wt}$.

FIG. 20B shows the pharmarcokinetic (PK) data obtained from FIG. 20A. The relative area under the curve (AUC) suggests that all the HSA binding mutant RLuc-TRX fusions possess superior plasma stability to RLuc-TRX$_{wt}$. The RLuc-E2 mutant is 8.8-fold more stable than RLuc-TRX$_{wt}$, demonstrating the capability of E2 to prolong the half-life of the parent fusion protein to that extent.

DETAILED DESCRIPTION OF THE INVENTION

The present invention provides compositions based on thioredoxin-like fold protein domains, described herein as engineered thioredoxin-like fold proteins (ETRXs). These proteins comprise one or more artificially diversified thioredoxin-like fold protein domains; each domain may be originated from the same or different thioredoxin-like fold protein domains. Of particular interest are the ETRXs that have been derived by substitution of two or more loops of a naturally occurring thioredoxin-like fold sequence. These loop-diversified ETRXs may contain additional sequence variations, for example improving affinity, stability, selectivity, or solubility, that have been introduced at any location in the molecule. In addition, an ETRX may be optionally substituted with prosthetic groups, polymers, proteins, nucleic acids, carbohydrates, metals, or natural or synthetic small molecules and toxins.

Figure 1:
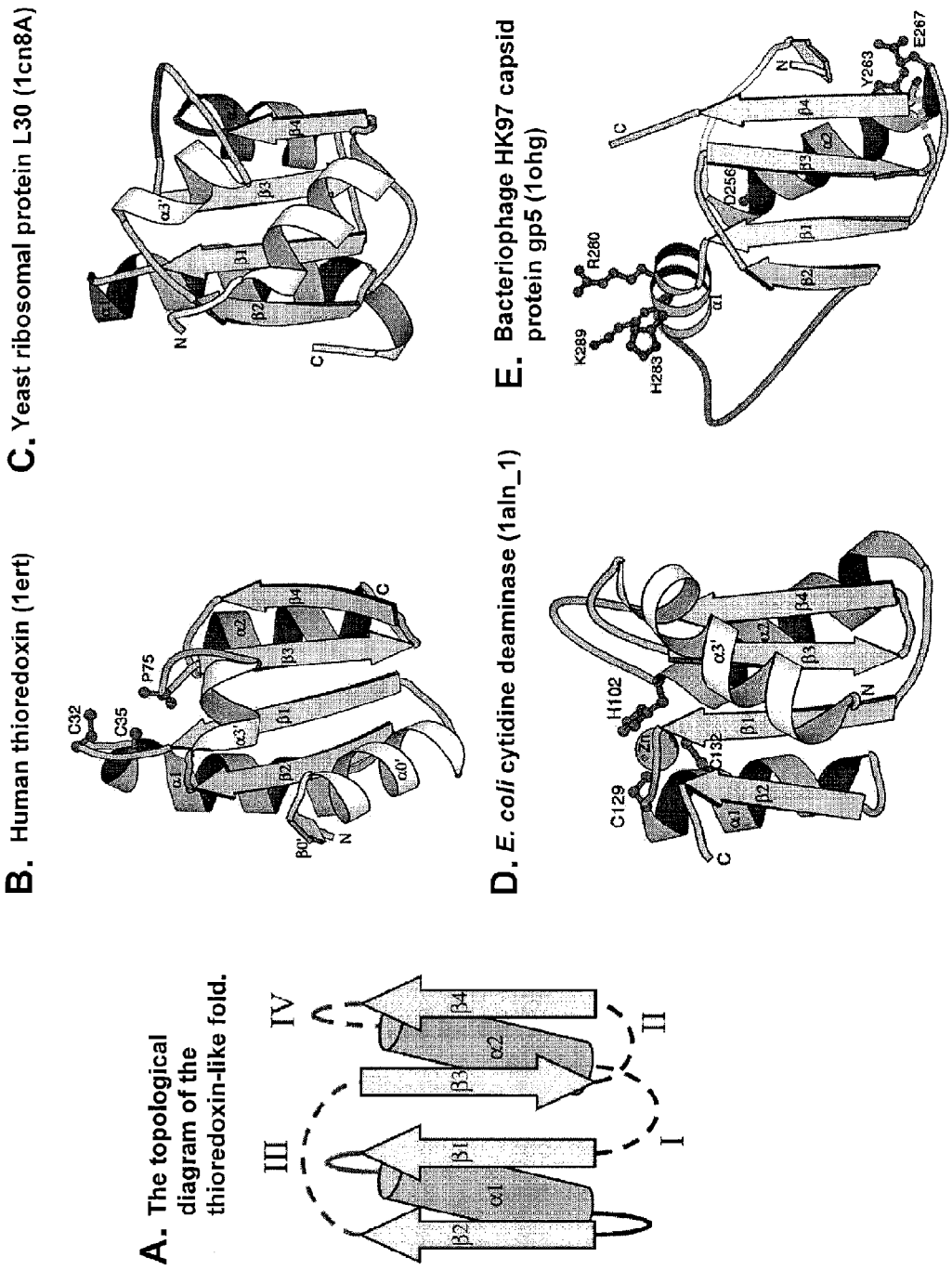

723 protein domains that may be grouped into eleven evolutionary families have been identified to date with a thioredoxin-like fold based on combined sequence, structural, and functional evidence (Qi and Grishin, *Proteins*, 2005, 58(2): 376-88). The protein domains that were unified into the thioredoxin-like fold group represent different circular permutations of the thioredoxin-like motif, which contains six secondary structural elements, i.e., four β-strands and two α-helices, compiled into a three-layer α/β/α sandwich (FIG. 1A). Amino acid sequences of representatives of the eleven evolutionary families are shown in FIG. 2, and the three-dimensional structures of four of these proteins are illustrated in FIGS. 1B-1E.

Figure 2:
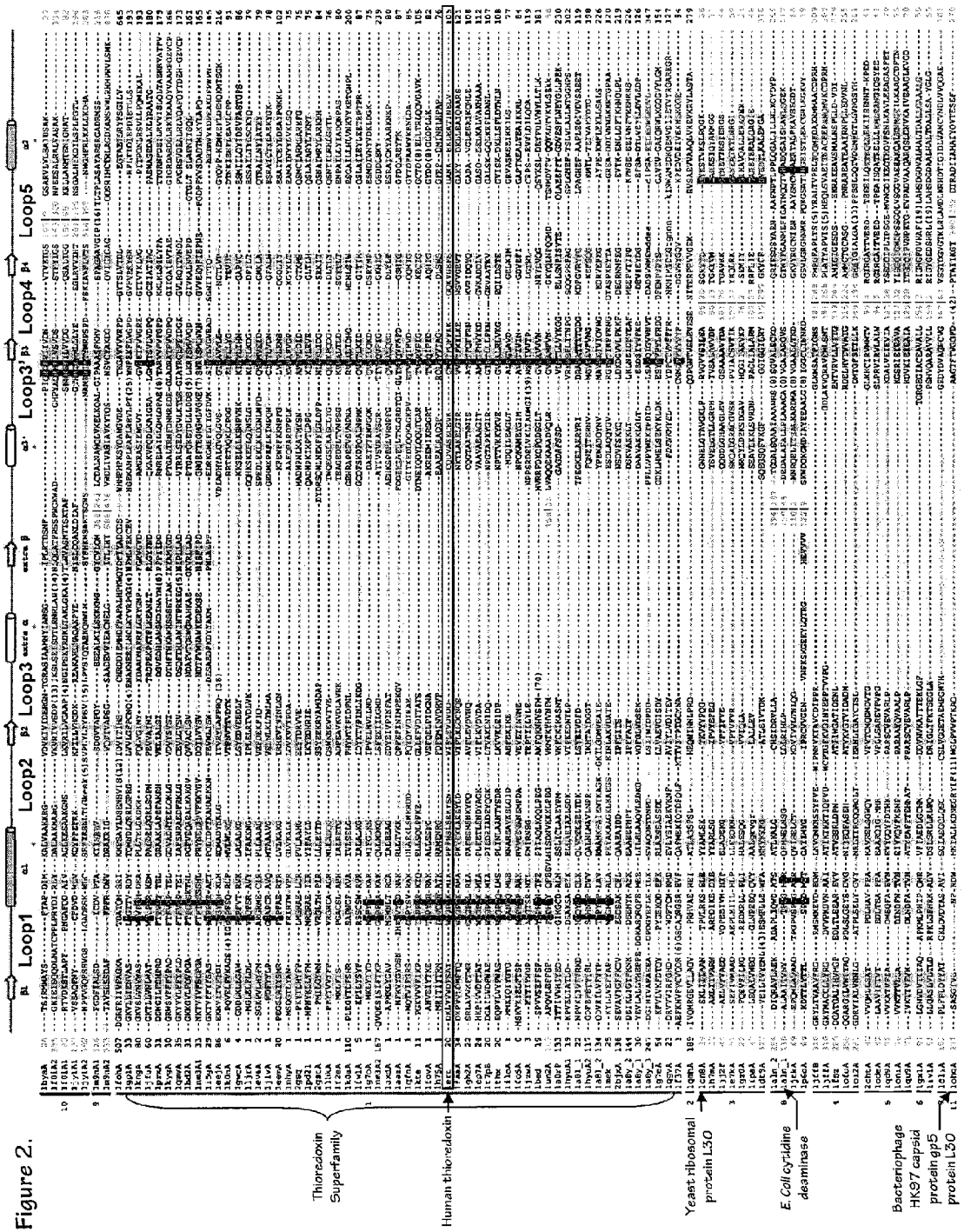

A structure-based multiple sequence alignment of 90 representative thioredoxin-like fold protein domains was manually constructed (FIG. 2, from Qi and Grishin, *Proteins*, 2005, 58(2):376-88). From this alignment, it is evident that some protein domains of the thioredoxin-like fold incorporate insertions of secondary structure elements into its common structural motif. Specifically, a number of proteins from four families possess the α-helix α3', and proteins from other four families have an extra αβ unit inserted between the β-strands β2 and β3. This demonstrates that the thioredoxin-like fold can easily accommodate exceedingly variable sequences between β2 and β3 (including loop3 and loop3'). Additional solvent exposed loops, including loop1, loop2, loop4, and loop5, are also highly tolerable to variations in loop length. Many members of the thioredoxin superfamily contain the conserved active-site motif CXXC (SEQ ID NO:5) that is located at the N-terminus of α-helix α1. In addition, a cis-proline residue located at the loop3' is conserved and is in spatial proximity to the CXXC (SEQ ID NO:5) motif.

Importantly, the length of the sequences corresponding to the CGPC (SEQ ID NO:3) motif of thioredoxin is highly conserved within the α1 α-helix in all of the thioredoxin-like fold protein domains, implying that any insertion of additional amino acids between the residues aligned with G33 and P34 may not be evolutionarily favored. This information provides an explanation for the observed severe destabilization to the *E. coli* thioredoxin caused by an insertion of 21 amino acid aptamer eIF4G-SG into its active site (Brown et al. *J. Mol. Biol.* 2010, 395(4):871-83). The loop diversification of the invention does not include the insertion of a peptide aptamer at this particular location (correspondingly between Gly33 and Pro34 of active site CGPC in thioredoxin) of the thioredoxin-like fold protein domains.

One preferred embodiment of the present invention is an ETRX comprising an engineered protein domain of the thioredoxin superfamily. FIG. 3 (obtained from NCBI's Conserved Domains Database) lists the protein subfamilies that belong to the thioredoxin super family (pfam cd01659).

A further preferred embodiment is an ETRX derived from a human thioredoxin-like fold domain of the thioredoxin superfamily. FIG. 4 shows the GI numbers of the human proteins, grouped in subfamilies, within the thioredoxin superfamily: 121672, 4467837, 13124748, 20810223, 33516901, 1B4Q_A, 6940947, 28193244, 1SJ6_A, 1WRY_A, 6010105, 31418324, 51464459, 1JHB, 5107031, 37537704, 37542493, 1EEM_A, 1GSE_B, 1IYI_D, 1XW5_B, 3LJR_B, 3PGT_B, 1KON_A, 1XWK_A, 3GTU_D, 5GSS_A, 3GSS_A, 1K3Y_B, 1TDI_A, 1FW1_A, 1LJR_B, 1RK4_B, 38257679, 56203088, 55961068, 119165, 38257738, 52632405, 57997510, 56789715, 2570009, 55962678, 20141285, 1AUC, 1ERT, 1GH2_A, 6840947, 20455529, 33340051, 31543836, 47606157, 1WOU_A, 1QGV_A, 1PQN_A, 51702156, 31542723, 50401164, 5430701, 27808673, 21706735, 23503035, 20454906, 24414114, 3882309, 1SEN_A, 29839560, 2507460, 24308127, 31077035, 47117631, 2501205, 54633317, 38505222, 20521894, 119530, 1208427, 30842594, 1203965, 30173124, 54633317, 28372543, 1208427, 119530, 2501208, 37182420, 24308127, 29839560, 49456295, 5453541, 66774045, 7705726, 55960250, 19923987, 33149331, 42476013, 1WPO_C 8134662, 33150834, 37183236, 46395720, 1QMV_A, 1PRX_A, 1OC3_B, 1H4O_H, 20455499, 2BJX_A, 1BJX, 119530, 21264492, 21757251, 37182195, 4557409, 55957226, 34531342, 2507461, 33150564, 21264492, 27502832, 37182195, 119530, 33149331, 4557549, 55957226, 34531342, and 2501205.

Another preferred embodiment is an ETRX comprising an engineered protein domain of the thioredoxin family (pfam cd02947). A further preferred embodiment is an ETRX comprising an engineered protein domain of the thioredoxin family from *Homo sapiens*, including proteins with the following GI numbers: 1AUC, 1ERT, 1GH2_A, 6840947, 20455529, and 33340051.

Table 1 shows the selected human thioredoxin fold protein domains from the thioredoxin superfamily that have been disclosed in the list U.S. Patent documents.

TABLE 1

Patent Disclosures on Human Proteins from TRX Superfamily

| | Protein Domains of the Thioredoxin Superfamily | | Patent Disclosures | |
|---|---|---|---|---|
| | | | On Protein & | On Targets & |
| GI | Domain Subfamily | Protein Name | Encoding DNA | Biomarkers |
| 4467837 | GSH Peroxidase | Glutathione peroxidase | | U.S. Pat. No. 6,753,314 |
| 20810223 | GSH Peroxidase | Glutathione peroxidase 8 | U.S. Pat. No. 6,984,519/ U.S. Pat. No. 7,368,531 | |
| 33516901 | GSH Peroxidase | Glutathione peroxidase 7 | U.S. Pat. No. 6,913,919/ U.S. Pat. No. 7,368,531 | |
| 1EEM_A | GST, N-terminal domain | Glutathione transferase (GST) | | U.S. Pat. No. 6,444,425/ U.S. Pat. No. 6,461,822/ U.S. Pat. No. 7,608,413 |
| 1IYI_D | GST, N-terminal domain | Hematopoietic prostaglandin D synthase | | U.S. Pat. No. 7,547,532 |
| 3PGT_B | GST, N-terminal domain | GST P1-1•S-hexylglutathione complex | | U.S. Pat. No. 5,968,737/ U.S. Pat. No. 7,521,195/ U.S. Pat. No. 7,601,505 |
| 5GSS_A | GST, N-terminal domain | GST P1-1•glutathione complex | | U.S. Pat. No. 7,521,195 |
| 1TDI_A | GST, N-terminal domain | GST A3-3•glutathione complex | | U.S. Pat. No. 6,812,339 |
| 52632405 | GST, N-terminal domain | Metaxin 1 | | U.S. Pat. No. 7,560,233 |
| 56789715 | GST, N-terminal domain | Metaxin 2 | U.S. Pat. No. 5,858,714 | |
| 20141285 | GST, N-terminal domain | Chloride intracellular channel protein 4 | | U.S. Pat. No. 7,608,413/ U.S. Pat. No. 7,691,599 |
| 1WOU_A | TRP14-Like | TRP14 | | U.S. Pat. No. 7,452,678 |
| 27808673 | PhD-Like | Phosducin-like protein | | U.S. Pat. No. 7,553,492 |
| 20454906 | UAS | FAS-associated factor 1 | | U.S. Pat. No. 7,560,233 |
| 24414114 | UAS | ETEA | | U.S. Pat. No. 7,411,051 |
| 5453541 | AGR | anterior gradient protein 2 homolog | U.S. Pat. No. 6,171,816/ U.S. Pat. No. 6,936,692/ U.S. Pat. No. 7,189,817 | U.S. Pat. No. 7,582,293 |
| 66774045 | AGR | anterior gradient protein 3 homolog | U.S. Pat. No. 6,171,816/ U.S. Pat. No. 7,129,324 | |
| 29839560(x3) | PDI-a-family | Thioredoxin domain-containing protein 5 | U.S. Pat. No. 6,916,648 | U.S. Pat. No. 7,608,413 |
| 2507460 | PDI-a-family | Protein disulfide-isomerase | | U.S. Pat. No. 7,473,531/ U.S. Pat. No. 7,521,195/ U.S. Pat. No. 7,638,238 |
| 31077035 | PDI-a-family | Endoplasmic reticulum resident protein 44 | U.S. Pat. No. 7,368,531 | |
| 47117631 | PDI-a-family | TRX-related transmembrane protein 1 | U.S. Pat. No. 6,635,468/ U.S. Pat. No. 6,994,857 | U.S. Pat. No. 7,473,531 |
| 30173124 | PDI-a-family | TRX-related transmembrane protein 4 | U.S. Pat. No. 6,916,648/ U.S. Pat. No. 7,129,338 | |
| 2501208(x3) | PDI-a-family | Protein disulfide-isomerase A5 | | U.S. Pat. No. 7,608,413 |
| 37182420 | PDI-a-family | Disulfide isomerase | U.S. Pat. No. 6,916,648/ U.S. Pat. No. 7,368,531 | |
| 7705726 | TMX-2 | TRX-related transmembrane protein 2 | U.S. Pat. No. 6,635,468 | |
| 42476013 | TlpA-like family | NHL repeat-containing protein 2 | U.S. Pat. No. 6,943,241 | |
| 33150834 | PRX-like2 | Unknown protein | | U.S. Pat. No. 7,625,699 |
| 37183236 | PRX-like2 | SFLQ611 | U.S. Pat. No. 6,913,919/ U.S. Pat. No. 7,060,479 | |
| 2501208 | PDI-b-family | Protein disulfide-isomerase A5 | | U.S. Pat. No. 7,608,413 |
| 31077035 | PDI-b-family | Endoplasmic reticulum resident protein 44 | U.S. Pat. No. 7,368,531 | |
| 21757251 | PDI-b-family | unnamed protein product | U.S. Pat. No. 7,193,069 | |
| 37182195 | PDI-b-family | EAAP781 | U.S. Pat. No. 6,936,436/ U.S. Pat. No. 6,979,557 | |
| 4557409(x2) or 119395727 | PDI-b-family | calsequestrin-2 precursor | | U.S. Pat. No. 7,345,142 |
| 2507461 | PDI-b-family | Protein disulfide-isomerase A3 | | U.S. Pat. No. 7,521,195/ U.S. Pat. No. 7,608,413 |
| 2507460 | PDI-b'-family | Protein disulfide-isomerase | | U.S. Pat. No. 7,473,531/ U.S. Pat. No. 7,521,195/ U.S. Pat. No. 7,608,413/ U.S. Pat. No. 7,638,288 |
| 37182195 | PDI-b'-family | EAAP781 | U.S. Pat. No. 6,936,436/ U.S. Pat. No. 6,979,557 | |
| 31077035 | PDI-b'-family | Endoplasmic reticulum resident protein 44 | U.S. Pat. No. 7,368,531 | |

Diversity in the loop regions of ETRXs is introduced through the incorporation of diversity in nucleic acids encoding ETRXs. For this purpose, random or indexed collections of nucleic acids encoding different sequences can be prepared according to any of several methods known in the art. Such collections can be prepared in ways that favor specific sequences or residues, or disfavor specific sequences or residues, by altering the probability of appearance of specific nucleotides in a site-specific or site-non-specific manner, or by specifying triplets of nucleic acid residues corresponding to individual codons and varying the relative abundance of said triplets in a site-specific or site-non-specific manner. For example, to reduce the abundance of cysteine residues, encoded in DNA by TGY, the relative abundance of T in the first position, G in the second position, or a pyrimidine (Y=C or T) in the third position, can be reduced in the template nucleic acid, illustrated here as DNA. Alternatively a mix of triplet precursors corresponding to each of the individual amino acids could be prepared, from which the triplets TGT and TGC are excluded. To reduce the frequency of termination codons, a common strategy is to randomize loops in the form $(NNS)_n$, where n denotes the number of random triplets to be included, N represents any nucleotide, and S represents C or G in the standard IUPAC nucleotide nomenclature. Since two of three stop codons (TGA and TAA) have an A in the third position, an NNS strategy is expected to reduce the frequency of stop codons from 3/64 to 1/32 compared to an NNN strategy.

The preparation of loop-diversified ETRXs may be carried out by any of several different schemes well known in the art. For example, libraries of ETRXs containing loop regions replaced by random peptide sequences of the same or different length can be prepared by recombinant DNA methods. Such libraries can be prepared as variants of a single scaffold having up to six loops diversified in a single ETRX or can be prepared as separate libraries each having one diversified loop per ETRX, or by some combination of loop-diversified libraries, for example having two diversified loops at one end and one at the other. Schemes in which individual libraries of loops are provided are often coupled with a facility for the interchange of the individual libraries, for example by the placement of restriction enzyme cleavage sites in the non-diversified regions that permit shuffling and reassembly of the library templates by restriction enzyme digestion and ligation. Other methods for shuffling of existing sequences are well-known in the art, and include recombination in vitro or in vivo, and nucleic acid shuffling and rejoining by PCR or isothermal amplification. In some cases it may be useful to create sub-libraries from existing libraries, or sub-libraries that incorporate some previously selected candidate ETRX as a starting point for the generation of further diversity focused on a particular ETRX with desirable properties. For example, to further improve the affinity of a pool of candidate ETRXs that shows a predominance of one loop sequence, a new library can be created in which that loop sequence is taken as the starting point and further randomization is introduced by partial or complete randomization of the other loops and/or by partial randomization of the predominant loop.

To retain proximity in sequence space to a favored sequence, many different strategies are known in the art. By way of example and without limitation, to diversify around the codon for methionine, ATG, and retain hydrophobic character, the template could be specified to contain at the first position 40% A and 20% of each other residue (C or G or T), at the second position 70% T and 10% of each other residue, and at the third position 75% of G and 25% C. Such a mixture would weight the substituted residues toward hydrophobic amino acids (which often contain a T in the second position), consistent with the hydrophobic character of methionine. The most likely encoded amino acid would be methionine itself. Depending on practical limitations for the preparation of the template nucleic acids, it may be more or less convenient to randomize each position in a manner specific for that residue, and in practice randomization schemes are frequently chosen that introduce an invariant probability of retaining one dominant residue and a fixed proportion of alternate residues, for example 70% A, 30% B for A, 70% C, 30% D for C, 70% G, 30% H for G and 70% T, 30% V for T. B, D, H and V are respectively the IUPAC codes for "not A"=C, G, or T, "not C"=A, G, or T, "not G"=A, C or T, and "not T (and not U)"=A, C or G.

The engineered thioredoxin-like fold proteins of the present invention are useful for the creation of binding proteins that adsorb with high affinity to selected targets. The potential uses of such binding proteins are broad, and include, without limitation, the analytical detection and measurement of molecules or complexes of molecules, the interruption or neutralization of cellular or humoral signaling events via the blockade of enzymes, receptors or ligands, the normalization of homeostatic balance by return of functionality compromised by age, disease, or trauma, the induction of receptor-mediated signaling by receptor agonism, the targeting of undesired cells for destruction, and the localization of binding targets, for example of tumors, microbes, thromboses, or sites of tissue damage. Targets of artificial binding proteins are often proteins or peptides but can also be carbohydrates, lipids, nucleic acids, small molecules such as drugs, metabolites, or toxins, or compositions formed from small molecules or inorganic species such as either natural or synthetic polymers, glasses, metals or alloys, semiconductors or insulators; targets can also comprise modifications or substitutions of proteins, carbohydrates, lipids, or nucleic acids, or combinations of one or more such agents, such as a carbohydrate-substituted proteins, carbohydrate-substituted lipid, RNA-protein complexes, etc. Methods for identifying binding proteins that display high-affinity and high specificity for their targets are known in the art.

One large set of preferred targets for ETRXs are human plasma proteins. For decades, biomedical researchers and clinicians have used plasma to isolate and measure proteins that can be useful for the diagnosis or monitoring of disease. In particular, the identification of protein biomarkers for the early diagnosis, suaneqatbtyping, and monitoring of treatment for chronic diseases, including cardiovascular diseases, cancer, arthritis, Alzheimer's disease, pulmonary disease, and autoimmune diseases, is now a central focus in clinical proteomics. The Healthy Human Individual's Integrated Plasma Proteome (HIP$^2$) database (Saha, S. et al., *BMC Med. Genomics* 2008, 1:12) has so far collected a set of 12,680 unique human plasma proteins using shotgun mass spectrometry analysis, the Swiss-Prot accession numbers of which downloaded from bio.informatics.iupui.edu/HIP2/ and is cited in Table S1 of U.S. Provisional Application No. 61/468, 836 as preferred targets, and specifically incorporated herein by reference.

A set of further preferred binding targets for ETRXs are Human Proteome Organization (HUPO) Plasma Proteome Project (PPP) core dataset of 3020 plasma proteins (Omenn, G. S., et al., *Proteomics,* 2005, 5(13):3226-45), which have been described to be comprised of a diverse group of proteins from the human proteome, including glycoproteins, DNA-binding proteins, coagulation pathway, cardiovascular, liver, inflammation, and monocular phagocyte proteins. A list of these 3020 plasma proteins with corresponding Uni-Prot accession numbers is available through BiomarkerDigger Database biomarkerdigger.org/frontpage.html, and is cited in Table S2 of U.S. Provisional Application No. 61/468,836, and specifically incorporated herein by reference.

Another collection of preferred targets for ETRXs comprises proteins of the main human peripheral blood constituents (Haudek, V. J. et al., *J. Proteome Res.* 2009, 8(8):3834-43). The identified proteins in T cells, monocytes, neutrophils, platelets, erythrocytes and plasma and PBMCs are sorted according to protein names and identified by their Swiss-Prot accession numbers cited in Table S3 of U.S. Provisional Application No. 61/468,836, and specifically incorporated herein by reference.

Cancer biomarkers found in plasma are preferred targets for ETRXs. The community of biomarker researchers has so far compiled from literature and other sources a list of 4531 proteins believed to represent a population of candidate plasma biomarkers that could be useful in early cancer detection and monitoring given sufficiently sensitive specific assays (Lee, B. T., et al. & Anderson, N. L., *Biomark. Insights*, 2008, 3:65-71). These preferred targets, annotated with gene names and entrez gene ID numbers, are cited in Table S4 of U.S. Provisional Application No. 61/468,836, and specifically incorporated herein by reference. An updated list is downloadable from CLUB ("Candidate List of yoUr Biomarkers"), a freely available, web-based resource (club.bii.a-star.edu.sg).

Human immunome proteins represent another set of preferred targets for ETRXs Immunome is a term that describes all the genes and proteins taking part in immune responses, and comprises CD (cluster of differentiation) proteins for cell surface molecules, as well as classical and alternative complement system, lectin pathway and the components of the membrane attack complex included together with chemokines, cytokines, and their receptors. These preferred targets are cited in Table S5 of U.S. Provisional Application No. 61/468,836, and specifically incorporated herein by reference, which contains 893 gene products with corresponding Swiss-Prot accession numbers and GeneBank ID numbers. An updated list is available from the Immunome Knowledge Base (IKB), a dedicated resource for immunological information (bioinf.uta.fi/IKB/).

Another set of preferred targets for ETRXs is the cell-surface proteins in the human immunome. Proteins located at the cell surface of immune cells are of particular relevance due not only to their participation in the network of interactions that regulate the immune response but also to their potential as excellent targets for diagnostic and therapeutic interventions. A comprehensive database of the human cell-surface proteins expressed in immune cells and lymphoid tissues was generated by integrating information collected from primary literature, databases and electronic information sources (Diaz-Ramos, M. C., et al. *Immunol. Lett.* 2010, published online November 2. PMID: 20932860). This manually curated database catalogues 1015 genes and proteins, includes the gene symbol and name of each protein, describes the family that each protein belongs to, indicates their type of extracellular domains, and compiles data regarding their expression. The database is cited in Table S6 of U.S. Provisional Application No. 61/468,836, and specifically incorporated herein by reference.

Therapeutic targets that have been established by research, development, and clinical applications are also the preferred targets of ETRXs. The proven efficacy of drugs interacting with these targets, either clinically or experimentally, suggests that ETRXs binders to such targets are potential candidate agents to elicit therapeutic responses.

DrugBank (Wishart, D. S., et al. *Nucleic Acids Res.* 2008, 36(Database issue):D901-6) is a richly annotated resource that combines detailed drug data with comprehensive drug target and drug action information, in which both FDA-approved small molecule and biotech drugs and experimental drugs are included. These drugs are linked to more than 2500 non-redundant protein or drug target sequences, comprising the "All Drug Targets" list of target proteins cited in Table S7 of U.S. Provisional Application No. 61/468,836, and specifically incorporated herein by reference. The protein targets include approved drug targets, small molecule drug targets, nutraceutical drug targets, experimental drug targets, withdrawn drug targets, biotech drug targets, and illicit drug targets, and are available for download from DrugBank (drugbank.ca/downloads).

MATADOR (Manually Annotated Targets and Drugs Online Resource) is a resource for protein-chemical interactions. It differs from other resources in its inclusion of as many direct and indirect interactions (Günther. S. et al. *Nucleic Acids Res.* 2008, 36(Database issue):D919-22). MATADOR contains 2901 protein targets, which are cited in Table S8 of U.S. Provisional Application No. 61/468,836, and specifically incorporated herein by reference, and included as additional preferred targets of ETRXs.

Therapeutic Target Database (TTD) has been developed to provide information about therapeutic targets and corresponding drugs (Zhu, F., et al. *Nucleic Acids Res.* 2010, 38(Database issue):D787-91). This database currently contains 1906 targets, including 358 successful, 251 clinical trial, 43 discontinued and 1254 research targets, and 5124 drugs. The protein sequences of these targets are available for download at bidd.nus.edu.sg/group/cjttd/TTD_Download.asp, which are cited in Table S9 of U.S. Provisional Application No. 61/468,836, and specifically incorporated herein by reference, and included as further preferred targets of ETRXs.

Yet another set of preferred targets for ETRXs are cancer cell surface markers. It has been demonstrated that in many types of cancer, some surface antigens are significantly upregulated in cancerous cells in comparison to normal cells. These differentiated expressions offer opportunities for selective binding of ETRXs to cancer cells for detection or destruction. Listed in Table 2 are some of the examples of these potential targets.

Cancer stem cell surface markers are further preferred targets for ETRXs. Cancer stem cells may have direct therapeutic relevance due to resistance to current treatment paradigms, suggesting novel multimodal therapies targeting the cancer stem cells may improve patient outcomes. Listed in Table 3 are examples of protein targets related to cancer stem cells reported in literature to date.

TABLE 2

Cancer Cell Surface Antigen Targets

| Type of Cancer | Surface Antigen | UniProt Accession | Normal Distribution | Overexpression in Cancer |
|---|---|---|---|---|
| Breast Cancer | Claudin-3 & Claudin-4 | O15551 & O14493 | Tight junctions at the apical junctional complex in epithelial and endothelial cellular sheets; gut, lungs, and kidneys | Expression in 92-100% of breast carcinomas, claudin-3 and -4 overexpressed in 62% or 26% of breast carcinomas, respectively |
| | MUC1 (Mucin 1) | P15941 | Expressed at the luminal surface of most simple epithelial cells | Expression in ~90% breast carcinomas; correlates with lower grade tumors |
| | EpCAM (Epithelial cell adhesion molecule) | P16422 | Expressed on the baso-lateral cell surface in most human simple epithelia | Upregulated in ~35% breast carcinomas, and by Taxol or Navelbine; IHC positive in 74% samples; >100-fold increase in mRNA; correlates w/ poor prognosis |
| | EphA2 (Ephrin receptor A2) | P29317 | Weak or negative IHC in normal breast tissues | Overexpressed in ~92% of breast tumor cells (by IHC, diffused into cytoplasm); certain epitopes more exposed than in normal cells |
| | HER2 | P04626 | Liver, kidneys, spleen, etc. Br J Pharmacol. 2004, 143(1): 99 | Upregulated in ~20-30% breast cancer; correlates w/ poor prognosis; only partially overlaps with EpCAM overexpression |
| | EGFR (Epidermal growth factor receptor) | P00533 | Kidneys, liver, intestine, bone, etc. J Nucl Med. 2006, 47(6): 1023 | Only positive in ~10% breast cancer tissue; involved in GPR30/EEFR signaling pathway in triple negative breast caner |
| | CEA (Carcino-embryonic antigen) | P06731 | Limited tissue distribution: colon, neck, stomach, toque, esophagus, cervix, prostate | Overexpressed in gastro-intestinal, breast, & lung cancers; upregulated by drugs; also a serum marker; detected in only 19% of breast cancers |
| | uPAR | Q03405 | Low expression in normal breast tissue | Overexpressed by leukemias and breast cancer |
| | CD24 (aka HSA: Heat stable antigen) | P25063 | B cells, granulocytes | High IHC staining in 85% breast cancer |
| | STEAP1 (Six-trans-membrane epithelial antigen of the prostate) | Q9UHE8 | Predominantly in prostate; some presence in bladder; low level in colon, pancreas, stomach, and uterus | Overexpressed in prostate cancer and breast cancer |
| | CSPG4 (chondroitin sulfate proteoglycan 4) | Q6UVK1 | Restricted distribution in normal tissues | High expression in >80% melanoma lesions; preferentially expressed in ~73% triple negative breast cancer tissues |
| | CD73 | P21589 | Normally expressed on endothelial cells and subsets of hematopoietic cells | Expression in bladder cancer, leukemia, glioma, glioblastoma, melanoma, ovarian cancer, thyroid cancer, esophageal cancer, prostate cancer, and breast cancer; associated with a prometastatic phenotype in melanoma and breast cancer |
| | MUC4 | Q99102 | Widely expressed, being present on the ocular surface as well as apical epithelial surfaces of the respiratory tract, specific regions of the gastrointestinal tract, and both female and male reproductive tracts | Overexpressed in breast tumors and could mask Her2 on breast cancer cell surface |
| | MMP-11 (stromelysin-3) | P24347 | Expressed in various tissue remodeling processes, both normal and pathological. | Over-expressed in the majority of human carcinomas; over-expressed in more than 90% of invasive breast carcinomas |
| | MMP-7 (matrilysin) | P09237 | Constitutively expressed by many epithelial cell types, often ductal epithelium of adult exocrine glands in skin, salivary glands, pancreas, liver, and breast, and by glandular epithelium of the intestine and reproductive organs | Overexpressed in invasive cancers of the digestive organs, such as the esophagus, stomach, colon, liver, and pancreas. Also overexpressed in lung, skin, breast, prostate, and head and neck. Associated with advanced clinicopathological stages and unfavorable prognosis |

TABLE 2-continued

Cancer Cell Surface Antigen Targets

| Type of Cancer | Surface Antigen | UniProt Accession | Normal Distribution | Overexpression in Cancer |
|---|---|---|---|---|
| | GPR30 (G-protein-coupled receptor-30) | Q99527 | Expressed in a variety of tissues, including the central nervous system. | The plasma membrane bound GPR30 is associated with breast tumor metastasis and transactivation of the EGFR. |
| | CXCR4 | P61073 | A Marker of Normal and Malignant Stem Cells | More frequently expressed in breast compared to other metastatic adenocarcinomas in effusions |
| | CD44s & CD44v6 | P16070 | Not expressed in normal breast tissue | Expressed in intraductal carcinoma of breast; associated with lymph node metastases and invasion |
| | p-Glyco-protein (MDR1 gene product) | P08183 | Low expression | Upregulated after chemotherapy |
| Colorectal Cancer | A33 antigen | Q99795 | Epithelia of gastrointestinal tract (colonic, small intestinal, and duodenal epithelium) | Carcinomas of the colon and rectum; a glycoprotein found in 95% CRC cancers |
| | EpCAM (Epithelial cell adhesion molecule) | P16422 | Expressed on the baso-lateral cell surface in most human simple epithelia | Upregulated in colon epithelia; upregulated by Taxol and Navelbine; IHC positive in 100% tissue samples |
| | EphA2 (Ephrin receptor A2) | P29317 | Some expression in normal colon tissue | Upregulated in 50-70% of primary colorectal tumor cells (IHC); downregulated in metastasis |
| | CEA (Carcino-embryonic antigen) | P06731 | Limited tissue distribution: colon, neck, stomach, tohue, esophagus, cervix, prostate | Overexpressed in many cancers, e.g., gastrointestinal, breast, and lung cancers. Can be further upregulated by drugs. Elevated levels in serum. |
| | CD15 (Sialyl lewis X) | N/A: tetrasaccharide carbohydrate | Neutrophils, eosinophiles, monocytes | Expressed in CRC, AML, and other cancers; correlated with EpCAM+ and CEA+ CRC cells: Proteomics. 2006, 6(6): 1791 |
| | CD166 (ALCAM: Activated leukocyte cell adhesion molecule) | Q13740 | Broad distribution, in epithelia, neurons, lymphoid and myeloid cells, hematopoietic and mesenchymal stem cells | Strong cell surface expression in 31% colorectal carcinoma; mRNA overexpression in 86% prostate carcinoma |
| | EGFR (Epidermal growth factor receptor) | P00533 | Kidneys, liver, intestine, bone, etc. J Nucl Med. 2006, 47(6): 1023 | Upregulated in cancers of colon, breast, etc. Level correlates with tumor progression |
| | HER2 | P04626 | Liver, kidneys, spleen, etc. Br J Pharmacol. 2004, 143(1): 99 | Upregulated in cancers of colon, breast, etc. |
| | MMP-11 (stromelysin-3) | P24347 | Expressed in various tissue remodeling processes, both normal and pathological. | Over-expressed in the majority of human carcinomas |
| | MMP-7 (matrilysin) | P09237 | Constitutively expressed by many epithelial cell types | Over-expressed in the majority of human carcinomas |
| | p-Glyco-protein (MDR1 gene product) | P08183 | Upregulated after chemotherapy | Drug-resistant cancer cells |
| Non-Small Cell Lung Cancer (NSCLC) | EphA2 (Ephrin receptor A2) | P29317 | Primarily found in adult epithelial cells | Overexpressed in ~74% (moderate-high) and detectable in 96% of NSCLC tissue (by IHC, in cytoplasm and membrane) |
| | CD24 (HSA: Heat stable antigen) | P25063 | B cells, granulocytes | ~40-60% of cancer tissue samples with high IHC staining; higher expression level corresponds to poor prognosis |
| | EpCAM (Epithelial cell adhesion molecule) | P16422 | Expressed on the baso-lateral cell surface in most human simple epithelia | IHC positive in 92% tissue samples |
| | HER2 | P04626 | Liver, kidneys, spleen, etc. Br J Pharmacol. 2004, 143(1): 99 | Overexpression in 16% and detection in 43% NSCLC tumor samples |
| | EGFR | P00533 | Kidneys, liver, intestine, bone, etc. J Nucl Med. 2006, 47(6): 1023 | Detection in 11-26% NSCLC tissue samples |
| | MSLN (Mesothelin) | Q13421 | Methothelial cells; Stomach, peritoneum, and ovary | Upregulated for >16-fold in pancreatic cancer tissues and cell lines; detected in 100% patients |

TABLE 2-continued

Cancer Cell Surface Antigen Targets

| Type of Cancer | Surface Antigen | UniProt Accession | Normal Distribution | Overexpression in Cancer |
|---|---|---|---|---|
| | MUC1 (Mucin 1) | P15941 | Expressed at the luminal surface of most simple epithelial cells | Highly expressed in lung cancer |
| | MUC4 | Q99102 | Widely expressed | Overexpressed in lung cancer tissues |
| | MAGE-A3 (melanoma-specific antigen A3) | P43357 | Restricted | exclusively presented on the cell surface of cancer cells and might be associated with an aggressive cancer phenotype |
| | CXCR2 | P25025 | Expressed on a variety of cell types and tissues | Upregulation correlated with tumorigenesis, cancer tissue angiogenesis, and metastasis of melanoma, lung, prostate, pancreatic, and ovarian cancers. |
| | MMP-11 (stromelysin-3) | P24347 | Expressed in various tissue remodeling processes, both normal and pathological. | Over-expressed in the majority of human carcinomas |
| | MMP-7 (matrilysin) | P09237 | Constitutively expressed by many epithelial cell types | Over-expressed in the majority of human carcinomas |
| | p-Glyco-protein (MDR1 gene product) | P08183 | Upregulated after chemotherapy | Drug-resistant cancer cells |
| Ovarian Cancer | Claudin-3 & Claudin-4 | O15551 & O14493 | Low claudin-3 in normal ovarian tissue | Claudin-3 upregulated in ovarian cancers for ~2-10 fold |
| | EpCAM (Epithelial cell adhesion molecule) | P16422 | Expressed on the baso-lateral cell surface in most human simple epithelia, very low expression in normal ovaries | Highly upregulated in ovarian cancer, breast cancer, etc; in 100% ovarian cancer tissue samples |
| | CD24 (aka HSA: Heat stable antigen) | P25063 | B cells, granulocytes | Highly upregulated mRNA in ovarian cancer; IHC positive in 75-91% ovarian tumors |
| | MUC1 (mucin 1) | P15941 | Expressed at the apical surface of most simple epithelia | IHC positive in 100% serous and 75% mucinous ovarian carcinomas; correlates with higher grade ovarian cancer |
| | MUC4 | Q99102 | Widely expressed | Overexpressed in ovarian tumors and has a role in the invasiveness of cancer cells |
| | MUC16 (CA125) | Q8WXI7 | Expressed on mesothelial cells in fetal coelomic epithelium and its derivatives in the fetus and the adult | Upregulated mRNA in 84% ovarian cancer tissues; but IHC equally positive for both normal & cancer tissues |
| | EphA2 (Ephrin receptor A2) | P29317 | Little to none IHC staining in normal ovarian tissue | Upregulated in ~76% of ovarianl tumor cells judging by IHC |
| | B7-H4 | Q7Z7D3 | Tightly controlled in normal tissues: no detection | Highly upregulated in 85-100% ovarian cancer tissue; a serum marker that seems to complement CA125 |
| | MSLN (Meso-thelin) | Q13421 | Methothelial cells; Stomach, peritoneum, and ovary | Upregulated in ovarian cancer methothelioma; upregulated in ~70% serous cancer |
| | HER2 | P04626 | Liver, kidneys, spleen, etc. | overexpressed/amplified in a range of tumor types including ovarian cancer |
| | CD157 | Q10588 | Expressed as surface antigen by stromal, myeloid, vascular endothelial and mesothelial cells | Detected in half of human primary ovarian cancers. Associated with more aggressive ovarian cancer |
| | EMP2 (epithelial membrane protein-2) | P54851 | Expressed at discrete locations in the body including high levels in the eye, lung, heart, thyroid, and uterus | Highly expressed in >70% of serous and endometrioid ovarian tumors compared with nonmalignant ovarian epithelium |
| | CXCR2 | P25025 | Expressed on a variety of cell types and tissues | Upregulation correlated with tumorigenesis and metastasis of melanoma, lung, prostate, pancreatic, and ovarian cancers. |
| | CXCR4 | P61073 | A marker of normal and malignant stem Cells | Expressed in 60-70% ovarian cancers |
| | uPAR | Q03405 | | Found in most primary, metastatic ovarian tumors. |
| | p-Glyco-protein (MDR1 gene product) | P08183 | Low expression | Upregulated after chemotherapy |
| Pancreatic Cancer | MSLN (Mesothelia) | Q13421 | Methothelial cells; Stomach, peritoneum, and ovary | Upregulated for >16-fold in pancreatic cancer tissues and cell lines; detected in 100% patients |

TABLE 2-continued

Cancer Cell Surface Antigen Targets

| Type of Cancer | Surface Antigen | UniProt Accession | Normal Distribution | Overexpression in Cancer |
|---|---|---|---|---|
| | PSCA (Prostate stem cell antigen) | O43653 | Prostate:kidney = 4084:152 per 10k actin mRNA | Upregulated for >16-fold in Pancreatic cell lines |
| | Claudin-4 | O14493 | Lung, breast, colon | mRNA upregulated for >32-fold in pancreatic cell lines; no IHC observation |
| | CD24 | P25063 | B cells, granulocytes | IHC positive in 72% pancreatic tumors |
| | EGFR | P00533 | Kidneys, liver, intestine, bone, etc. | Upregulated in ~31-68% pancreatic cancer patients |
| | HER2 | P04626 | Liver, kidneys, spleen, etc. | Upregulated in ~28% pancreatic cancer patients |
| | IGF-1 Receptor | P08069 | Broadly expressed during development | Implicated as playing key roles in the development, maintenance, and progression of cancer |
| | FAPP (Feto-acinar pancreatic protein) | O75612 | No expression in normal pancreas | Present at the cell surface of human pancreatic tumoral tissues |
| | MUC1 (Mucin 1) | P15941 | Expressed at the luminal surface of most simple epithelial cells | Expressed by >85% of invasive pancreatic adenocarcinomas |
| | MUC4 | Q99102 | Widely expressed | Overexpressed in pancreatic cancer; promotes tumorigenicity and directly involved in growth and survival of the pancreatic cancer cells |
| | CEA | P06731 | Limited tissue distribution: colon, neck, stomach, toque, esophagus, cervix, prostate | Elevated levels detected in the cell membrane of tumors derived from epithelium |
| | CEACAM6 | P40199 | Low expression in normal pancreas | 20- to 25-fold overexpression of CEACAM6 compared with normal pancreatic ductal epithelial cells |
| | Death Receptor 5 | O14763 | Low expression in normal pancreas | Frequently overexpressed in various cancers including pancreatic cancer |
| | CXCR2 | P25025 | Expressed on a variety of cell types and tissues | Upregulation correlated with tumorigenesis and metastasis of melanoma, lung, prostate, pancreatic, and ovarian cancers. |
| | TROP2 | P09758 | Normal epithelial tissues show little or no TROP2 expression | Overexpressed in 55% of pancreatic cancer patients and associated w/ poor survival. |
| | Integrin α6β4 | P23229 P16144 | Expressed only on the basal surface of ductal cells in normal pancreas and chronic pancreatitis | Dramatically overexpressed and displays altered localization including apical side during pancreatic cancer progression |
| | MDR1 gene product | P08183 | Low expression | Upregulated after chemotherapy |
| Prostate Cancer | PSMA (Prostate specific membrane antigen) | Q04609 | Prostate:liver:kidney = 174:14:11 per 10k actin mRNA; Strong IHC stain for 15/23 prostate, 22/22 kidney, & 11/18 bladder samples | Upregulated in higher grade Pca; Strong IHC stain for 8/19 prostate samples. (Apical localization) |
| | PSCA (Prostate stem cell antigen) | O43653 | Prostate:kidney = 4084:152 per 10k actin mRNA | Detected in 94% Pca samples and overexpressed in ~40% Pca; correlates with higher grade (Non-polarized distribution) |
| | STEAP1 (Six-trans-membrane epithelial antigen of the prostate) | Q9UHE8 | Predominantly in prostate; some presence in bladder; low level in colon, pancreas, stomach, and uterus | Overexpressed in prostate cancer (98% positive in Pca, 97% positive in BPH) and breast cancer |
| | EphA2 (Ephrin receptor A2) | P29317 | No normal prostate IHC staining | Overexpressed in ~93% of prostate cance samples by IHC (diffused into cytoplasm) |
| | EpCAM (Epithelial cell adhesion molecule) | P16422 | Expressed on the baso-lateral cell surface in most human simple epithelia, very low expression in normal ovaries | Highly upregulated in ovarian cancer, breast cancer, etc; increased in prostate cancer |

TABLE 2-continued

Cancer Cell Surface Antigen Targets

| Type of Cancer | Surface Antigen | UniProt Accession | Normal Distribution | Overexpression in Cancer |
|---|---|---|---|---|
| | ALCAM (Activated leukocyte cell adhesion molecule, CD166) | Q13740 | Broad distribution, in epithelia, neurons, lymphoid and myeloid cells, hematopoietic and mesenchymal stem cells | Strong cell surface expression in 31% colorectal carcinoma; mRNA overexpression in 86% prostate carcinoma |
| | EGFR | P00533 | Kidneys, liver, intestine, bone, etc. J Nucl Med. 2006, 47(6): 1023 | Upregulated in cancers of colon, breast, pancreas, etc. Mutated to EGFRvIII in Pca. |
| | HER2 | P04626 | Liver, kidneys, spleen, etc. Br J Pharmacol. 2004, 143(1): 99 | Upregulated in cancers of colon, breast, prostate, etc. |
| | p-Glyco-protein (MDR1 gene product) | P08183 | Low expression | Upregulated after chemotherapy |
| Ovarian Cancer | Claudin-3 Claudin-4 | | Tight junctions at the apical junctional complex in epithelial and endothelial cellular sheets; gut, lungs, and kidneys; low claudin-3 in normal ovarian tissue | Claudin-3 upregulated in ovarian cancers for ~2-10 fold | C-terminal domain of *C. perfringens* enterotoxin (C-CPE) can bind claudin-3 and -4 specifically |
| | EpCAM (Epithelial cell adhesion molecule) | | Expressed on the baso-lateral cell surface in most human simple epithelia, very low expression in normal ovaries | Highly upregulated in ovarian cancer, breast cancer, etc; in 100% ovarian cancer tissue samples | Cancer Immunol Immunother. 2001, 50(1): 51. Cancer Res. 1999 59(22): 5758 |
| | CD24 (aka HSA: Heat stable antagen) | | B cells, granulocytes | Highly upregulated mRNA in ovarian cancer; IHC positive in 75-91% ovarian tumors | Ricin A conjugate: Int J Cancer. 1996, 66(4): 526 |
| | MUC1 (mucin 1) | | Expressed at the apical surface of most simple epithelia | IHC positive in 100% serous and 75% mucinous ovarian carcinomas; correlates with higher grade ovarian cancer | Cancer Immunol Immunother. 1999, 48(1): 29 Mol Immunol. 2005, 42(1): 55 U.S. Pat. No. 6,506,881 Methods. 2005, 36(1): 43 |
| | EphA2 (Ephrin receptor A2) | | Little to none IHC staining in normal ovarian tissue | Upregulated in ~76% of ovarianl tumor cells judging by IHC | Mol. Immunol 2007, 44: 3049 |
| | B7-H4 | | Tightly controlled in normal tissues: no detection | Highly upregulated in 85-100% ovarian cancer tissue; a serum marker that seems to complement CA125 | N/A |
| | MSLN (Meso-thelin) | | Methothelial cells; Stomach, peritoneum, and ovary | Upregulated in ovarian cancer methothelioma; upregulated in ~70% serous cancer | J Mol Biol. 1998, 281(5): 917 Mol. Immunol. 1997, 34(1): 9 |
| | CXCR4 | | | Expressed in 60-70% ovarian cancers | U.S. Pat. No. 7,005,503 |
| | MUC16 | | Expressed on mesothelial cells in fetal coelomic epithelium and its derivatives in the fetus and the adult | Upregulated mRNA in 84% ovarian cancer tissues; but IHC equally positive for both normal & cancer tissues | Hybridoma 1997, 16(1): 47 |
| | p-Glyco-protein (MDR1 gene product) | | Low expression | Upregulated after chemotherapy | MRK-16: Biol Chem. 1999, 274(39): 27371 C219: J Biol Chem. 1997, 272(47): 29784 |
| Pancreatic Cancer | MSLN (Meso-thelin) | | Methothelial cells; Stomach, peritoneum, and ovary | Upregulated for >16-fold in pancreatic cancer tissues and cell lines; detected in 100% patients | J Mol Biol. 1998, 281(5): 917 Mol. Immunol. 1997, 34(1): 9 |
| | PSCA (Prostate stem cell antigen) | | Prostate:kidney = 4084:152 per 10k actin mRNA | Upregulated for >16-fold in Pancreatic cell lines | US06824780 |
| | Claudin4 | | Lung, breast, colon | mRNA upregulated for >32-fold in pancreatic cell lines; no IHC observation | C-terminal domain of *C. perfringens* enterotoxin (C-CPE) can bind specifically |

TABLE 2-continued

Cancer Cell Surface Antigen Targets

| Type of Cancer | Surface Antigen | UniProt Accession | Normal Distribution | Overexpression in Cancer |
|---|---|---|---|---|
| | CD24 | B cells, granulocytes | IHC positive in 72% pancreatic tumors | Ricin A conjugate: Int J Cancer. 1996, 66(4): 526 |
| | EGFR | Kidneys, liver, intestine, bone, etc. J Nucl Med. 2006, 47(6): 1023 | Upregulated in ~31-68% pancreatic cancer patients | Int J Cancer. 1995, 60: 137 Jpn J Cancer Res. 2000 91(10): 1035 |
| | HER2 | Liver, kidneys, spleen, etc. Br J Pharmacol. 2004, 143(1): 99 | Upregulated in ~28% pancreatic cancer patients | Biochemistry 1994, 33: 5451 J Mol Biol. 1996, 255(1): 28 |
| | p-Glyco-protein (MDR1 gene product) | Low expression | Upregulated after chemotherapy | MRK-16: Biol Chem. 1999, 274(39): 27371 C219: J Biol Chem. 1997, 272(47): 29784 |
| Prostate Cancer | PSMA (Prostate specific membrane antigen) | Prostate:liver:kidney = 174:14:11 per 10k actin mRNA; Strong IHC stain for 15/23 prostate, 22/22 kidney, & 11/18 bladder samples | Upregulated in higher grade Pca; Strong IHC stain for 8/19 prostate samples. (Apical localization) | US07045605 |
| | PSCA (Prostate stem cell antigen) | Prostate:kidney = 4084:152 per 10k actin mRNA | Detected in 94% Pca samples and overexpressed in ~40% Pca; correlates with higher grade (Non-polarized distribution) | US06824780 |
| | STEAP1 (Six-trans-membrane epithelial antigen of the prostate) | Predominantly in prostate; some presence in bladder; low level in colon, pancreas, stomach, and uterus | Overexpressed in prostate cancer (98% positive in Pca, 97% positive in BPH) | WO05113601A2 anti-STEAP-1 |
| | EphA2 (Ephrin receptor A2) | No normal prostate IHC staining | Overexpressed in ~93% of prostate cancer samples by IHC (diffused into cytoplasm) | Methods. 2005, 36(1): 43 Mol. Immunol 2007, 44: 3049 |
| | EpCAM (Epithelial cell adhesion molecule) | Expressed on the baso-lateral cell surface in most human simple epithelia, very low expression in normal ovaries | Highly upregulated in ovarian cancer, breast cancer, etc; increased in prostate cancer | Cancer Immunol Immunother. 2001, 50(1): 51. Cancer Res. 1999 59(22): 5758 |
| | ALCAM (Activated leukocyte cell adhesion molecule, CD166) | Broad distribution, in epithelia, neurons, lymphoid and myeloid cells, hematopoietic and mesenchymal stem cells | Strong cell surface expression in 31% colorectal carcinoma; mRNA overexpression in 86% prostate carcinoma | Reported in J. Cell Biol. 2005, 118(7): 1515 & Liu B., et al. J. Mol. Med. 2007, but sequences were not disclosed |
| | EGFR | Kidneys, liver, intestine, bone, etc. J Nucl Med. 2006, 47(6): 1023 | Upregulated in cancers of colon, breast, pancreas, etc. Mutated to EGFRvIII in Pca. | Int J Cancer. 1995, 60: 137 Jpn J Cancer Res. 2000 91(10): 1035 |
| | HER2 | Liver, kidneys, spleen, etc. Br J Pharmacol. 2004, 143(1): 99 | Upregulated in cancers of colon, breast, prostate, etc. | Biochemistry 1994, 33: 5451 J Mol Biol. 1996, 255(1): 28 |
| | p-Glyco-protein (MDR1 gene product) | Low expression | Upregulated after chemotherapy | Biol Chem. 1999, 274(39): 27371 J Biol Chem. 1997, 272(47): 29784 |

TABLE 3

Protein Targets Associated with Cancer Stem Cells

| | CSC Specific Markers | | Cell Growth Signaling Pathways | | Multi-Drug Efflux | UniProt |
|---|---|---|---|---|---|---|
| Type of Cancer | Cell Surface | Intracellular | Receptor | Ligand | Transporters | Accession |
| Acute myeloid leukemia (AML)[n] | CD34[b] CD123[b] | | | | | P28906 P26951 |

TABLE 3-continued

Protein Targets Associated with Cancer Stem Cells

| Type of Cancer | CSC Specific Markers | | Cell Growth Signaling Pathways | | Multi-Drug Efflux Transporters | UniProt Accession |
|---|---|---|---|---|---|---|
| | Cell Surface | Intracellular | Receptor | Ligand | | |
| | CD44 | | | | | P16070 |
| | CLL-1 | | | | | Q5QGZ9 |
| | CD96 | | | | | P40200 |
| | CD47 | | | | | Q08722 |
| | CD32 | | | | | P31995 |
| | CD25 | | | | | P01589 |
| | | ALDH1$^c$ | | | | P00352 |
| B-pre acute lymphocytic leukemia (ALL) | CD34$^b$ | | | | | P28906 |
| | CD38$^b$ | | | | | P28907 |
| | CD19$^b$ | | | | | P15391 |
| Bladder cancer | CD44$^d$ | | | | | P16070 |
| | CD47$^d$ | | | | | Q08722 |
| | | ALDH1$^d$ | | | | P00352 |
| Breast cancer | EpCAM$^a$ (CD326) | | | | | P16422 |
| | CD44$^b$ | | | | | P16070 |
| | | ALDH1$^c$ | | | | P00352 |
| | | | DLL4$^a$ | | | Q9NR61 |
| Brain cancer (Glioma) | CD133$^b$ | | | | | O43490 |
| | | | VEGFR$^a$ | | | P17948 |
| | | | | VEGF$^a$ | | P15692 |
| Chronic lymphocytic leukemia (CML) | CD200$^a$ | | | | | P41217 |
| | CD123$^a$ | | | | | P26951 |
| Colon cancer | EpCAM$^e$ | | | | | P16422 |
| | CD44$^e$ | | | | | P16070 |
| | CD133$^e$ | | | | | O43490 |
| | CD166$^e$ | | | | | Q13740 |
| | CD29$^e$ | | | | | P05556 |
| | CD24$^e$ | | | | | P25063 |
| | LGR5$^e$ | | | | | O75473 |
| | | ALDH1$^e$ | | | | P00352 |
| | | | CXCR4$^a$ | | | P61073 |
| | | | DLL4$^a$ | | | Q9NR61 |
| | | | Wnt-1$^a$ | | | P04628 |
| | | | | Frizzled$^a$ | | Q9UP38 |
| | | | | IL-4$^a$ | | P05112 |
| Head and neck cancer | CD44$^a$ | | | | | P16070 |
| | CD133$^l$ | | | | | O43490 |
| | | ALDH1$^{c,h}$ | | | | P00352 |
| Liver cancer (Hepatocellular carcinoma) | CD117$^f$ | | | | | P10721 |
| | CD133$^{a,b,f}$ | | | | | O43490 |
| | CD90$^{b,f}$ | | | | | P04216 |
| | CD44$^f$ | | | | | P16070 |
| | EpCAM$^f$ | | | | | P16422 |
| | | | PTEN$^f$ | | | P60484 |
| | | | | IL-6$^f$ | | P05231 |
| | | | | | MDR-1$^f$ | P08183 |
| | | | | | ABCG2$^f$ | Q9UNQ0 |
| | | | | | ABCC2$^f$ | Q92887 |
| Lung cancer | CD133$^{b,g}$ | | | | | O43490 |
| | EpCAM$^g$ | | | | | P16422 |
| | | ALDH1$^{g,h}$ | | | | P00352 |
| | | | CXCR4$^g$ | | | P61073 |
| | | | | | ABCG2$^g$ | Q9UNQ0 |
| Melanoma | CD20$^b$ | | | | | P11836 |
| | CD44$^a$ | | | | | P16070 |
| | CD133$^b$ | | | | | O43490 |
| | | | CXCR4$^a$ | | | P61073 |
| | | | | | MDR-1$^b$ | P08183 |
| | | | | | ABCB5$^b$ | Q2M3G0 |
| | | | | | ABCG2$^b$ | Q9UNQ0 |
| Ovarian cancer | CD24$^h$ | | | | | P25063 |
| | CD44$^b$ | | | | | P16070 |
| | CD117$^b$ | | | | | P10721 |
| | CD133$^{b,h}$ | | | | | O43490 |
| | | ALDH1$^{g,h}$ | | | | P00352 |
| | | | | | ABCG2 | Q9UNQ0 |
| Pancreatic cancer | CD24$^b$ | | | | | P25063 |
| | CD44$^b$ | | | | | P16070 |

TABLE 3-continued

Protein Targets Associated with Cancer Stem Cells

| Type of Cancer | CSC Specific Markers | | Cell Growth Signaling Pathways | | Multi-Drug Efflux Transporters | UniProt Accession |
|---|---|---|---|---|---|---|
| | Cell Surface | Intracellular | Receptor | Ligand | | |
| | CD133[b] | | | | | O43490 |
| | EpCAM[b] | | | | | P16422 |
| | | ALDH1[h] | | | | P00352 |
| | | | | | MDR-1[a] | P08183 |
| Prostate cancer | CD44[k] | | | | | P16070 |
| | CD133[h,k] | | | | | O43490 |
| | CD177[i] | | | | | Q8N6Q3 |
| | TROP-2[j] | | | | | P09758 |
| | | ALDH1[h] | | | | P00352 |
| | | | CXCR4[h] | | | P61073 |
| | | | | | ABCG2[i] | Q9UNQ0 |
| Renal cancer | CD105[b] | | | | | P17813 |
| | CD133[m] | | | | | O43490 |
| | | | CXCR4[m] | | | P61073 |

[a]Deonarain M. P. et al. *mAbs*, 2009,1(1): 12-26.
[b]Liu, H. G. & Zhang, X. H. *Asian Pac. J. Cancer Prev.* 2009, 10: 177-179.
[c]Alison, M. R., et al. *J. Pathol* 2010, 222: 335-344.
[d]Chan, K. S., et al. *Curr. Opin. Urol.* 2010, 20: 393-397.
[e]Todaro, M. et al. *Gastroenterol.* 2010, 138: 2151-2162.
[f]Lee, T. K. W. et al. *Liver Int.* 2009, 29(7): 955-965.
[g]Eramo, A. et al. *Oncogene*, 2010, 29: 4625-4635.
[h]Ma, I., & Allan, A. L., *Stem Cell Rev. Rep.* 2010, PMID: 21103958.
[i]Liu, T. et al. *Mol. Cell. Biochem.* 2010, 340(1-2): 265-73
[j]Trerotola, M. et al. *Am. J. Transl. Res.* 2010, 2(2): 135-144.
[k]Maitland, NJ, & Collins, A, T. *J. Clin. Oncol* 2008, 26(77): 2862-2870.
[l]Chen Z. G., *J. Oncol.* 2009, 2009: 894064.
[m]D'Alterio C., et al *Cell Cycle*, 2010, 9(22): 4492-4500.
[n]Majeti, R., *Oncogene*, 2010, PMID: 21076471.

ETRXs of the present invention can also be used to create novel activities, such as catalytic activity, or substrate activity, based on the incorporation of prosthetic groups or designed or randomly selected sequences that can be installed in the ETRX. For example, ETRXs can be used to generate substrates or inhibitors of proteases, or to provide proximity enrichment for substrates for enzymatic activities. In keeping with their utility as antibody equivalents, genetic selections or designed modifications that introduce catalytic potential can be incorporated into ETRXs through methods well known in the art, such as selection for affinity to a transition state analog of an intermediate that is found in a reaction to be facilitated by an ETRX.

To achieve high affinity and selectivity, ETRXs can be endowed with a novel surface complementary to a target of interest. For this purpose, random libraries of proteins can be created and screened for rare variants that have desired properties; alternatively, specific variants can be designed by computational analysis of the target binding surface and construction of a series of candidate binding proteins that may have the appropriate behavior. Random substitution schemes can be employed when the detailed molecular structure of the target is not known, or when the most appropriate site on a structurally well-characterized molecule cannot be determined in advance. Most contemporary scaffold diversification strategies are based on random substitution. The invention further provides for mixed computational and random strategies, for example in which random diversification leads to candidates that are further optimized by directed substitution, or the use of computational techniques to predict families of candidates that can be screened for an activity of interest.

Construction of Libraries and Designed Variants

Libraries of ETRXs can be prepared in various ways known to those skilled in the art. Disseminated random substitution, clustered substitution, and designed (targeted) alteration are strategies that have been employed to increase the affinity of a given diversified scaffold for a particular target protein. In general, the objective of such diversification is to increase affinity without compromising the overall stability or solubility of the protein. One of the most widely employed strategies is surface randomization, the replacement of endogenous sequences on one particular aspect or face of a protein in order to generate a highly diverse collection of surfaces. Two common subtypes of surface randomization are loop and pocket diversification, used for proteins that are naturally convex or concave respectively. Randomizations may conserve or alter the length if the scaffold is appropriately stable. In addition, the natural geometry of the scaffold may be altered by incorporation of structural elements that endow the randomized or grafted sequences with particular folds or shapes. Among the known elements that may be employed for such purposes are the placement of cysteine residues such that a disulfide-linked loop is formed, the introduction of helix or sheet-destabilizing residues, such as glycine or proline, the incorporation of beta turns or Trp cage motifs, or the formation of additional secondary structure elements, such as short alpha helical or beta strand sequences.

The affinity and stability of ETRXs with randomized surface loops can be further improved by the inclusion of mutations in the beta strands that improve rigidity or alter the positioning of the loops. Such favorable noncontact site mutations are well-known in the art and can be discovered by random mutagenesis once an initial candidate has been identified. Typically mutagenesis of the entire ETRX is performed, with selection for variants that exhibit higher binding affinity.

The engineered thioredoxin-like fold proteins of the present invention can be further adapted to include extensions/diversifications at their amino or carboxyl termini. The additional diversity may enhance affinity by providing secondary binding sites to the target, or may enhance the functional properties of the protein by binding to proteins with enhanced plasma half-life, or proteins that are known to be enriched in the vicinity of the target, or that afford the possibility of concentration in an organ or tissue-specific manner by binding to organ or tissue-specific secondary targets. When additional diversity elements are incorporated at the amino or carboxyl termini, measures may have to be employed to protect those elements from naturally occurring exopeptidases, such as the peptidyl peptidases, aminopeptidases, carboxypeptidases, and related enzymes. Methods of predicting and defeating susceptibility to exopeptidases are well known in the art. Methods of blocking exopeptidase activity include amino and carboxyl-terminal modification, incorporation of additional residues that are not substrates for the exopeptidases, or chemical modifications that destroy susceptibility.

The identification of a high-affinity, high selectivity ETRX can be achieved by either screening methods or selection methods. A screening method typically requires two elements: a supply of candidate ETRXs to be tested for affinity to the target; and a systematic method for the enumeration of the candidates, such as an ordered array or systematically composed mixture that can be convoluted to reveal the identity of the most active variants. Screening methods often require that large numbers of ETRXs be evaluated; in such cases it is common to use pooling schemes to mix candidates, allowing the presence or absence of a desired candidate to be determined with fewer measurements. Active pools are further subdivided to identify active unique species. Candidates derived from such screens can be subjected to further randomization and screening to progressively derive ETRXs of higher binding affinity.

Selection methods typically require a library of candidate ETRXs, each prepared in a form that provides a genetic linkage between the protein and a nucleic acid that encodes or identifies the protein. A mechanism must be provided to physically isolate and purify candidate binding proteins and their associated nucleic acids from the remaining library members that lack activity. In selection methods many fewer measurements are typically performed than in screening methods.

The present invention further provides methods for the identification of ETRXs having favorable affinity, selectivity, solubility, and thermal stability. Numerous selection methods for the enrichment of nucleic acids encoding proteins of interest that bind to a specific target are known in the art and are useful for the generation of the desired ETRXs. Among these are the so-called display technologies, including phage display, yeast display, bacterial display, viral display, mammalian cell display, ribosome display, RNA display, and DNA display. For the application of a particular form of display, an appropriate vector must be provided that is suitable for the display of the ETRX in the context in which selection is to take place. For example for commonly practiced forms of bacteriophage display, a plasmid encoding a translational fusion between a solvent-exposed phage structural protein and the ETRX must be created. For cellular display, such as bacterial, yeast or mammalian cell display, a fusion or stable association is created between a surface protein and the ETRX. For ribosome or mRNA display, a fusion or stable association must be created between the diversified binding protein and the mRNA that encodes it. For DNA display a fusion or stable association must be created between the ETRX and a high affinity, typically site-selective, DNA-binding protein. For some types of selection methods, physical association of the binding protein and the nucleic acid that encodes it is provided by physical compartmentalization. For example, in emulsion selection methods, a small aqueous droplet is provided in which the ETRX is synthesized from a template nucleic acid. In this case the physical association is provided by the compartmentalization afforded by the non-aqueous phase that separates the individual droplets.

Display-based selections consist of one or more cycles of enrichment, each of which comprises: (i) contacting the target of interest with a mixture of diversified proteins in display context, e.g. as phage particles, cells, or RNA fusions; (ii) physically separating those phage particles, cells or RNA fusions that bind the target from those that do not bind the target, or bind less avidly, and (iii) amplifying the resulting isolated binding population by in vivo or in vitro methods to generate a new, enriched collection of diversified proteins that can be subjected to additional rounds of contact and purification. For display-based selections it is a requirement that the target permit physical isolation of the complex of target and ETRX. For example, the target may be labeled with an antibody domain, peptide tag, fluorophore, biotin, or other affinity or labeling moiety, allowing the complex of ETRX and target to be physically separated from ETRXs that do not interact with the target.

Alternatively, antibodies or binding reagents specific for the target can be employed to effect separation. Often it is necessary to exclude unwanted ETRXs, for example those that bind to extraneous portions of the target, or to components of the apparatus used to effect physical separation. Common separation strategies rely upon an affinity matrix for the antibody domain, peptide tag, biotin, epitope or affinity moiety, such as a bead or magnetic particle bearing the cognate binding element for such antibody domain, tag, biotin, epitope, or affinity moiety. Examples of commonly encountered binding elements include protein A, streptavidin, monoclonal or polyclonal antibodies, and coordinated transition metal divalent cations. Alternatively, separations based on fluorescence detection and sorting can be used. Such separations typically distinguish the signal conveyed by a fluorescent moiety or fluorophore attached to the target, and permit the identification and selective separation of cells or particles bearing high concentrations of the target by fluorescence-activated cell sorting. The contributions of undesired ETRXs can be reduced by pre-absorption steps that mimic target exposure and enrichment, but are conducted in the absence of target.

Affinity

Selections or screens for ETRXs having the desired binding can be carried out by the methods described above followed by methods to identify candidate ETRXs of particular interest according to their affinity, activity, selectivity, solubility, or thermostability. Many methods for the measurement of affinity are known in the art and include solid phase as well as solution phase measurements of association constant or reaction on and off rates for combination of the ETRX with a target, or for the measurement of the catalytic activity of a catalytic ETRX. From the analysis of such equilibrium or kinetic constants the affinity of the ETRX for its target can be measured. Some methods of measuring affinity include, solid phase assays, such as planar or bead format assays, solution phase assays, or cell-based assays. Detection in such assays can be based on the analysis of changes in a signal generated by a detectably labeled target or ETRX, such as a radiolabeled target or ETRX, targets/ETRXs conjugated to or associated with an enzymatic activity or a fluorophore/fluorescent protein, or an active prosthetic group that behaves as a catalyst for a reaction or a change in property that is easily monitored. Common methods for measuring affinity include radiolabel or enzyme-linked immunosorbent assays, or assays based on surface plasmon resonance, fluorescence resonance, fluorescence polarization, or fluorescence autocorrelation spectroscopy/microscopy. A common form of affinity measurement is one in which target is immobilized on the solid phase, and varying concentrations of a solution containing a detectable form of the ETRX is contacted with the immobilized target to measure the amount of ETRX bound as a function of ETRX concentration.

Activity

For therapeutic purposes it is often useful to determine the activity of a particular ETRX for its proposed utility. For example, if the ETRX is to exert a therapeutic action by inhibiting the binding of an enzyme to its substrate or a ligand to its receptor, candidate ETRXs with affinity for the enzyme, ligand or receptor can be tested for their ability to inhibit 'the functional association that should be compromised for the desired effect. A bioassay is often used to determine the activity of a candidate ETRX, in which a cellular process or an in vivo response is measured in the presence or absence of progressively greater amounts of the ETRX of interest.

Selectivity

ETRXs according to the present invention may bind to single members of families of targets, or multiple members of families of targets, to achieve the desired therapeutic, analytical, manufacturing, or research utility. For example, the neutralization of biological activity for therapeutic purposes may optimally require the antagonism of more than one target, or the quantitation of such biological activity for analytical purposes may require the recognition of more than one target, or the purification of some targets of interest may require the recognition of families of related molecules.

The selectivity of candidate ETRXs can be manipulated during selection or screening by including competitor targets for which binding affinity is either desired or not desired. For example, to create a highly selective ETRX that recognizes one member of a multimember family of targets, such as a family of closely related proteins, a preselection can be made with the undesired targets, discarding the so-selected ETRXs, followed by a selection with the desired target. Or the activity of the ETRX identified by selection or screening methods can be assessed by comparing the binding affinity to the desired target with that of unrelated targets or related targets for which affinity is either desired or not desired. Such screening methods need not provide precise information, but for convenience may convey simple approximate measures of relative affinity, for example based on signal strength in an assay format similar to that of an enzyme linked immunosorbent assay (ELISA).

Solubility and Stability

Candidate ETRXs of the present invention that have been identified by selection or screening can be further evaluated and modified if necessary for additional properties that are required for the field of use. For example, for the manufacturing of ETRXs intended for most uses, a candidate ETRX can be highly soluble and thermostable. Methods are provided by the present invention for the evaluation of the solubility and thermostability of ETRXs as well as their suitability for expression in properly folded form in $E.\ coli$. In general methods for the evaluation of thermostability are well known in the art, and consist of thermal stress testing or extended storage testing at defined temperatures, followed by measurement of binding activity. In some cases a test for relative thermostability can be as simple as the measurement of the fraction of ETRX remaining soluble following incubation of the ETRX for a defined time at a particular temperature. Another suitable method for measuring thermostability is differential scanning calorimetry. Methods for the indirect assessment of folded status of proteins in $E.\ coli$ are also known in the art, and in the present invention comprise fusion of the candidate ETRX to an easily monitored protein whose activity is only apparent in its properly folded form, such as GFP or an antibiotic resistance. The relative degree of folding has been found by others to be a property shared by both domains of a fusion protein in $E.\ coli$, so that if the ETRX moiety is not properly folded, the likelihood that the GFP or antibiotic resistance moiety will be folded is commensurately low. In such cases cells expressing inactive or improperly folded ETRX fusion proteins will not show high green fluorescence or high antibiotic resistance.

Compositions

Compositions of nucleic acids and polypeptides, as well as substituted nucleic acids and substituted polypeptides, are included in the present invention.

Substituted ETRXs

Substituted ETRXs according to the present invention can be created by site-specific targeting methods that are either chemical or enzymatic in nature. Substitution may be provided either in vivo or in vitro, and can endow the nucleic acid or polypeptide with additional features useful for selection, purification, or therapeutic, analytical, manufacturing or research utility.

Exemplary substitutions that are frequently encountered in the art include prosthetic groups, such as biotin and lipoic acid, N-terminal modifications such as various amides and cyclic amides, alkylations of cysteine or selenocysteine residues, replacement of natural with unnatural amino acids, as for example may be practiced by proteolytic resection and replacement, the formation of isopeptide bonds such as are formed between glutamine and lysine residues, polymer substituents, such as polyalkylene glycols of varying lengths and/or branch structures, small organic molecule substituents, including receptor or ligand binding molecules or their fragments, and various other peptide or nonpeptide adducts that may be attached to the ETRX for a particular utility. The substitutions may aid in the detection, purification, or localization of the ETRXs and may confer favorable properties by virtue of such localization. For example substituted ETRXs may bind to plasma or cell surface proteins to extend the half-life of the substituted ETRX, or may be concentrated on the surface of particular cells, or in certain organs or tissues, by virtue of their affinity for cell-, organ- or tissue-selective secondary targets, such as receptors, carbohydrates, lipids or combinations of such secondary targets as may be presented by the organism to be treated or exposed to the ETRX.

The engineered thioredoxin-like fold proteins of the present invention may be delivered as pure proteins or may be generated in situ, for example following delivery by a gene targeting or genetic therapy that may involve the in vitro or in vivo modification of the genetic complement of an existing cell to produce the polypeptides of the present invention.

Substitution or Modification to Achieve Extended In Vivo Half-Life

Engineered thioredoxin-like fold proteins may be modified to extend their plasma half-life, for example by modification with polyethylene glycols, by translational fusion or post-translational crosslinking to naturally occurring plasma proteins having extended half-life or by a combination of such methods. Suitable naturally occurring plasma proteins having extended half-life include antibodies, albumin, apolipoproteins, serpins and some constituents of the complement and coagulation cascades. For example, translational fusion to human antibody Fc domains, particularly human IgG1 Fc domain, has been a widely used to improve plasma persistence of proteins. ETRXs may also be endowed with extended half-life by dimerization or multimerization to produce polypeptides that are too large to be naturally subject to renal filtration. Suitable methods for dimerization or multimerization include disulfide bond formation, translational fusion, and chemical or enzymatic crosslinking that is either site-selective or site-nonselective. When translational fusion is employed it may be necessary to provide one or more flexible linkers connecting monomers of the diversified thioredoxin-like fold domains. Such flexible linkers are well known in the art and may consist of a plurality of glycine residues in combination with chiral amino acids that provide favorable aqueous solubility, such as the charged or uncharged hydrophilic amino acids aspartic acid, glutamic acid, arginine, histidine lysine, serine, threonine, tyrosine, asparagine, or glutamine. Flexible linkers need not be confined to glycine and hydrophilic residues so long as the linker so constructed does not confer otherwise unfavorable biophysical properties on the ETRX, such as poor solubility, instability to aggregation, or susceptibility to proteolysis.

The formation of antibodies against ETRXs of the present invention can be minimized by the attachment of polymers, such as polyethylene glycols of varying size, branching morphology and attachment groups, to the core of the thioredoxin-like fold, their N terminal or C terminal extensions, or their prosthetic groups, using either site-selective or site-nonselective methods.

Additional Uses of ETRXs

Therapeutic Uses

The engineered thioredoxin-like fold proteins of the present invention can be used as targeting principles to deliver other therapeutic or analytical elements to an organism in need of therapy or diagnosis. For example, they may be attached to highly active cytostatic or cytotoxic agents to effect the growth arrest or elimination of an undesired cell type, such as a neoplastic or pre-neoplastic cell, or for the reduction in mass of a hypertrophic tissue or organ such as a hypertrophic prostate, or for the elimination of populations of immune cells that are undesired, for example those promoting or causing autoimmune syndromes. Such cytostatic or cytotoxic agents may be synthetic or natural small molecules, for example, maytansine and its derivatives, anthraquinones, alkylating agents such as cyclophosphamide or its prodrug forms, tubulin-binding agents, geldanamycin or its derivatives, or enediyne antibiotics such as calicheamycin, among others. The cytostatic or cytotoxic agents may also be proteinaceous toxins or combinations of small molecules and proteinaceous toxins. Proteinaceous toxins that may be employed for the purposes of cytostatic or cytotoxic therapies include bacterial toxins, members of which can be drawn from the 339 or more species or families that have been identified to date, including their natural variants, serotypes, isoforms, and allelic forms from both Gram-positive and Gram-negative bacteria (Alouf and Popoff, Eds. "The Comprehensive Sourcebook of Bacterial Protein Toxins, 3rd Ed." Academic Press. 2006). Exemplary bacterial toxins widely used for selective ablation of target cells or tissues include diphtheria toxin, *Pseudomonas* exotoxin A, anthrax lethal factor, and aerolysin.

Immunogenicity of recombinant therapeutic proteins is a safety concern that may be particularly important to consider for recombinant proteins derived from Trx due to its critical functions in biological systems. However, any anti-drug antibodies generated by the host against engineered Trx are most likely targeted to the epitopes that are located within the solvent exposed loops of the Trx scaffold. Among the solvent exposed loops the loop surrounding its enzymatic active site $^{32}$CGPC$^{35}$ (SEQ ID NO:3) is the most critical for the biological functions of Trx. This active loop, along with a second solvent exposed loop, can be mutated and randomized for binder selections in the present invention. Any host generated antibodies against the mutant Trx molecules will only recognize the epitopes located outside the active site of Trx, thus should spare the active site of endogenous Trx. Consequently it is unlikely for anti-drug antibodies against an engineered Trx to cause severe biological consequences stemming from autoimmunity against native Trx.

Bispecific ETRXs

Dimeric or higher multimeric ETRXs can be used to juxtapose cells or induce cellular actions by receptor crosslinking that may have a favorable therapeutic effect. For example, therapeutic strategies aimed at amplifying the cytotoxic action of macrophages, natural killer cells, or cytotoxic T cells have been described which rely upon the use of bispecific antibodies or related compositions. Such bispecific antibodies typically provide one antibody combining site that recognizes a target on the cell type to be ablated, and a second antibody combining site that recognizes a cell surface receptor on macrophages, natural killer cells, or T cells that, if engaged, induces the cytolytic effector program of those cells, leading to destruction of the target. Alternate forms of bispecific antibodies promote the selective disabling of responses by mast cells or B cells by producing crosslinks between activating receptors, such as the high affinity receptor for IgE on mast cells or the immunoglobulin receptor on B cells, and inactivating receptors, such as the inhibitory receptor for immunoglobulin FcγRIIB, also found on mast cells and B cells. The coordination of the activating receptor and the inhibitory receptor frustrates the signals emanating from the activating receptor, resulting in a favorable therapeutic effect. Similar bispecific compositions can be provided by the ETRXs of the present invention, which can be joined by a variety of methods to provide bi- or multi-specific binding principles for therapeutic treatments.

In addition, ETRXs of the invention may be used to target prodrug activating enzymes to cells, tissues or organs that are desired to be made subject to the action of the drug of interest. Such uses of ETRXs follow closely the uses of antibodies in antibody directed enzyme prodrug therapies, which rely upon antibodies for the targeting of a prodrug metabolizing moiety which converts a circulating prodrug to an active form. Such local activation schemes have been developed to allow a more specific delivery of highly toxic chemotherapeutic agents to the vicinity of a neoplastic cell in vivo.

Engineered thioredoxin-like fold proteins can also be used to deliver bioactive principles to a cell, organ, or tissue that is desired to be targeted. To produce interference with the function of a particular pathway that may be essential systemically but undesired in a specific organ, for example to block a hepatic action but not a central nervous system or renal or muscular action, an ETRX can be used to convey an antagonist of that pathway to a specific tissue, by (as in the example cited) binding to a liver-specific cell surface protein. A bioactive principle delivered by the ETRX can be attached to the ETRX by translational fusion or by chemical or enzymatic modification in a site-selective or site-nonselective manner.

Diagnostic Uses

ETRXs of the present invention can be used as antibody equivalents for many assay purposes. ETRXs can serve as the capture or detection reagent for ELISA-type assays or as the detection reagent for ELISpot assays or for the enumeration of protein abundance by flow cytometric measurement technologies. ETRXs can be conjugated to fluorophores, fluorescent proteins or enzymes to aid in the detection and/or quantitation of analytes of interest. Translational fusions of ETRXs to enzymes or other proteins that aid in the detection of analytes can be made and the resulting fusions can be expressed in prokaryotic or eukaryotic cells to provide a convenient renewable source of reagent. The favorable thermostability properties of ETRXs allow their use in arrays of analyte detector, for example in the planar format of protein binding arrays, or in the bead format of multiplexed fluorophore ratio indexed bead systems, such as the Luminex system. Detection of analyte binding with an ETRX can follow many of the assay format designs and detection schemes that have been disclosed for high sensitivity and selectivity detection by antibodies, such as light scattering, light surface plasmon scattering, fluorescence polarization, time resolved fluorescence, fluorescence autocorrelation, electroluminescence, chemiluminescence, fluorescence resonant energy transfer, fluorescence quenching or unmasking, coagulation or flocculation of beads, cells or other particles, or by providing nucleic acid or modified nucleic acid tags for detection by amplification methods including polymerase chain reaction, ligation-mediated probe amplification, branched nucleic acid assay, or isothermal amplification, with or without a ligation step; or by conveying enzymatic activities detectable by absorbance, fluorescence, evanescent field or surface potential perturbation. Monospecific or multispecific ETRXs can be prepared to identify unique analytes or families of analytes. In addition, monomeric, or multimeric ETRXs can be used as capture or detection reagents.

Labeled ETRXs can be used to image diseased cells, tissues or organs, either in vivo or in vitro. ETRXs can be conjugated to radionuclides, or to prosthetic groups incorporating or binding to other molecules comprising radionuclides. Common radionuclides used in imaging include F-18, 1-131, 1-123, Tc-99m, In-111 or Ga-67. Alternatively ETRXs can be conjugated to groups enclosing caged hyperpolarized xenon, or can be joined or attached to beads, nanoparticles or nanocrystals susceptible to detection by magnetic resonance imaging. Radionuclides can be detected by nuclear scintigraphy using equipment and methodology well known in the art, such as gamma cameras and positron emission tomography. In addition, images obtained by one modality, such as magnetic resonance imaging can be superimposed on images obtained by other modalities, such as nuclear scintigraphy, or two or more radionuclides of different spectral properties can be combined with different ETRXs, to permit better localization of images and more precise staging or diagnosis of disease conditions. Uses of such conjugated ETRXs include the in vivo imaging of tumors, infections, regions of ischemic damage or poor perfusion, clots, bone or eroded bone, sites of inflammation or degeneration, accumulations of amyloids, paraproteins or prion proteins, or to interrogate the status of prosthetic devices and/or their interfaces with normal or diseased tissue. ETRXs labeled with enzymes, fluorophores, fluorescent proteins, ferritin, gold or silver particles, or electron dense beads, can be used in conjunction with microscopic or ultramicroscopic techniques to diagnose pathological conditions or to identify, enumerate or quantitate the burden of relevant targets that signify the disease status of the cells, tissues, organs or organisms being studied. The imaging of tissues using labeled or conjugated ETRXs can be used to guide diagnostic or therapeutic procedures, such as biopsies, resections, radioablations, radiotherapy, or locally delivered chemotherapy.

Manufacturing Uses

The favorable thermostability and solubility properties of the ETRXs of the present invention also permit their use as adsorption reagents for the purification of proteins and complex biological structures, such as vaccine components. The positive manufacturing economies of prokaryotic production allow ETRXs to be used in settings for which the routine use of antibody reagents or materials would be considered prohibitively expensive.

Typically, for a manufacturing use an ETRX having the desired selectivity, solubility, thermostability, and affinity for a target will be prepared in a form that allows its constitution into an adsorbent, which may comprise a column medium, bead, or coated surface to which a target stream is to be exposed. Following adsorption of the target to the solid support, the nonbound material will be removed by one or more washing steps and the desired target material will be eluted, typically by raising or lowering the pH, as is common in the elution of antibody-based affinity supports. Various hydrophilic matrices that are used as supports for such affinity media are well known in the art and includes various, typically porous and crosslinked, polymers, such as crosslinked agaroses, dextrans, acrylamides, hydrophilic acrylates, or inorganic matrices such as controlled pore glass, or nonporous but fine particles such as magnetic beads, and functionalized or surface passivated silica or cellulose particles. ETRXs can be attached to such media by methods such as electrophilic attack by aldehydes, oxiranes, activated carbonates, iminocarbonates, cyanate esters, haloacetamides, maleimides, or activated esters, including carbodiimide activated carboxylic acids. Many commercial suppliers of pre-activated media suitable for attachment of the ETRX are known. In addition, the ETRX can be engineered by the incorporation of specific residues or sequences that favor the attachment of the ETRX to the media in an ETRX site-selective manner. For example, the incorporation of cysteine or selenocysteine residues, or substrate sequences for transglutaminases or sortases can be used to provide specific sites at which the ETRX can be linked to a solid support.

Research Uses

Research and analytical uses of ETRXs include the replacement of antibodies for detection and quantitation of analytes in various contexts, for example in immunoblotting, ELISA, ELISpot, flow cytometry, bead-based coagulation or detection systems, for detection of analytes by light scattering, surface plasmon scattering, chemiluminescent or electroluminescent detection, by fluorescence polarization, time-resolved fluorescence, fluorescence autocorrelation, fluorescence resonant energy transfer, or fluorescence quenching or unmasking. ETRXs can be conjugated with various fluorophores or fluorescent proteins to provide probes for the presence or absence of analytes. The analytes may include proteins, carbohydrates, nucleic acids, lipids, small molecules of natural, synthetic or semisynthetic origin, as well as polymers, glasses, metals and alloys, or combinations of these. ETRXs can be conjugated to enzymes, proteins, nucleic acids, carbohydrates, lipids, polymers, small molecules of natural, synthetic or semisynthetic origin, to provide an analyte detection method or additional functionality, or can be endowed with additional substituents having utility for detection or amplification of signal, such as by providing covalent or stable noncovalent attachment of nucleic acid or modified nucleic acid tags for detection by amplification methods including polymerase chain reaction, ligation-mediated probe amplification, branched nucleic acid assay, or isothermal amplification, with or without a ligation step. ETRXs can be adsorbed on solid surfaces, such as plates, trays, capillaries, fabrics, flexible or rigid sheets, beads, or particles, all of which may provide either surfaces for noncovalent absorption or chemically activated surfaces for covalent attachment. Such ETRX substituted surfaces may be used to provide either capture reagents, or in the case of bead or particulate adsorbed material, detection reagents. Examples of uses of labeled ETRXs include, without limitation, microscopy, ultramicroscopy, flow cytometry, flow microscopy, immunoblotting, immunoprecipitation, spectroscopy, or in vivo imaging.

The invention will now be further illustrated by the following non-limiting examples.

EXAMPLES

Example 1

Thioredoxin Library Construction for Biochemical Characterization

DNA libraries encoding thioredoxin with mutations and randomized residues (FIGS. 6A and 6B) were built using PCR extension of synthetic oligonucleotides with overlapping complementary ends. The synthetic oligonucleotides (listed in Table 4) were obtained from Integrated DNA Technologies (IDT). Random positions were introduced using the NNS nucleotide distribution. Library TRX-1A was built using oligos MS001, MS002 (Loop1 insert), MS004, MS005 (loop 3' insert), MS006 (loop 5 insert), MS010, and MS011. MS004 and MS005 were annealed and extended first and the product of this extension was used as a template for PCR using MS002 and MS006 as primers. The PCR product was gel purified and used as a template in the next round of PCR using MS001 and MS006 as primers. Cloning sites were added using MS010 and MS011. PCR was performed using Pfu polymerase or Phusion polymerase (New England Biolabs, NEB) and then cloned into pET28a using NcoI and NotI. A "wild type" thioredoxin (FIG. 6A) was made with MS007, MS008, and MS006 respectively. TRX-1B was made with the same set of oligonucleotides except with MS003 replacing MS002. TRX-2 library was made with MS009 replacing MS006.

TABLE 4

Synthetic oligonucleotides used for thioredoxin template and library construction.

MS001 ATGGTGAAGCAGATCGAGTCCAAGACCGCCTTCCAGGAAGCTCT
GGACGCTGCCGGCGATAAACTGGTTGTGGTTGACTTC
(SEQ ID NO: 9)

MS002 GATAAACTGGTTGTGGTTGACTTCTCTGCCACCNNSNNSNNSNN
SNNSNNSTGGTCCGGCCCATCCAAGATGATCAAGCCTTTCTTCC
AC
(SEQ ID NO: 10)

MS003 GATAAACTGGTTGTGGTTGACTTCTCTGCCACCTGGTGCGGCNN
SNNSNNSNNSNNSNNSCCATGCAAGATGATCAAGCCTTTCTTCC
AC
(SEQ ID NO: 11)

MS004 ATGATCAAGCCTTTCTTCCACTCCCTGTCCGAGAAGTACTCTAA
CGTGATTTTCCTCGAGGTGGATGTTGACGATGCTCAGGACGTGG
CC
(SEQ ID NO: 12)

MS005 CTCGCCAACCTTCTGACCTTTCTTGAAAAACTGGAAGGTTGGSN
NSNNSNNSNNSNNSNNAGCCTCGGAGGCCACGTCCTGAGCATCG
TC
(SEQ ID NO: 13)

MS006 CACCAGTTCGTTGATGGTGGCCTCCAGCTTTTCTTTGTTSNNSN
NSNNSNNGGCGCCGGAGAACTCGCCAACCTTCTGACCTTT
(SEQ ID NO: 14)

MS007 GATAAACTGGTTGTGGTTGACTTCTCTGCCACCTGGTCCGGCCC
ATCCAAGATGATCAAGCCTTTCTTCCAC
(SEQ ID NO: 15)

MS008 CTCGCCAACCTTCTGACCTTTCTTGAAAAACTGGAAGGTTGGCA
TAGCTTTCACCTCAGCCTCGGAGGCCACGTCCTGAGCATCGTC
(SEQ ID NO: 16)

MS009 CACCAGTTCGTTGATGGTGGCCTCCAGCTTTTCTTTGTTGGCGC
CGGAGAACTCGCCAACCTTCTGACCTTT
(SEQ ID NO: 17)

MS010 AATATATGCGGCCGCCACCAGTTCGTTGATGGTGGC
(SEQ ID NO: 18)

MS011 ATATTACCATGGTGAAGCAGATCGAGTCC
(SEQ ID NO: 19)

MS040 ATGGTGAAGCAGATCGAGTCCAAGACCGCCTTCCAGGAAGCTCT
GGACGCTGCCGGCGATAAACTGGTTGTGGTTGACTTC
(SEQ ID NO: 20)

MS041 GATAAACTGGTTGTGGTTGACTTCTCTGCCACCNNSNNSNNSNN
SNNSNNSNNSNNSTGGTCCGGCCCATCCAAGATGATCAAGC
CTTTCTTCCAC
(SEQ ID NO: 21)

MS042 GGCCACGTCCTGAGCATCGTCAACATCCACCTCGAGGAAAATCA
CGTTAGAGTACTTCTCGGACAGGGAGTGGAAGAAAGGCTTGATC
AT
(SEQ ID NO: 22)

MS043 GACGATGCTCAGGACGTGGCCTCCGAGGCTNNSNNSNNSNNSNN
SNNSNNSNNSNNSCCAACCTTCCAGTTTTTCAAGAAAGGTCAGA
AGGTTGGCGAG
(SEQ ID NO: 23)

MS044 CACCAGTTCGTTGATGGTGGCCTCCAGCTTTTCTTTGTTGGCGC
CGGAGAACTCGCCAACCTTCTGACCTTT
(SEQ ID NO: 24)

MS033 GCTAATACGACTCACTATAGGGACAATTACTATTTACAATTACA
(SEQ ID NO: 25)

MS034 TTTTTTTTTTTTTTTTTTTAAATAGCGGATGCGCTgcGTCAG
(SEQ ID NO: 26)

TABLE 4-continued

Synthetic oligonucleotides used for
thioredoxin template and library construction.

| | |
|---|---|
| MS031 | GCTAATACGACTCACTATAGGGACAATTACTATTTACAATTACA ATGGATTATAAAGACGACGACGATAAGGGTGGACCAGTGAAGCA GATCGAGTCCAAG (SEQ ID NO: 27) |
| MS032 | TTTTTTTTTTTTTTTTTTTAAATAGCGGATGCGCTGTCAGCTA CCACCAGTTCGTTGATGGTGGCC (SEQ ID NO: 29) |

Example 2

Effect of Peptide Insertion on Solubility and Thermostability

An established prior art is the use of thioredoxin as a scaffold to display peptide aptamers at the active site -$^{32}$CGPC$^{35}$- (SEQ ID NO:3). One rationale was that the disulfide bond formed between the cysteine residues can provide added stability to the core structure of thioredoxin scaffold. However, our analysis of evolutionary history of the thioredoxin-like fold suggests that peptide insertion at this location may not be well tolerated. Indeed, published studies have shown that specific peptide insertions at the active site between Gly33 and Pro34 can destabilize the thioredoxin structure severely, generating mutants with much reduced thermostability. Also based on sequence alignment of proteins with thioredoxin-like fold (FIG. 2), peptide insertions in loop1, N-terminus to the active site -CGPC- (SEQ ID NO:3) may be highly tolerable by the thioredoxin scaffold.

To investigate whether our evolution-based analysis on peptide insertion tolerability is applicable to random peptide insertions, we designed and prepared DNA libraries TRX-1A and TRX-1B (FIG. 6B & Example 1), each encoding a human thioredoxin library with nucleotide insertions corresponding to six random amino acids within loop1 (between T30 and W31) or at the active site (between G33 and P34), but both with the identical two additional mutations and/or insertions at loop3' (six amino acids of random sequence replacing five wild type amino acid sequence between A69 and P75) and loop5 (four amino acid insertion between A92 and N93). The solubility and thermostability of libraries TRX-1A and TRX-1B were examined to provide information on how the human thioredoxin would tolerate peptide insertions at the active site within the constraint of the disulfide bond between C32 and C35, as compared to a similar insertion within nearby loop1. Separately, TRX-2 library is designed so that the suitability of loop5 as a peptide insertion site may be examined in comparison with TRX-1A. TRX-2 contains the same insertion/mutation as TRX-1A minus the loop5 modification (FIG. 6B & Example 1), and sequence alignment of thioredoxin-like fold proteins predicts that loop5 can tolerate peptide insertions well (FIG. 2).

For TRX-1A, TRX-1B, and TRX-2 cloned into pET28, randomly selected sequences that were in frame and had no stop codons were transformed into BL21 cells and then expressed at 37° C. for 4 hours. Expressed bacterial pellets were spun down from 25 mL of culture and lysed using sonication and then separated into soluble and insoluble fractions after high speed centrifugation. Equal proportions of these fractions were analyzed by PAGE and those sequences having the protein in the soluble fraction determined. For those clones that yielded soluble proteins, the proteins were purified using the in frame-His tag from the pET28 vecor on Ni-NTA agarose (Qiagen). The protein was eluted using 200 mM imidazole and then dialyzed in TBS. The protein was diluted to 20 µM and then subjected to 10 min at different temperatures: 50° C., 60° C., 70° C., 80° C., and 90° C. The protein was centrifuged at high speeds to separate precipitated and soluble proteins. The supernatant was then analyzed using PAGE and the amount of soluble protein remaining was quantified using Krypton infrared stain (Pierce) and an Odyssey infrared scanner (LI-COR Biosciences). A protein is considered stable if more than 70% of the original amount of protein remains in the supernatant after heat treatment.

The results of these solubility and thermostability assays are summarized in Table 5. Whereas 70% and 80% of the proteins from TRX-1A and TRX-2 libraries are soluble, respectively, only 20% of TRX-1B members, with peptide insertion at the active site, are soluble. The thermostability results are even more lopsided; none from TRX-1B is stable at 80° C., while 80% from either TRX-1B or TRX-2 are stable. These results clearly show that peptide insertions within loop1, loop3', and loop5 into thioredoxin are well tolerated and generated mutants with superior biochemical properties. On the other hand, insertions within the active site of thioredoxin between G33 and P34 are severely detrimental to the solubility and stability of thioredoxin, even though such aptamer insertions had been proposed to be stabilized by C32-C35 disulfide bond and previously used for studies of peptide-protein interactions.

TABLE 5

Solubility and themostability screen of insertion mutants of thioredoxin.

| TRX Library | Number of In-frame Clones Expressed | Number (%) of Soluble Clones | Number of Soluble Clones Tested | Number (%) of Soluble Clones w/ $T_m > 80°$ C. |
|---|---|---|---|---|
| TRX-1A | 10 | 7 (70%) | 5 | 4 (80%) |
| TRX-1B | 5 | 1 (20%) | 1 | 0 (0%) |
| TRX-2 | 10 | 9 (90%) | 5 | 4 (80%) |

Example 3

Large Scale Thioredoxin Library Construction and mRNA Pre-Selection

TRX-3 was created using a slightly different strategy in order to maintain loop diversity. A primer extension reaction was performed for 10 cycles with MS041 and MS042 to create a fragment encoding a randomized loop 1. In a separate reaction, a second primer extension using MS043 and MS044 was performed to create a fragment encoding a randomized Loop 3'. These two fragments were mixed together to join the two loops in a primer extension reaction. The resultant combined fragment was gel purified and the diversity was calculated from the yield which came out to be $5.6 \times 10^{12}$ molecules. This fragment was amplified using PCR with primers MS040 and MS010 to create multiple copies of the library.

In order to purge the synthetic library of frameshifts and stop codons a pre-selection for "intact" sequences was performed using mRNA display (Cho, G. et al., *J. Mol. Biol.*, 2000, 297(2):309-19.). The TRX-3 library was amplified by PCR using primers MS031 and MS032 in order to perform mRNA display enrichment. The 5' primer contains the T7 RNA polymerase promoter as well as a portion of the TMV translational enhancer. The 3' primer contains a poly-A sequence as well as a binding site for an oligo for UV induced psoralen crosslinking in order to covalently attach puromycin to the 3' end of the mRNA. The puromycin crosslinking oligo is 5' Pso u agc gga ugc XXX XXX CC Pu 3' (SEQ ID NO:29), where Pso: C6-Psoralen; u, a, g, c are made from 2'OMe-RNA amidites; C: standard amidities; X: Spacer 9; Pu: Puromycin-CPG (Glen Research). A 2 mL in vitro translation reaction was performed using 0.5 µM crosslinked RNA concentration. The protein-RNA fusions were purified using oligo-dT cellulose, and then reverse transcribed using MS032 as a reverse primer and superscript III (Invitrogen). The RNA-protein fusions were then enriched for open reading frames by binding to M2-anti-FLAG agarose (Sigma) and subsequent elution by free FLAG peptide. Those RNA sequences with frameshifts and stop codons cannot form RNA-protein fusions due to early termination, and therefore will not be enriched during the FLAG selection. The diversity is calculated to be $2.5 \times 10^{11}$ unique clones based on the recovery from the FLAG column, the pool was subsequently PCR amplified using MS031 and MS032. Multiple copies of the library were made using PCR amplification with MS033 and MS044. In order to increase the diversity of the selected library, a unique asymmetric restriction site (BslI, NEB) was used to digest the amplified library into fragments containing each of the two randomized loops. These loops were then randomly recombined together using T4 DNA ligase (NEB) to regenerate the library diversity of $1 \times 10^{13}$.

Example 4

Phage Library Construction for CD5 Binder Selections

Phage libraries were constructed according to the procedure by a previously described procedure (Tonikian, R. et al., 2007, *Nature protocols*, (2):1368-1386). Our library was fused to the C-terminal domain of gene III from M13 phage in a phagemid vector derived from pUC119. The library is preceded by an SRP signal sequence from DsbA. Instead of using degenerate oligonucleotides to anneal to the single stranded phagemid template, we used a long single stranded primer that spanned the entire thioredoxin gene that was generated from a primer extension reaction from the mRNA display pre-selected library, TRX-3 (FIG. 4). After PCR amplification of the TRX-3 library with gc517 and gc519 (Table 6), single stranded primers were generated by repeated cycles of primer extension using a phosphorylated primer gc517. The double stranded DNA (cccDNA) synthesis reaction with T7 DNA polymerase and T4 DNA ligase (NEB) was performed using 20 µg of single stranded phagemid DNA and a 3-fold molar equivalent of the long single stranded primer. The single stranded template molecule for the Kunkel reaction encodes the thioredoxin gene with stop codons in the two loop regions where the randomization was introduced. The library was purified on a PCR purification column (Qiagen) and then electroporated into MC1061 F' variant or TG1 competent cells and then amplified using M13K07 helper phage (NEB). The total diversity of the library was calculated based on total number of unique clones. This process was repeated three times, and the combined library was estimated possess a total diversity of $9 \times 10^9$.

TABLE 6

Primer sequences used for construction of phage library TRX-3.

| | |
|---|---|
| gc517 | P-CAGATCGAGTCCAAGACCGCC (P = 5'-phosphate) (SEQ ID NO: 30) |
| gc519 | CAC CAG TTC GTT GAT GGT GGC (SEQ ID NO: 31) |

Example 5

Preparation of Extracellular Domain of CD5 for Selections

The extracellular domain for the CD5 receptor (ECD-CD5) was fused to a tag sequence with a streptavidin binding protein sequence (SBP) (FIG. 8A) (Keefe, A. D. et al., 2001, *Protein Expr. Purif.*, (23):440-446 and Wilson, D. S. et al., 2001, *Proc. Nat. Acad. Sci.*, (98):3750-3755) followed by a His8 tag in a mammalian expression vector. The construct was transiently transfected into HEK293T cells using tranfectin (Biorad) and allowed to express protein ECD-CD5-SBP-H8 for 5 days after changing the media to OptiMEM (Invitrogen). Media was harvested and then purified first using Ni-NTA agarose with 200 mM imidazole elution in PBS. A second purification on streptavidin-agarose (Pierce) was performed and the protein was eluted with 10 mM d-biotin in PBS. The purified protein was biotinylated using NHS-PEO4-biotin (Pierce) reagent and then dialyzed to remove free biotin.

Example 6

Phage Display Selections Using ECD-CD5-SBP-H8 as Target

Streptavidin magnetic beads (MyOne streptavidin T1 beads, Invitrogen) were pre-immobilized with biotinylated target protein ECD-CD5-SBP-H8. Approximately 200 µg of beads was incubated with a 200 nM solution of the target protein in a total volume of 500 µL, and subsequently blocked with 0.5% BSA in PBS. Approximately $10 \times 10^{12}$ phage were incubated with the beads for approximately an hour at room temperature and then washed ten times with 1 mL of the same buffer. The bound phage were eluted with 100 mM HCl and quickly neutralized with $\frac{1}{8}^{th}$ volume of 1M Tris pH 8.3. The phage were recovered by infecting log phase XL-1 blue cells for 30 min and subsequently adding $10^{10}$/mL M13K07 helper phage. The mixture was diluted into 2YT/Ampicillin and then amplified overnight. Phage were harvested from the media and precipitated with 20% PEG8000/2.5 M NaCl and then redissolved in PBS with 20% glycerol. Approximately $10^{11}$ phage were used in the next round of selection. For Rounds 2-4, the bound phage were washed with 1 mL PBS, pH 7.4 with 0.3 M NaCl, 0.5% BSA, 0.2% Tween-20 and 2 mM d-biotin in order to increase the stringency of the selection. The amount of phage recovery was calculated after tittering phage infection of XL-1 blue cells after elution. A titer increase was observed after three rounds of selection, the increase was further amplified after round 4 (FIG. 8B).

The enriched clones were sequenced, which revealed a unique CD5-binding clone E6 with the sequence shown in FIG. 9A. Based on the X-ray crystal structure of human thioredoxin, the mutation/insertion sequences in loop1 and loop3' of E6 are located in close proximity and could interact with the target CD5 in a concerted fashion.

A subsequent phage display experiment was done in which the phage were induced with 0.2 mM IPTG before the first round of selection and in between rounds in order to increase the display level of the thioredoxin-pIII fusion on the surface of each phage particle. Sequencing revealed that a higher proportion of the sequences from the selected pool were positive binders compared with the first selection. Binders designated as A1, A5, and E10 were identified from this experiment. The selection protocol remained the similar to that described above.

Example 7

Characterization of Selected E6 Phage Using ELISA

The phage expressing E6 protein was tested for its CD5 binding activity using ECD-CD5-SBP-H8 protein immobilized to streptavidin plates or HEK293T cells transfected with a vector that provide cell surface expression of CD5.

Protein based phage ELISA was performed as described (Tonikian, R. et al., 2007, *Nature protocols,* (2):1368-1386). Biotinylated CD5 was diluted to 1 μg/mL and then 100 μL was incubated in each well of a streptavidin coated plate (Nunc). The wells were then blocked with 0.5% BSA in PBS. Phage were produced by inoculating an XL-1 blue cell with a unique phagemid clone into 2YT media containing $10^{10}$/mL helper M13K07 helper phage. The growth media was diluted two-fold with PBT (PBS, 0.5% BSA, 0.05% Tween-20) and 100 μL was added to each of the wells; wells without immobilized CD5 was used as a control. The plate was washed eight times with 200 μL of PT (PBS, 0.05% Tween-20). Fifty μL of Anti-pVIII-HRP antibody was added at a 1:5000 dilution in PBT and incubated for 30 minutes at room temperature. After the plate was washed six times with 200 μL PT and then twice with PBS, 100 μL of a freshly mixed TMB/peroxide mixture (B ethyl Laboratories) was added to each well and incubated for 15 min. An acid stop solution was added and the plate was read at 450 nm. The results shown in FIG. 7B demonstrate that E6 binds to CD5, but not to the control streptavidin. As expected, the positive control anti-CD5 scFv antibody also showed similarly high CD5 selectivity. In comparison, neither a non-binder clone D6 nor the negative control (buffer only) shows any CD5 binding activity. Clones from the second phage selection; A1, A5, and E10 all show preferred binding to the biotinylated CD5 protein and not the control CD19 protein.

The cell-based phage ELISA was performed in a similar fashion, except the target CD5 was expressed on transiently transfected HEK293T cells. A confluent 10 cm plate of cells was split into 4 lysine-coated 96-well plates (BD Biosciences). One half of the plate was transfected with a mammalian expression vector encoding CD5 and the other half with an unrelated receptor, CD19, using 0.1 μg of DNA and 0.2 μL of transfectin per well. The transfected cells were grown for three days and then crosslinked to the well using 1% formalin solution in PBS after washing. The cells were blocked with PB for several hours to overnight and then phage were added and detected as described above. The results are shown in FIG. 7C. Whereas the positive controls anti-CD5 scFv and anti-CD19 scFv showed excellent binding to CD5- and CD19-expressing cells, respectively, E6 showed specific binding to CD5 expressing cells. Non-related TRX clone A2 did not bind to either cells.

Example 8

Expression, Characterization, and Cytotoxicity of a CD5-Binder-Aerolysin Fusion E6 clone from the CD5 selection was PCR amplified with gc615 and gc617 (Table 7), digested with EcoRI and NheI, and then cloned into modified pET28 based vectors designed to produce the free E6 protein and an N-terminal fusion to the large lobe of the aerolysin toxin protein, respectively. The protein was expressed in *E. coli* and then purified on Ni-NTA agarose then subsequently eluted with 200 mM imidazole. The eluted protein was dialyzed against TBS to remove free imidazole.

TABLE 7

Sequences of PCR primers used for cloning of CD5 binder E6.

| | |
|---|---|
| gc615 | AATAATAAGAATTCT GTGAAGCAGATCGAGTCCAAGACC (SEQ ID NO: 32) |
| gc617 | TAA TAA GCT AGC ACC ACC AGG CGC CAC CAG TTC GTT GAT GGT GGC CTC (SEQ ID NO: 33) |

The protein was diluted to 100 μM and then coupled with NHS-fluorescein at 1:3 ratio respectively. The free fluorescein was removed with dialysis and then the labeled protein was incubated with wild type Raji cells that do not express CD5 and modified Raji cell line ectopically expressing wild type CD5. The cells were harvested and washed with PBS with 0.5% BSA and then incubated with the labeled protein for 1 hr. The cells were briefly washed with PBS twice and then analyzed on a Facscalibur cell counter (BD Biosciences). The results shown in FIG. 10A illustrate that both free protein E6 and E6-aerolysin fusion protein can bind to the cell surface of CD5+Raji cells, but not the CD5− Raji cells. The positive control of this experiment was provided by anti-CD5 antibody, which also showed specific binding to CD5+ Raji cells only. This experiment established that E6 is capable of specific binding to cell surface CD5, and can direct a fused toxin to cells that express CD5.

The E6-aerolysin fusion protein was tested against Raji cells ectopically expressing or not expressing CD5 on the surface of the cell. Approximately 50,000 CD5 negative and positive cells were split into individual wells in a 96-well plate in RPMI media. The E6-aerolysin fusion was added at various concentrations in triplicate. After incubation for 48 hours, the cells were analyzed using MTS cytotoxicity assay (Promega) for 3 hours and then analyzed on a plate reader. PBS was used as a negative control and 0.1% Triton X-100 was used a positive control for toxicity. The dose response curves are shown in FIG. 8B. E6-aerolysin killed CD5+ cells with much lower $EC_{50}$ (132.1 nM) than CD5-cells ($EC_{50}$=1.56 μM), demonstrating CD5-selective affinity of E6-aerolysin.

Example 9

Thermostability Analysis of E6 and E6-Aerolysin Fusion Protein

To investigate whether the selected TRX-based CD5 binder E6 retained the thermostability of the wild type TRX, both E6 and E6-aerolysin fusion were analyzed for their tolerance to heat treatment. In 50 μL of PBS buffer, 20 μM of E6 protein and E6-aerolysion fusion protein were incubated at 0° C., 37° C., 55° C., 72° C., and 95° C., for 30 min, respectively. After centrifugation for 10 min. at 12,000 rpm, 30 μL of each supernatant was analyzed using PAGE and the amount of soluble protein remaining quantified using Krypton infrared stain (Pierce) and an Odyssey infrared scanner (LI-COR Biosciences). The results are summarized in FIG. 9.

The results indicate that E6 is remarkably stable. It did not lose any activity after heating for 30 min at 55° C., and more than 80% of the E6 protein remained soluble even after heating for 30 min at 95° C. (FIG. 11A). On the other hand, E6-aerolysin fusion lost most of its solubility after heated at 55° C. (FIG. 11B), suggesting that the aerolysin portion of the fusion protein was responsible for its lower stability.

The superior stability of E6 makes it an excellent candidate for affinity maturation and further optimization for binding of CD5 or other targets.

Example 10

Phage Library Construction for EpCAM Binder Selections

Phagemid vector with DsbA secretion leader sequence was used to construct human thioredoxin based libraries. Wild type template (as shown in FIG. 12A) was inserted in front of truncated pIII gene. Libraries were built with Kunkel mutagenesis methods. The oligonucleotides used for mutagenesis in the loop region have 5' and 3' overlaps to ensure proper annealing the uridine containing single stranded phagemid template. Designed primers were annealed onto the uridine-containing single strand phagemid, full length heteroduplex were synthesized by T7 DNA polymerase and ligated with T4 DNA ligase.

Three libraries based on human thioredoxin scaffold were constructed for EpCAM binder selections (FIG. 10). Library TRX-L1 uses Y/S code for randomized sequences in loop1, loop3/loop3', and loop5. Specifically, the active site peptide $^{32}SGPS^{35}$ (SEQ ID NO:4) is replaced by 4, 8, or 12 residues, 10 out of 12 residues within peptide $D^{61} \rightarrow A^{73}$ of loop3/loop3' are replaced with randomized sequences as indicated, and 4 random residues are used to replace the $^{90}SGAN^{93}$ (SEQ ID NO:34) peptide within loop5. In library TRX-L2 and TRX-L3, a randomized amino acid that replaces an existing residue is 50% NNS so that the wt residue is kept at 50%, while any insertion residue is NNS randomized.

Fifteen μg of single stranded DNA was used for each library. The heteroduplex DNA and enzyme mixture were purified with Qiagen PCR purification kit and eluted with 120 μL of deionized H$_2$O. They were mixed with 400 μL of XL1-blue electrocompetent cells (Stratagene) and electroporated at 2.5Kv, 200 ohm, 25 μF. SOC was added immediately after electroporation. The culture was incubated for 30 minutes at 37° C. with gentle shaking (200 rpm). The mixture was added into 300 mL of 2YT with helper phage at $10^{10}$/mL concentration and ampicilin to grow overnight. The phage was purified by PEG and its concentration determined by $OD_{268nm}$. The number of transformant, percentage of mutants, and calibrated diversity is shown in Table 8.

TABLE 8

Thioredoxin based library design and construction.

| TRX Library | Randomization | Diversity | Percentage of Viable Clones | Adjusted Diversity |
|---|---|---|---|---|
| TRX-L1 | Y/S | $5.4 \times 10^8$ | 44% | $2.4 \times 10^8$ |
| TRX-L2 | 50% NNS | $5.5 \times 10^9$ | 50% | $2.7 \times 10^9$ |
| TRX-L3 | 50% NNS for replacement, NNS for insertions | $1.0 \times 10^9$ | 50% | $0.5 \times 10^9$ |

Example 11

Phage Display Selections Using EpCAM as Target

To find specific binders from libraries TRX-L1, TRX-L2, and TRX-L3, recombinant EpCAM-Fc (R & D) was used as the target for selections. The phage display selection was done using T1 streptavidin magnetic beads (Invitrogen) coated with biotinylated recombinant EpCAM-Fc, and the selection was done with column based wash and elution to minimize non-specific background. The target concentration for coating in round 1 and round 2 selections is 250 nM, which is reduced to 125 nM in the $3^{rd}$ round. This process works efficiently as only two rounds were necessary to recover specific binders. The progression of phage titer for rounds 2 and 3 was monitored. Sequencing of the pools from post round 2 indicated a convergence of binders. The hit rates of post round 2 are 24/26 for TRX-L1, 21/23 for TRX-L2, and 21/24 for TRX-L3, respectively. The hit rate of post round 3 is 24/24 for both TRX-L2 and TRX-L3.

More specifically, 250 nM of biotinylated EpCAM-Fc was coated onto 50 μl of T1 beads for 30 min at RT. The coated beads were washed with selection buffer twice and then incubated with the library for 1 hr. After binding, the beads were washed quickly for 5 times with 1 mL of wash buffer and loaded onto column for flow wash by 50 mL of wash buffer. Elution was done with 100 μl of 100 mM HCl for 10 min followed by neutralization with 15 μL of 1M Tris pH 9.1. The last wash and elution were titered with XL1-blue cells. The $1^{st}$ round elution was amplified with XL-1 blue cells at OD 0.5. The $2^{nd}$ round of selection was done by washing for 8 times and flow wash of 50 mL. The $3^{rd}$ round of selection was done with 125 nM target concentration and 10 times of wash followed by 50 mL of flow wash. A total of 22 different binders have been obtained from three combined libraries (FIG. 13).

Example 12

Characterization of Phage Display Selected EpCAM Binders

The selected phages from libraries TRX-L1, TRX-L2, and TRX-L3 that display TRX-based EpCAM binders were analyzed by phage ELISA. Specifically, a single bacterial colony was inoculated into 1 mL of 2YT media with ampcillin and helper phage M13 at $10^{10}$/mL. After the culture was incubated at 37° C. overnight, it was spun at Max speed in a microcentrifuge and the supernatant was used for phage ELISA. The nunc plate wells were coated with EpCAM-Fc at 1 μg/mL overnight at 4° C. The plate wells were blocked by 1% BSA in PBS. The phage supernatant was diluted with blocking buffer for ten fold and was applied to the wells for 1 hr. The wells were washed 5 times with PBS containing 0.05% tween-20. Bound phage was detected with an anti- M13 pVlll antibody conjugated to HRP. The wells were incubated with anti M13 pVIII-HRP conjugate at 1:5000 in blocking buffer for 1 hr. Detection was done with ELISA reagent (R&D) and measured at 450 nm. Specific binding to EpCAM as compared to BSA control was observed for all 22 selected binders (FIG. 14).

An examination of the selected sequences from all three libraries (FIG. 13) showed that the mutations in loop5 are limited, and five clones completely retained the wild type sequence $S^{90}GAN^{93}$. In contrast, many selected amino acids different from the wild type are observed in the region of loop3/loop3', suggesting that this motif may be involved in interactions with the target EpCAM. Similarly, a wide range of variability in both length and sequence has been observed in the loop1/active site region, pointing to its involvement in target recognition. A closer look at the locations of loop1, loop3, and loop3' in the X-ray crystal structure (FIG. 5B) revealed that these three loops are in close spatial proximity and are pointing to the same direction, presumably on the same face as the binding surface with EpCAM. Interestingly all the selected sequences from TRX-L2 and TRX-L3 in loop1 possess a Pro at position 32, which may be favored to make a turn at the location that corresponds to $Cys^{32}$ in wild type thioredoxin (FIG. 5B). Somewhat surprisingly, 16 out of 17 selected binders from the TRX-L3 library, which contained randomized 4aa, 5aa, baa, and 7aa in replacement of 4aa $^{32}SGPS^{35}$, prefer a 5aa peptide at the site. This feature could be very useful for the design of the second generation libraries for affinity maturation.

To demonstrate binding specificity as compared to other cell surface targets, the following proteins were immobilized on wells of nunc plates and reacted with phage: EpCAM-Fc, IgG1-Fc, CD22-Fc, CD5-Fc, hEphA2, mEphA2-Fc, BSA. In addition, a control clone, which was not selected as an EpCAM binder, was also analyzed. The corresponding phage ELISA results are shown in FIG. 15A. While the selected EpCAM binders from TRX-L1 and TRX-L2 libraries showed excellent binding selectivity towards target EpCAM, they did not bind to any of the control proteins. Furthermore, the control phage clone showed weak and non-specific interactions with almost all of the other proteins tested.

To examine the thermostability of the selected clones, the individual phage clones were heat treated before ELISA analysis. Specifically, the selected phage supernatant was incubated at the indicated temperatures for 10 min, followed by centrifugation to remove precipitated aggregates. The supernatants were used for phage ELISA analysis (FIG. 15B). The results show that the selected clone F6 from TRX-L1 lost its binding activity after heated at 60° C. Meanwhile, the selected clones from library TRX-L2 were stable at 70° C. and retained their binding activity. We did not heat the phage clones at temperatures higher than 70° C., at which phage itself becomes less stable. These results seem to be in agreement with the notion that an insertion of long peptide sequences at the TRX active site markedly destabilizes the scaffold. The F6 clone contains 12 amino acids at the active site, whereas the wild type template has only 4 amino acids located at the corresponding location.

Example 13

Additional Binders for Various Protein Targets

Additional phage display selections were carried out to select specific binders for CD3E, CD19, CD22, EpCAM, LGR5, and human serum albumin (HSA) using TRX-3 library and the phage display procedures similar to that described in Example 6. For the HSA selection, 0.125% casein was used in place of the 0.5% BSA as a blocking agent during selection and ELISA analysis. The recombinant target proteins were prepared using methods summarized in Table 9.

TABLE 9

Preparation of Target Proteins

| Target | Expression system | Purification | Biotinylation |
|---|---|---|---|
| CD5 | 293T | Ni-NTA, Streptavidin agarose | NHS-PEO4-biotin 1:5 ratio |
| EpCam | 293T | Ni-NTA, Streptavidin agarose | BirA + ATP + Biotin |
| CD3e | 293T | Ni-NTA, Streptavidin agarose | BirA + ATP + Biotin |
| LGR5-Fc | 293T | Protein A agarose | BirA + ATP + Biotin |
| Streptavidin | Purchased (Invitrogen) | On magnetic beads | |
| HSA | Purchased (Sigma) | | NHS-PEO4-biotin 1:5 ratio |
| CD19-Fc domains | 293T | Protein A agarose | BirA + ATP + Biotin |
| CD22-Fc domain | 293T | Protein A agarose | BirA + ATP + Biotin |

From the TRX-3 library and using phage display, binders to the target proteins listed in Table 9 were selected. The selected loop1 and loop 3' sequences are listed in Table 10. Representative sequences are also shown in FIG. 16.

TABLE 10

Sequences of loop1 and loop3' in the selected binders to target proteins

| Target Protein | Clone Name | Selected Loop 1 | SEQ ID NO | Selected Loop 3' | SEQ ID NO |
|---|---|---|---|---|---|
| CD5 | A1 | QWWGWIDGQ | 35 | YPLFGMAAL | 36 |
| | A5 | QCNTGESHD | 37 | WSPLIMCTM | 38 |
| | E6 | NTIKHGGSR | 39 | EKGILVSPL | 40 |
| | E10 | KERDSAWDD | 41 | FYWSYPSLP | 42 |
| CD3ε | A3 | GRCYVDGRL | 43 | KRMLCLVRT | 44 |
| | C4 | VTCDHEGCK | 45 | SNFAVTFFF | 46 |
| | C7 | SARVWSCIP | 47 | SRPLTLIRS | 48 |
| | C8 | PKARTKRNS | 49 | MIFGRLVII | 50 |
| | E8 | NRRPQRNAK | 51 | LMLFFSRII | 52 |
| CD19 | A1 | KRNDNTSDT | 53 | FRRWNSRWG | 54 |
| | A5 | GDEQLVGRR | 55 | FRRWNSRWG | 54 |
| CD22 | A4 | RDPNNCRGT | 56 | CVLYSVGYA | 57 |
| | A6 | KEPTVIGFW | 58 | LSPLFNFPL | 59 |
| | E1 | NVRESHKRG | 60 | VSMFVLDSW | 61 |
| EpCAM | A6 | NRNGEKHAH | 62 | GLLWSIPFR | 63 |
| | A4 | TRDWNRDVN | 64 | QLTLSIPFR | 65 |
| | C9 | SEANGEE-- | 66 | LRVWSIPER | 67 |
| | G6 | HTNESRDGN | 68 | ELIWSLPER | 69 |
| | F6 | GQNRKRTED | 70 | AILISLPER | 71 |

TABLE 10-continued

Sequences of loop1 and loop3' in the
selected binders to target proteins

| Target Protein | Clone Name | Selected Loop 1 | SEQ ID NO | Selected Loop 3' | SEQ ID NO |
|---|---|---|---|---|---|
| | F12 | RGP----- | 72 | FHASFVPLR | 73 |
| | E10 | QHKP----- | 74 | SYVYALPRR | 75 |
| | A2 | CGRYEEGRR | 76 | LPLVYFCPY | 77 |
| | A11 | GCVRTMARR | 78 | MSSNKYICF | 79 |
| | E4 | CVVTTGDSK | 80 | TRELLPYCW | 81 |
| | E5 | YRTHTNEIR | 82 | RFLTLRSSS | 83 |
| | E6 | SRQGGICSR | 84 | RISLWCAWT | 85 |
| | E7 | GSSPESRVH | 86 | ACKHRVCFF | 87 |
| | F1 | NWSSSSGKD | 88 | RYVFPPEAV | 89 |
| | F2 | QCWARRRDR | 90 | GPRNTLLCF | 91 |
| | F3 | DTTKDRGGT | 92 | LPWTVQFGY | 93 |
| | F10 | GKVCGGKRR | 94 | ARPHFCPVM | 95 |
| | F11 | RDARAAPPS | 96 | LPWPSYFGL | 97 |
| | G9 | WNTRAHCSR | 98 | LLPPLCTID | 99 |
| | H2 | KENNGWRGN | 100 | MAGPRVMGP | 101 |
| | H3 | NKRGEGWQK | 102 | SVIMWPQLW | 103 |
| | H9 | CYAVREGQG | 104 | LYTALLYCT | 105 |
| LGR5 | A7 | --------S | | AWLTPNRVP | 106 |
| | B2 | SANSGWCCG | 107 | LDIESFLYF | 108 |
| | B5 | EEKGYEGRR | 109 | YVPFSLSGY | 110 |
| | D2 | RYEETTRQH | 111 | RVASKRSAF | 112 |
| | E7 | KWESPYEAV | 113 | LSHSVPYYL | 114 |
| HSA | C6 | CQTGTKQLP | 115 | FGHFGFPTL | 116 |
| | E1 | RSENDRWNE | 117 | LIAGPFWYS | 118 |
| | E2 | KNEKRDVAE | 119 | FGFFGFPVL | 120 |
| | E5 | RRNERARDW | 121 | LAAGPFYLL | 122 |
| | F3 | GGTPGRRNR | 123 | FCEFCFPFL | 124 |
| | G5 | RLRTGGHPY | 125 | VYVSLSRHR | 126 |
| | H6 | DRKPWKTRG | 127 | FGLFSFPLL | 128 |

An alignment of selected HSA binders revealed that three types of Loop3' motifs (FIG. 17), i.e., the F-rich motif (A11, C6, E2, F3, and H6), the AGPF motif (E1 and E5), and a unique sequence motif (G5), were selected.

Phage ELISA experiments on the HSA binders were performed as described in Example 7 and the results are shown in FIG. 18A. Selective binding to HSA vs. CD5 was observed for all the HSA binders tested. The A11 clone was omitted due to the presence of a stop codon in its Loop1 sequence. The sequences of the seven remaining HSA binders shown in Table 10 and FIG. 7 were similarly tested for their specific binding to serum albumins of human, rat, and mouse (HSA, RSA, and MSA, respectively) by phage ELISA (FIG. 18B). As summarized in FIG. 18C, HSA binding clones comprising the F-rich Loop3' motif are capable of specific binding to all three serum albumins, while the clones containing the AGPF Loop3' motif (residues 10-18 of SEQ ID NO:7) and the unique Loop3' sequence VYVSLSRHR (SEQ ID NO:126) can only bind to HSA, not RSA or MSA. These findings suggest that different HSA epitopes are recognized by the selected binders with different Loop3' motifs, and the diversity of the selected binders may have a variety of different applications depending on their species specificity.

Affinity measurements on HSA binders were performed on a Biacore T100 instrument according to manufacturer's instructions. The target protein (HSA) was immobilized on the Biacore CM5 sensor chip using EDC/NHS coupling chemistry. A kinetic model was used to fit the binding affinity after measuring the sensograms while varying the concentration of the purified thioredoxin based binders. The resulting $K_d$ values are shown in the left panel of FIG. 19 along with the corresponding surface plasmon resonance (SPR) sensorgrams.

Example 14

Pharmakokinetics Studies on HSA Binders

The HSA-binding thioredoxin clones E2, F3, and H6 (all with F-rich motif), as well as the wild type sequence were cloned as his-tagged C-terminal fusions to a stabilized mutant Renilla Luciferase and subsequently purified using Ni-NTA (Loening et al. Protein Engineering, Design & Selection vol. 19 no. 9 pp. 391-400, 2006). The proteins were dialyzed in PBS prior to administration to mice. The affinity of each fusion protein was measured using Biacore T100 as described above and the resulting $K_d$ values are shown in the right panel of FIG. 19 along with the corresponding SPR sensorgrams.

For each Luciferase-thioredoxin fusion, three Swiss Webster mice were injected with 50 ug of protein diluted in 200 uL PBS. Blood samples were collected at 30 min, 3 hrs, 6 hrs, 24 hrs, and 48 hrs after the injection. Each sample was mixed with EDTA and the blood cells were removed; the plasma was flash frozen and stored at −80° C. until samples at all of the time points were collected. The plasma was thawed and then 1 uL equivalent from each sample was diluted into 100 uL of PBS/coelenterazine in 0.5% BSA and the light output was measured on a TopCount reader. The average light output from the three mice was plotted for each clone and time point, and the resulting curves are shown in FIG. 20A. The resulting areas under the curve (AUC) for each Luciferase-thioredoxin fusion are shown in FIG. 20B. The E2, F3, and H6 fusions showed ~5-9 fold longer half-lives than the wild type TRX fusion, in general agreement with their increased affinity for HSA (FIG. 19, right panel). While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims. Other embodiments are within the claims.

What is claimed is:

1. A loop-diversified engineered human thioredoxin protein comprising a Cysteine to Serine mutation at C32 and C35, and at least one mutation in loop 1, loop 3, or loop 5, wherein the at least one mutation comprises at least one random amino acid(s) inserted between T30 and W31 in loop 1; or replacement of 5 residues between Ala69 and Pro75 with at least 5 randomized residues in loop 3.

2. The loop-diversified engineered human thioredoxin protein of claim 1, which is derived from a protein comprising SEQ ID NO:219.

3. An undivided sample comprising a plurality of different loop-diversified engineered human thioredoxin proteins according to claim 1.

4. The undivided sample of claim 3 comprising at least 100 distinct different loop-diversified engineered human thioredoxin proteins.

5. The loop-diversified engineered human thioredoxin protein of claim 1, comprising SEQ ID NO:219 with a Cysteine to Serine mutation at C32 and C35 and mutations in loop 1 and loop 3.

6. The loop-diversified engineered human thioredoxin protein of claim 1, comprising at least one of: one to nine random amino acids inserted between T30 and W31 in loop1; and replacement of 5 residues between Ala69 and Pro75 with 5 to 9 randomized residues in loop 3.

7. The loop-diversified engineered human thioredoxin protein of claim 6, comprising a Cysteine to Serine mutation at C32 and C35, six random amino acids inserted between T30 and W31 in loop 1; and replacement of 5 residues between Ala69 and Pro75 with 9 randomized residues in loop 3.

* * * * *

UNITED STATES PATENT AND TRADEMARK OFFICE
CERTIFICATE OF CORRECTION

PATENT NO. : 9,340,584 B2
APPLICATION NO. : 14/006237
DATED : May 17, 2016
INVENTOR(S) : Jia L. Wolfe et al.

It is certified that error appears in the above-identified patent and that said Letters Patent is hereby corrected as shown below:

In the Claims

In columns 193-194, line 62 (approx.), in Claim 4, before "different" delete "distinct"; and In column 195, line 3, in Claim 6, delete "loop1;" and insert -- loop 1; --.

Signed and Sealed this
Sixteenth Day of August, 2016

Michelle K. Lee
*Director of the United States Patent and Trademark Office*

SEQUENCE LISTING

<160> NUMBER OF SEQ ID NOS: 254

<210> SEQ ID NO 1
<211> LENGTH: 4
<212> TYPE: PRT
<213> ORGANISM: artificial
<220> FEATURE:
<223> OTHER INFORMATION: microbial transglutaminase substrate peptide
      tag

<400> SEQUENCE: 1

```
Leu Leu Gln Gly
1

<210> SEQ ID NO 2
<211> LENGTH: 5
<212> TYPE: PRT
<213> ORGANISM: artificial
<220> FEATURE:
<223> OTHER INFORMATION: microbial sortasesubstrate peptide tag

<400> SEQUENCE: 2

Leu Pro Glu Thr Gly
1               5

<210> SEQ ID NO 3
<211> LENGTH: 4
<212> TYPE: PRT
<213> ORGANISM: artificial
<220> FEATURE:
<223> OTHER INFORMATION: thioredoxin-like protein active site

<400> SEQUENCE: 3

Cys Gly Pro Cys
1

<210> SEQ ID NO 4
<211> LENGTH: 4
<212> TYPE: PRT
<213> ORGANISM: artificial
<220> FEATURE:
<223> OTHER INFORMATION: thioredoxin-like protein active site

<400> SEQUENCE: 4

Ser Gly Pro Ser
1

<210> SEQ ID NO 5
<211> LENGTH: 4
<212> TYPE: PRT
<213> ORGANISM: artificial
<220> FEATURE:
<223> OTHER INFORMATION: thioredoxin-like protein active site consensus
      sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 5

Cys Xaa Xaa Cys
1

<210> SEQ ID NO 6
<211> LENGTH: 18
<212> TYPE: PRT
<213> ORGANISM: artificial
<220> FEATURE:
<223> OTHER INFORMATION: F-rich HSA binding motif
<220> FEATURE:
<221> NAME/KEY: misc_feature
<222> LOCATION: (1)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(14)
```

```
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid

<400> SEQUENCE: 6

Xaa Xaa Xaa Xaa Xaa Xaa Xaa Xaa Xaa Phe Xaa Xaa Phe Xaa Phe Pro
1               5                   10                  15

Xaa Xaa

<210> SEQ ID NO 7
<211> LENGTH: 18
<212> TYPE: PRT
<213> ORGANISM: artificial
<220> FEATURE:
<223> OTHER INFORMATION: AGPF HSA binding motif
<220> FEATURE:
<221> NAME/KEY: misc_feature
<222> LOCATION: (1)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (16)..(18)
<223> OTHER INFORMATION: Xaa can be any naturally occurring amino acid

<400> SEQUENCE: 7

Xaa Xaa Xaa Xaa Xaa Xaa Xaa Xaa Xaa Leu Xaa Ala Gly Pro Phe Xaa
1               5                   10                  15

Xaa Xaa

<210> SEQ ID NO 8

<400> SEQUENCE: 8

000

<210> SEQ ID NO 9
<211> LENGTH: 81
<212> TYPE: DNA
<213> ORGANISM: artificial
<220> FEATURE:
<223> OTHER INFORMATION: oligonucleotide for thioredoxing template and
      library construction

<400> SEQUENCE: 9
atggtgaagc agatcgagtc caagaccgcc ttccaggaag ctctggacgc tgccggcgat       60
aaactggttg tggttgactt c                                                 81

<210> SEQ ID NO 10
<211> LENGTH: 90
<212> TYPE: DNA
<213> ORGANISM: artificial
<220> FEATURE:
<223> OTHER INFORMATION: oligonucleotide for thioredoxing template and
      library construction
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
```

```
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 10
gataaactgg ttgtggttga cttctctgcc accnnsnnsn nsnnsnnsnn stggtccggc    60
ccatccaaga tgatcaagcc tttcttccac                                    90

<210> SEQ ID NO 11
<211> LENGTH: 90
<212> TYPE: DNA
<213> ORGANISM: artificial
<220> FEATURE:
<223> OTHER INFORMATION: oligonucleotide for thioredoxing template and
      library construction
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 11
gataaactgg ttgtggttga cttctctgcc acctggtgcg gcnnsnnsnn snnsnnsnns    60
ccatgcaaga tgatcaagcc tttcttccac                                    90

<210> SEQ ID NO 12
<211> LENGTH: 90
<212> TYPE: DNA
<213> ORGANISM: artificial
<220> FEATURE:
<223> OTHER INFORMATION: oligonucleotide for thioredoxing template and
      library construction

<400> SEQUENCE: 12
atgatcaagc ctttcttcca ctccctgtcc gagaagtact ctaacgtgat tttcctcgag    60
gtggatgttg acgatgctca ggacgtggcc                                    90

<210> SEQ ID NO 13
<211> LENGTH: 90
```

```
<212> TYPE: DNA
<213> ORGANISM: artificial
<220> FEATURE:
<223> OTHER INFORMATION: oligonucleotide for thioredoxing template and
      library construction
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t

<400> SEQUENCE: 13
ctcgccaacc ttctgacctt tcttgaaaaa ctggaaggtt ggsnnsnnsn nsnnsnnsnn    60
agcctcggag gccacgtcct gagcatcgtc                                    90

<210> SEQ ID NO 14
<211> LENGTH: 84
<212> TYPE: DNA
<213> ORGANISM: artificial
<220> FEATURE:
<223> OTHER INFORMATION: oligonucleotide for thioredoxing template and
      library construction
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t

<400> SEQUENCE: 14
caccagttcg ttgatggtgg cctccagctt ttctttgtts nnsnnsnnsn nggcgccgga    60
gaactcgcca accttctgac cttt                                          84

<210> SEQ ID NO 15
<211> LENGTH: 72
<212> TYPE: DNA
<213> ORGANISM: artificial
<220> FEATURE:
<223> OTHER INFORMATION: oligonucleotide for thioredoxing template and
      library construction

<400> SEQUENCE: 15
gataaactgg ttgtggttga cttctctgcc acctggtccg gcccatccaa gatgatcaag    60
```
cctttcttcc ac                                                          72

<210> SEQ ID NO 16
<211> LENGTH: 87
<212> TYPE: DNA
<213> ORGANISM: artificial
<220> FEATURE:
<223> OTHER INFORMATION: oligonucleotide for thioredoxing template and
      library construction

<400> SEQUENCE: 16
ctcgccaacc ttctgacctt tcttgaaaaa ctggaaggtt ggcatagctt tcacctcagc      60
ctcggaggcc acgtcctgag catcgtc                                          87

<210> SEQ ID NO 17
<211> LENGTH: 72
<212> TYPE: DNA
<213> ORGANISM: artificial
<220> FEATURE:
<223> OTHER INFORMATION: oligonucleotide for thioredoxing template and
      library construction

<400> SEQUENCE: 17
caccagttcg ttgatggtgg cctccagctt ttctttgttg gcgccggaga actcgccaac      60
cttctgacct tt                                                          72

<210> SEQ ID NO 18
<211> LENGTH: 36
<212> TYPE: DNA
<213> ORGANISM: artificial
<220> FEATURE:
<223> OTHER INFORMATION: oligonucleotide for thioredoxing template and
      library construction

<400> SEQUENCE: 18
aatatatgcg gccgccacca gttcgttgat ggtggc                                36

<210> SEQ ID NO 19
<211> LENGTH: 29
<212> TYPE: DNA
<213> ORGANISM: artificial
<220> FEATURE:
<223> OTHER INFORMATION: oligonucleotide for thioredoxing template and
      library construction

<400> SEQUENCE: 19
atattaccat ggtgaagcag atcgagtcc                                        29

<210> SEQ ID NO 20
<211> LENGTH: 81
<212> TYPE: DNA
<213> ORGANISM: artificial
<220> FEATURE:
<223> OTHER INFORMATION: oligonucleotide for thioredoxing template and
      library construction

<400> SEQUENCE: 20
atggtgaagc agatcgagtc caagaccgcc ttccaggaag ctctggacgc tgccggcgat      60
aaactggttg tggttgactt c                                                81

<210> SEQ ID NO 21
<211> LENGTH: 99
<212> TYPE: DNA
<213> ORGANISM: artificial

```
<220> FEATURE:
<223> OTHER INFORMATION: oligonucleotide for thioredoxing template and
      library construction
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 21
gataaactgg ttgtggttga cttctctgcc accnnsnnsn nsnnsnnsnn snnsnnsnns        60
tggtccggcc catccaagat gatcaagcct ttcttccac                              99

<210> SEQ ID NO 22
<211> LENGTH: 90
<212> TYPE: DNA
<213> ORGANISM: artificial
<220> FEATURE:
<223> OTHER INFORMATION: oligonucleotide for thioredoxing template and
      library construction

<400> SEQUENCE: 22
ggccacgtcc tgagcatcgt caacatccac ctcgaggaaa atcacgttag agtacttctc        60
ggacagggag tggaagaaag gcttgatcat                                        90

<210> SEQ ID NO 23
<211> LENGTH: 99
<212> TYPE: DNA
<213> ORGANISM: artificial
<220> FEATURE:
<223> OTHER INFORMATION: oligonucleotide for thioredoxing template and
      library construction
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
```

<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t

<400> SEQUENCE: 23
gacgatgctc aggacgtggc ctccgaggct nnsnnsnnsn nsnnsnnsnn snnsnnscca    60
accttccagt ttttcaagaa aggtcagaag gttggcgag                          99

<210> SEQ ID NO 24
<211> LENGTH: 72
<212> TYPE: DNA
<213> ORGANISM: artificial
<220> FEATURE:
<223> OTHER INFORMATION: oligonucleotide for thioredoxing template and
      library construction

<400> SEQUENCE: 24
caccagttcg ttgatggtgg cctccagctt ttctttgttg gcgccggaga actcgccaac    60
cttctgacct tt                                                       72

<210> SEQ ID NO 25
<211> LENGTH: 44
<212> TYPE: DNA
<213> ORGANISM: artificial
<220> FEATURE:
<223> OTHER INFORMATION: oligonucleotide for thioredoxing template and
      library construction

<400> SEQUENCE: 25
gctaatacga ctcactatag ggacaattac tatttacaat taca                    44

<210> SEQ ID NO 26
<211> LENGTH: 43
<212> TYPE: DNA
<213> ORGANISM: artificial
<220> FEATURE:
<223> OTHER INFORMATION: oligonucleotide for thioredoxing template and
      library construction

<400> SEQUENCE: 26
tttttttttt tttttttttt aaatagcgga tgcgctgcgt cag                     43

<210> SEQ ID NO 27
<211> LENGTH: 101
<212> TYPE: DNA
<213> ORGANISM: artificial

```
<220> FEATURE:
<223> OTHER INFORMATION: oligonucleotide for thioredoxing template and
      library construction

<400> SEQUENCE: 27
gctaatacga ctcactatag ggacaattac tatttacaat tacaatggat tataaagacg    60
acgacgataa gggtggacca gtgaagcaga tcgagtccaa g                       101

<210> SEQ ID NO 28
<211> LENGTH: 67
<212> TYPE: DNA
<213> ORGANISM: artificial
<220> FEATURE:
<223> OTHER INFORMATION: oligonucleotide for thioredoxing template and
      library construction

<400> SEQUENCE: 28 ttttttttt ttttttttt aaatagcgga tgcgctgtca gctaccacca gttcgttgat    60
ggtggcc                                                             67

<210> SEQ ID NO 29
<211> LENGTH: 12
<212> TYPE: RNA
<213> ORGANISM: artificial
<220> FEATURE:
<223> OTHER INFORMATION: oligonucleotide for puromycin crosslinking
<220> FEATURE:
<221> NAME/KEY: misc_feature
<222> LOCATION: (10)..(11)
<223> OTHER INFORMATION: residues 10 and 11 are separated by Spacer 9

<400> SEQUENCE: 29
uagcggaugc cc                                                       12

<210> SEQ ID NO 30
<211> LENGTH: 21
<212> TYPE: DNA
<213> ORGANISM: artificial
<220> FEATURE:
<223> OTHER INFORMATION: oligonucleotide for phage library construction

<400> SEQUENCE: 30
cagatcgagt ccaagaccgc c                                             21

<210> SEQ ID NO 31
<211> LENGTH: 21
<212> TYPE: DNA
<213> ORGANISM: artificial
<220> FEATURE:
<223> OTHER INFORMATION: oligonucleotide for phage library construction

<400> SEQUENCE: 31
caccagttcg ttgatggtgg c                                             21

<210> SEQ ID NO 32
<211> LENGTH: 39
<212> TYPE: DNA
<213> ORGANISM: artificial
<220> FEATURE:
<223> OTHER INFORMATION: oligonucleotide primer

<400> SEQUENCE: 32
aataataaga attctgtgaa gcagatcgag tccaagacc                          39

<210> SEQ ID NO 33
```

```
<211> LENGTH: 48
<212> TYPE: DNA
<213> ORGANISM: artificial
<220> FEATURE:
<223> OTHER INFORMATION: oligonucleotide primer

<400> SEQUENCE: 33
taataagcta gcaccaccag gcgccaccag ttcgttgatg gtggcctc                  48

<210> SEQ ID NO 34
<211> LENGTH: 4
<212> TYPE: PRT
<213> ORGANISM: artificial
<220> FEATURE:
<223> OTHER INFORMATION: peptide within loop 5

<400> SEQUENCE: 34

Ser Gly Ala Asn
1

<210> SEQ ID NO 35
<211> LENGTH: 9
<212> TYPE: PRT
<213> ORGANISM: artificial
<220> FEATURE:
<223> OTHER INFORMATION: loop sequence of binder peptides

<400> SEQUENCE: 35

Gln Trp Trp Gly Trp Ile Asp Gly Gln
1               5

<210> SEQ ID NO 36
<211> LENGTH: 9
<212> TYPE: PRT
<213> ORGANISM: artificial
<220> FEATURE:
<223> OTHER INFORMATION: loop sequence of binder peptides

<400> SEQUENCE: 36

Tyr Pro Leu Phe Gly Met Ala Ala Leu
1               5

<210> SEQ ID NO 37
<211> LENGTH: 9
<212> TYPE: PRT
<213> ORGANISM: artificial
<220> FEATURE:
<223> OTHER INFORMATION: loop sequence of binder peptides

<400> SEQUENCE: 37

Gln Cys Asn Thr Gly Glu Ser His Asp
1               5

<210> SEQ ID NO 38
<211> LENGTH: 9
<212> TYPE: PRT
<213> ORGANISM: artificial
<220> FEATURE:
<223> OTHER INFORMATION: loop sequence of binder peptides

<400> SEQUENCE: 38

Trp Ser Pro Leu Ile Met Cys Thr Met
1               5

<210> SEQ ID NO 39
<211> LENGTH: 9
<212> TYPE: PRT
```

<213> ORGANISM: artificial
<220> FEATURE:
<223> OTHER INFORMATION: loop sequence of binder peptides

<400> SEQUENCE: 39

Asn Thr Ile Lys His Gly Gly Ser Arg
1               5

<210> SEQ ID NO 40
<211> LENGTH: 9
<212> TYPE: PRT
<213> ORGANISM: artificial
<220> FEATURE:
<223> OTHER INFORMATION: loop sequence of binder peptides

<400> SEQUENCE: 40

Glu Lys Gly Ile Leu Val Ser Pro Leu
1               5

<210> SEQ ID NO 41
<211> LENGTH: 9
<212> TYPE: PRT
<213> ORGANISM: artificial
<220> FEATURE:
<223> OTHER INFORMATION: loop sequence of binder peptides

<400> SEQUENCE: 41

Lys Glu Arg Asp Ser Ala Trp Asp Asp
1               5

<210> SEQ ID NO 42
<211> LENGTH: 9
<212> TYPE: PRT
<213> ORGANISM: artificial
<220> FEATURE:
<223> OTHER INFORMATION: loop sequence of binder peptides

<400> SEQUENCE: 42

Phe Tyr Trp Ser Tyr Pro Ser Leu Pro
1               5

<210> SEQ ID NO 43
<211> LENGTH: 9
<212> TYPE: PRT
<213> ORGANISM: artificial
<220> FEATURE:
<223> OTHER INFORMATION: loop sequence of binder peptides

<400> SEQUENCE: 43

Gly Arg Cys Tyr Val Asp Gly Arg Leu
1               5

<210> SEQ ID NO 44
<211> LENGTH: 9
<212> TYPE: PRT
<213> ORGANISM: artificial
<220> FEATURE:
<223> OTHER INFORMATION: loop sequence of binder peptides

<400> SEQUENCE: 44

Lys Arg Met Leu Cys Leu Val Arg Thr
1               5

<210> SEQ ID NO 45
<211> LENGTH: 9
<212> TYPE: PRT
<213> ORGANISM: artificial

```
<220> FEATURE:
<223> OTHER INFORMATION: loop sequence of binder peptides

<400> SEQUENCE: 45

Val Thr Cys Asp His Glu Gly Cys Lys
1               5

<210> SEQ ID NO 46
<211> LENGTH: 9
<212> TYPE: PRT
<213> ORGANISM: artificial
<220> FEATURE:
<223> OTHER INFORMATION: loop sequence of binder peptides

<400> SEQUENCE: 46

Ser Asn Phe Ala Val Thr Phe Phe Phe
1               5

<210> SEQ ID NO 47
<211> LENGTH: 9
<212> TYPE: PRT
<213> ORGANISM: artificial
<220> FEATURE:
<223> OTHER INFORMATION: loop sequence of binder peptides

<400> SEQUENCE: 47

Ser Ala Arg Val Trp Ser Cys Ile Pro
1               5

<210> SEQ ID NO 48
<211> LENGTH: 9
<212> TYPE: PRT
<213> ORGANISM: artificial
<220> FEATURE:
<223> OTHER INFORMATION: loop sequence of binder peptides

<400> SEQUENCE: 48

Ser Arg Pro Leu Thr Leu Ile Arg Ser
1               5

<210> SEQ ID NO 49
<211> LENGTH: 9
<212> TYPE: PRT
<213> ORGANISM: artificial
<220> FEATURE:
<223> OTHER INFORMATION: loop sequence of binder peptides

<400> SEQUENCE: 49

Pro Lys Ala Arg Thr Lys Arg Asn Ser
1               5

<210> SEQ ID NO 50
<211> LENGTH: 9
<212> TYPE: PRT
<213> ORGANISM: artificial
<220> FEATURE:
<223> OTHER INFORMATION: loop sequence of binder peptides

<400> SEQUENCE: 50

Met Ile Phe Gly Arg Leu Val Ile Ile
1               5

<210> SEQ ID NO 51
<211> LENGTH: 9
<212> TYPE: PRT
<213> ORGANISM: artificial
<220> FEATURE:
```

<223> OTHER INFORMATION: loop sequence of binder peptides

<400> SEQUENCE: 51

Asn Arg Arg Pro Gln Arg Asn Ala Lys
1               5

<210> SEQ ID NO 52
<211> LENGTH: 9
<212> TYPE: PRT
<213> ORGANISM: artificial
<220> FEATURE:
<223> OTHER INFORMATION: loop sequence of binder peptides

<400> SEQUENCE: 52

Leu Met Leu Phe Phe Ser Arg Ile Ile
1               5

<210> SEQ ID NO 53
<211> LENGTH: 9
<212> TYPE: PRT
<213> ORGANISM: artificial
<220> FEATURE:
<223> OTHER INFORMATION: loop sequence of binder peptides

<400> SEQUENCE: 53

Lys Arg Asn Asp Asn Thr Ser Asp Thr
1               5

<210> SEQ ID NO 54
<211> LENGTH: 9
<212> TYPE: PRT
<213> ORGANISM: artificial
<220> FEATURE:
<223> OTHER INFORMATION: loop sequence of binder peptides

<400> SEQUENCE: 54

Phe Arg Arg Trp Asn Ser Arg Trp Gly
1               5

<210> SEQ ID NO 55
<211> LENGTH: 9
<212> TYPE: PRT
<213> ORGANISM: artificial
<220> FEATURE:
<223> OTHER INFORMATION: loop sequence of binder peptides

<400> SEQUENCE: 55

Gly Asp Glu Gln Leu Val Gly Arg Arg
1               5

<210> SEQ ID NO 56
<211> LENGTH: 9
<212> TYPE: PRT
<213> ORGANISM: artificial
<220> FEATURE:
<223> OTHER INFORMATION: loop sequence of binder peptides

<400> SEQUENCE: 56

Arg Asp Pro Asn Asn Cys Arg Gly Thr
1               5

<210> SEQ ID NO 57
<211> LENGTH: 9
<212> TYPE: PRT
<213> ORGANISM: artificial
<220> FEATURE:
<223> OTHER INFORMATION: loop sequence of binder peptides

```
<400> SEQUENCE: 57

Cys Val Leu Tyr Ser Val Gly Tyr Ala
1               5

<210> SEQ ID NO 58
<211> LENGTH: 9
<212> TYPE: PRT
<213> ORGANISM: artificial
<220> FEATURE:
<223> OTHER INFORMATION: loop sequence of binder peptides

<400> SEQUENCE: 58

Lys Glu Pro Thr Val Ile Gly Phe Trp
1               5

<210> SEQ ID NO 59
<211> LENGTH: 9
<212> TYPE: PRT
<213> ORGANISM: artificial
<220> FEATURE:
<223> OTHER INFORMATION: loop sequence of binder peptides

<400> SEQUENCE: 59

Leu Ser Pro Leu Phe Asn Phe Pro Leu
1               5

<210> SEQ ID NO 60
<211> LENGTH: 9
<212> TYPE: PRT
<213> ORGANISM: artificial
<220> FEATURE:
<223> OTHER INFORMATION: loop sequence of binder peptides

<400> SEQUENCE: 60

Asn Val Arg Glu Ser His Lys Arg Gly
1               5

<210> SEQ ID NO 61
<211> LENGTH: 9
<212> TYPE: PRT
<213> ORGANISM: artificial
<220> FEATURE:
<223> OTHER INFORMATION: loop sequence of binder peptides

<400> SEQUENCE: 61

Val Ser Met Phe Val Leu Asp Ser Trp
1               5

<210> SEQ ID NO 62
<211> LENGTH: 9
<212> TYPE: PRT
<213> ORGANISM: artificial
<220> FEATURE:
<223> OTHER INFORMATION: loop sequence of binder peptides

<400> SEQUENCE: 62

Asn Arg Asn Gly Glu Lys His Ala His
1               5

<210> SEQ ID NO 63
<211> LENGTH: 9
<212> TYPE: PRT
<213> ORGANISM: artificial
<220> FEATURE:
<223> OTHER INFORMATION: loop sequence of binder peptides
```

```
<400> SEQUENCE: 63

Gly Leu Leu Trp Ser Ile Pro Phe Arg
1               5

<210> SEQ ID NO 64
<211> LENGTH: 9
<212> TYPE: PRT
<213> ORGANISM: artificial
<220> FEATURE:
<223> OTHER INFORMATION: loop sequence of binder peptides

<400> SEQUENCE: 64

Thr Arg Asp Trp Asn Arg Asp Val Asn
1               5

<210> SEQ ID NO 65
<211> LENGTH: 9
<212> TYPE: PRT
<213> ORGANISM: artificial
<220> FEATURE:
<223> OTHER INFORMATION: loop sequence of binder peptides

<400> SEQUENCE: 65

Gln Leu Thr Leu Ser Ile Pro Phe Arg
1               5

<210> SEQ ID NO 66
<211> LENGTH: 7
<212> TYPE: PRT
<213> ORGANISM: artificial
<220> FEATURE:
<223> OTHER INFORMATION: loop sequence of binder peptides

<400> SEQUENCE: 66

Ser Glu Ala Asn Gly Glu Glu
1               5

<210> SEQ ID NO 67
<211> LENGTH: 9
<212> TYPE: PRT
<213> ORGANISM: artificial
<220> FEATURE:
<223> OTHER INFORMATION: loop sequence of binder peptides

<400> SEQUENCE: 67

Leu Arg Val Trp Ser Ile Pro Glu Arg
1               5

<210> SEQ ID NO 68
<211> LENGTH: 9
<212> TYPE: PRT
<213> ORGANISM: artificial
<220> FEATURE:
<223> OTHER INFORMATION: loop sequence of binder peptides

<400> SEQUENCE: 68

His Thr Asn Glu Ser Arg Asp Gly Asn
1               5

<210> SEQ ID NO 69
<211> LENGTH: 9
<212> TYPE: PRT
<213> ORGANISM: artificial
<220> FEATURE:
<223> OTHER INFORMATION: loop sequence of binder peptides

<400> SEQUENCE: 69
```

```
Glu Leu Ile Trp Ser Leu Pro Glu Arg
1               5

<210> SEQ ID NO 70
<211> LENGTH: 9
<212> TYPE: PRT
<213> ORGANISM: artificial
<220> FEATURE:
<223> OTHER INFORMATION: loop sequence of binder peptides

<400> SEQUENCE: 70

Gly Gln Asn Arg Lys Arg Thr Glu Asp
1               5

<210> SEQ ID NO 71
<211> LENGTH: 9
<212> TYPE: PRT
<213> ORGANISM: artificial
<220> FEATURE:
<223> OTHER INFORMATION: loop sequence of binder peptides

<400> SEQUENCE: 71

Ala Ile Leu Ile Ser Leu Pro Glu Arg
1               5

<210> SEQ ID NO 72
<211> LENGTH: 3
<212> TYPE: PRT
<213> ORGANISM: artificial
<220> FEATURE:
<223> OTHER INFORMATION: loop sequence of binder peptides

<400> SEQUENCE: 72

Arg Gly Pro
1

<210> SEQ ID NO 73
<211> LENGTH: 9
<212> TYPE: PRT
<213> ORGANISM: artificial
<220> FEATURE:
<223> OTHER INFORMATION: loop sequence of binder peptides

<400> SEQUENCE: 73

Phe His Ala Ser Phe Val Pro Leu Arg
1               5

<210> SEQ ID NO 74
<211> LENGTH: 4
<212> TYPE: PRT
<213> ORGANISM: artificial
<220> FEATURE:
<223> OTHER INFORMATION: loop sequence of binder peptides

<400> SEQUENCE: 74

Gln His Lys Pro
1

<210> SEQ ID NO 75
<211> LENGTH: 9
<212> TYPE: PRT
<213> ORGANISM: artificial
<220> FEATURE:
<223> OTHER INFORMATION: loop sequence of binder peptides

<400> SEQUENCE: 75
```

```
Ser Tyr Val Tyr Ala Leu Pro Arg Arg
1               5
```

```
<210> SEQ ID NO 76
<211> LENGTH: 9
<212> TYPE: PRT
<213> ORGANISM: artificial
<220> FEATURE:
<223> OTHER INFORMATION: loop sequence of binder peptides

<400> SEQUENCE: 76

Cys Gly Arg Tyr Glu Glu Gly Arg Arg
1               5
```

```
<210> SEQ ID NO 77
<211> LENGTH: 9
<212> TYPE: PRT
<213> ORGANISM: artificial
<220> FEATURE:
<223> OTHER INFORMATION: loop sequence of binder peptides

<400> SEQUENCE: 77

Leu Pro Leu Val Tyr Phe Cys Pro Tyr
1               5
```

```
<210> SEQ ID NO 78
<211> LENGTH: 9
<212> TYPE: PRT
<213> ORGANISM: artificial
<220> FEATURE:
<223> OTHER INFORMATION: loop sequence of binder peptides

<400> SEQUENCE: 78

Gly Cys Val Arg Thr Met Ala Arg Arg
1               5
```

```
<210> SEQ ID NO 79
<211> LENGTH: 9
<212> TYPE: PRT
<213> ORGANISM: artificial
<220> FEATURE:
<223> OTHER INFORMATION: loop sequence of binder peptides

<400> SEQUENCE: 79

Met Ser Ser Asn Lys Tyr Ile Cys Phe
1               5
```

```
<210> SEQ ID NO 80
<211> LENGTH: 9
<212> TYPE: PRT
<213> ORGANISM: artificial
<220> FEATURE:
<223> OTHER INFORMATION: loop sequence of binder peptides

<400> SEQUENCE: 80

Cys Val Val Thr Thr Gly Asp Ser Lys
1               5
```

```
<210> SEQ ID NO 81
<211> LENGTH: 9
<212> TYPE: PRT
<213> ORGANISM: artificial
<220> FEATURE:
<223> OTHER INFORMATION: loop sequence of binder peptides

<400> SEQUENCE: 81

Thr Arg Glu Leu Leu Pro Tyr Cys Trp
```

```
<210> SEQ ID NO 82
<211> LENGTH: 9
<212> TYPE: PRT
<213> ORGANISM: artificial
<220> FEATURE:
<223> OTHER INFORMATION: loop sequence of binder peptides

<400> SEQUENCE: 82

Tyr Arg Thr His Thr Asn Glu Ile Arg
1               5

<210> SEQ ID NO 83
<211> LENGTH: 9
<212> TYPE: PRT
<213> ORGANISM: artificial
<220> FEATURE:
<223> OTHER INFORMATION: loop sequence of binder peptides

<400> SEQUENCE: 83

Arg Phe Leu Thr Leu Arg Ser Ser Ser
1               5

<210> SEQ ID NO 84
<211> LENGTH: 9
<212> TYPE: PRT
<213> ORGANISM: artificial
<220> FEATURE:
<223> OTHER INFORMATION: loop sequence of binder peptides

<400> SEQUENCE: 84

Ser Arg Gln Gly Gly Ile Cys Ser Arg
1               5

<210> SEQ ID NO 85
<211> LENGTH: 9
<212> TYPE: PRT
<213> ORGANISM: artificial
<220> FEATURE:
<223> OTHER INFORMATION: loop sequence of binder peptides

<400> SEQUENCE: 85

Arg Ile Ser Leu Trp Cys Ala Trp Thr
1               5

<210> SEQ ID NO 86
<211> LENGTH: 9
<212> TYPE: PRT
<213> ORGANISM: artificial
<220> FEATURE:
<223> OTHER INFORMATION: loop sequence of binder peptides

<400> SEQUENCE: 86

Gly Ser Ser Pro Glu Ser Arg Val His
1               5

<210> SEQ ID NO 87
<211> LENGTH: 9
<212> TYPE: PRT
<213> ORGANISM: artificial
<220> FEATURE:
<223> OTHER INFORMATION: loop sequence of binder peptides

<400> SEQUENCE: 87

Ala Cys Lys His Arg Val Cys Phe Phe
1               5
```

```
<210> SEQ ID NO 88
<211> LENGTH: 9
<212> TYPE: PRT
<213> ORGANISM: artificial
<220> FEATURE:
<223> OTHER INFORMATION: loop sequence of binder peptides

<400> SEQUENCE: 88

Asn Trp Ser Ser Ser Ser Gly Lys Asp
1               5

<210> SEQ ID NO 89
<211> LENGTH: 9
<212> TYPE: PRT
<213> ORGANISM: artificial
<220> FEATURE:
<223> OTHER INFORMATION: loop sequence of binder peptides

<400> SEQUENCE: 89

Arg Tyr Val Phe Pro Pro Glu Ala Val
1               5

<210> SEQ ID NO 90
<211> LENGTH: 9
<212> TYPE: PRT
<213> ORGANISM: artificial
<220> FEATURE:
<223> OTHER INFORMATION: loop sequence of binder peptides

<400> SEQUENCE: 90

Gln Cys Trp Ala Arg Arg Arg Asp Arg
1               5

<210> SEQ ID NO 91
<211> LENGTH: 9
<212> TYPE: PRT
<213> ORGANISM: artificial
<220> FEATURE:
<223> OTHER INFORMATION: loop sequence of binder peptides

<400> SEQUENCE: 91

Gly Pro Arg Asn Thr Leu Leu Cys Phe
1               5

<210> SEQ ID NO 92
<211> LENGTH: 9
<212> TYPE: PRT
<213> ORGANISM: artificial
<220> FEATURE:
<223> OTHER INFORMATION: loop sequence of binder peptides

<400> SEQUENCE: 92

Asp Thr Thr Lys Asp Arg Gly Gly Thr
1               5

<210> SEQ ID NO 93
<211> LENGTH: 9
<212> TYPE: PRT
<213> ORGANISM: artificial
<220> FEATURE:
<223> OTHER INFORMATION: loop sequence of binder peptides

<400> SEQUENCE: 93

Leu Pro Trp Thr Val Gln Phe Gly Tyr
1               5
```

```
<210> SEQ ID NO 94
<211> LENGTH: 9
<212> TYPE: PRT
<213> ORGANISM: artificial
<220> FEATURE:
<223> OTHER INFORMATION: loop sequence of binder peptides

<400> SEQUENCE: 94

Gly Lys Val Cys Gly Gly Lys Arg Arg
1               5

<210> SEQ ID NO 95
<211> LENGTH: 9
<212> TYPE: PRT
<213> ORGANISM: artificial
<220> FEATURE:
<223> OTHER INFORMATION: loop sequence of binder peptides

<400> SEQUENCE: 95

Ala Arg Pro His Phe Cys Pro Val Met
1               5

<210> SEQ ID NO 96
<211> LENGTH: 9
<212> TYPE: PRT
<213> ORGANISM: artificial
<220> FEATURE:
<223> OTHER INFORMATION: loop sequence of binder peptides

<400> SEQUENCE: 96

Arg Asp Ala Arg Ala Ala Pro Pro Ser
1               5

<210> SEQ ID NO 97
<211> LENGTH: 9
<212> TYPE: PRT
<213> ORGANISM: artificial
<220> FEATURE:
<223> OTHER INFORMATION: loop sequence of binder peptides

<400> SEQUENCE: 97

Leu Pro Trp Pro Ser Tyr Phe Gly Leu
1               5

<210> SEQ ID NO 98
<211> LENGTH: 9
<212> TYPE: PRT
<213> ORGANISM: artificial
<220> FEATURE:
<223> OTHER INFORMATION: loop sequence of binder peptides

<400> SEQUENCE: 98

Trp Asn Thr Arg Ala His Cys Ser Arg
1               5

<210> SEQ ID NO 99
<211> LENGTH: 9
<212> TYPE: PRT
<213> ORGANISM: artificial
<220> FEATURE:
<223> OTHER INFORMATION: loop sequence of binder peptides

<400> SEQUENCE: 99

Leu Leu Pro Pro Leu Cys Thr Ile Asp
1               5
```

```
<210> SEQ ID NO 100
<211> LENGTH: 9
<212> TYPE: PRT
<213> ORGANISM: artificial
<220> FEATURE:
<223> OTHER INFORMATION: loop sequence of binder peptides

<400> SEQUENCE: 100

Lys Glu Asn Asn Gly Trp Arg Gly Asn
1               5

<210> SEQ ID NO 101
<211> LENGTH: 9
<212> TYPE: PRT
<213> ORGANISM: artificial
<220> FEATURE:
<223> OTHER INFORMATION: loop sequence of binder peptides

<400> SEQUENCE: 101

Met Ala Gly Pro Arg Val Met Gly Pro
1               5

<210> SEQ ID NO 102
<211> LENGTH: 9
<212> TYPE: PRT
<213> ORGANISM: artificial
<220> FEATURE:
<223> OTHER INFORMATION: loop sequence of binder peptides

<400> SEQUENCE: 102

Asn Lys Arg Gly Glu Gly Trp Gln Lys
1               5

<210> SEQ ID NO 103
<211> LENGTH: 9
<212> TYPE: PRT
<213> ORGANISM: artificial
<220> FEATURE:
<223> OTHER INFORMATION: loop sequence of binder peptides

<400> SEQUENCE: 103

Ser Val Ile Met Trp Pro Gln Leu Trp
1               5

<210> SEQ ID NO 104
<211> LENGTH: 9
<212> TYPE: PRT
<213> ORGANISM: artificial
<220> FEATURE:
<223> OTHER INFORMATION: loop sequence of binder peptides

<400> SEQUENCE: 104

Cys Tyr Ala Val Arg Glu Gly Gln Gly
1               5

<210> SEQ ID NO 105
<211> LENGTH: 9
<212> TYPE: PRT
<213> ORGANISM: artificial
<220> FEATURE:
<223> OTHER INFORMATION: loop sequence of binder peptides

<400> SEQUENCE: 105

Leu Tyr Thr Ala Leu Leu Tyr Cys Thr
1               5

<210> SEQ ID NO 106
```

```
<211> LENGTH: 9
<212> TYPE: PRT
<213> ORGANISM: artificial
<220> FEATURE:
<223> OTHER INFORMATION: loop sequence of binder peptides

<400> SEQUENCE: 106

Ala Trp Leu Thr Pro Asn Arg Val Pro
1               5

<210> SEQ ID NO 107
<211> LENGTH: 9
<212> TYPE: PRT
<213> ORGANISM: artificial
<220> FEATURE:
<223> OTHER INFORMATION: loop sequence of binder peptides

<400> SEQUENCE: 107

Ser Ala Asn Ser Gly Trp Cys Cys Gly
1               5

<210> SEQ ID NO 108
<211> LENGTH: 9
<212> TYPE: PRT
<213> ORGANISM: artificial
<220> FEATURE:
<223> OTHER INFORMATION: loop sequence of binder peptides

<400> SEQUENCE: 108

Leu Asp Ile Glu Ser Phe Leu Tyr Phe
1               5

<210> SEQ ID NO 109
<211> LENGTH: 9
<212> TYPE: PRT
<213> ORGANISM: artificial
<220> FEATURE:
<223> OTHER INFORMATION: loop sequence of binder peptides

<400> SEQUENCE: 109

Glu Glu Lys Gly Tyr Glu Gly Arg Arg
1               5

<210> SEQ ID NO 110
<211> LENGTH: 9
<212> TYPE: PRT
<213> ORGANISM: artificial
<220> FEATURE:
<223> OTHER INFORMATION: loop sequence of binder peptides

<400> SEQUENCE: 110

Tyr Val Pro Phe Ser Leu Ser Gly Tyr
1               5

<210> SEQ ID NO 111
<211> LENGTH: 9
<212> TYPE: PRT
<213> ORGANISM: artificial
<220> FEATURE:
<223> OTHER INFORMATION: loop sequence of binder peptides

<400> SEQUENCE: 111

Arg Tyr Glu Glu Thr Thr Arg Gln His
1               5

<210> SEQ ID NO 112
<211> LENGTH: 9
```

```
<212> TYPE: PRT
<213> ORGANISM: artificial
<220> FEATURE:
<223> OTHER INFORMATION: loop sequence of binder peptides

<400> SEQUENCE: 112

Arg Val Ala Ser Lys Arg Ser Ala Phe
1               5

<210> SEQ ID NO 113
<211> LENGTH: 9
<212> TYPE: PRT
<213> ORGANISM: artificial
<220> FEATURE:
<223> OTHER INFORMATION: loop sequence of binder peptides

<400> SEQUENCE: 113

Lys Trp Glu Ser Pro Tyr Glu Ala Val
1               5

<210> SEQ ID NO 114
<211> LENGTH: 9
<212> TYPE: PRT
<213> ORGANISM: artificial
<220> FEATURE:
<223> OTHER INFORMATION: loop sequence of binder peptides

<400> SEQUENCE: 114

Leu Ser His Ser Val Pro Tyr Tyr Leu
1               5

<210> SEQ ID NO 115
<211> LENGTH: 9
<212> TYPE: PRT
<213> ORGANISM: artificial
<220> FEATURE:
<223> OTHER INFORMATION: loop sequence of binder peptides

<400> SEQUENCE: 115

Cys Gln Thr Gly Thr Lys Gln Leu Pro
1               5

<210> SEQ ID NO 116
<211> LENGTH: 9
<212> TYPE: PRT
<213> ORGANISM: artificial
<220> FEATURE:
<223> OTHER INFORMATION: loop sequence of binder peptides

<400> SEQUENCE: 116

Phe Gly His Phe Gly Phe Pro Thr Leu
1               5

<210> SEQ ID NO 117
<211> LENGTH: 9
<212> TYPE: PRT
<213> ORGANISM: artificial
<220> FEATURE:
<223> OTHER INFORMATION: loop sequence of binder peptides

<400> SEQUENCE: 117

Arg Ser Glu Asn Asp Arg Trp Asn Glu
1               5

<210> SEQ ID NO 118
<211> LENGTH: 9
<212> TYPE: PRT
```

```
<213> ORGANISM: artificial
<220> FEATURE:
<223> OTHER INFORMATION: loop sequence of binder peptides

<400> SEQUENCE: 118

Leu Ile Ala Gly Pro Phe Trp Tyr Ser
1               5

<210> SEQ ID NO 119
<211> LENGTH: 9
<212> TYPE: PRT
<213> ORGANISM: artificial
<220> FEATURE:
<223> OTHER INFORMATION: loop sequence of binder peptides

<400> SEQUENCE: 119

Lys Asn Glu Lys Arg Asp Val Ala Glu
1               5

<210> SEQ ID NO 120
<211> LENGTH: 9
<212> TYPE: PRT
<213> ORGANISM: artificial
<220> FEATURE:
<223> OTHER INFORMATION: loop sequence of binder peptides

<400> SEQUENCE: 120

Phe Gly Phe Phe Gly Phe Pro Val Leu
1               5

<210> SEQ ID NO 121
<211> LENGTH: 9
<212> TYPE: PRT
<213> ORGANISM: artificial
<220> FEATURE:
<223> OTHER INFORMATION: loop sequence of binder peptides

<400> SEQUENCE: 121

Arg Arg Asn Glu Arg Ala Arg Asp Trp
1               5

<210> SEQ ID NO 122
<211> LENGTH: 9
<212> TYPE: PRT
<213> ORGANISM: artificial
<220> FEATURE:
<223> OTHER INFORMATION: loop sequence of binder peptides

<400> SEQUENCE: 122

Leu Ala Ala Gly Pro Phe Tyr Leu Leu
1               5

<210> SEQ ID NO 123
<211> LENGTH: 9
<212> TYPE: PRT
<213> ORGANISM: artificial
<220> FEATURE:
<223> OTHER INFORMATION: loop sequence of binder peptides

<400> SEQUENCE: 123

Gly Gly Thr Pro Gly Arg Arg Asn Arg
1               5

<210> SEQ ID NO 124
<211> LENGTH: 9
<212> TYPE: PRT
<213> ORGANISM: artificial
```

```
<220> FEATURE:
<223> OTHER INFORMATION: loop sequence of binder peptides

<400> SEQUENCE: 124

Phe Cys Glu Phe Cys Phe Pro Phe Leu
1               5

<210> SEQ ID NO 125
<211> LENGTH: 9
<212> TYPE: PRT
<213> ORGANISM: artificial
<220> FEATURE:
<223> OTHER INFORMATION: loop sequence of binder peptides

<400> SEQUENCE: 125

Arg Leu Arg Thr Gly Gly His Pro Tyr
1               5

<210> SEQ ID NO 126
<211> LENGTH: 9
<212> TYPE: PRT
<213> ORGANISM: artificial
<220> FEATURE:
<223> OTHER INFORMATION: loop sequence of binder peptides

<400> SEQUENCE: 126

Val Tyr Val Ser Leu Ser Arg His Arg
1               5

<210> SEQ ID NO 127
<211> LENGTH: 9
<212> TYPE: PRT
<213> ORGANISM: artificial
<220> FEATURE:
<223> OTHER INFORMATION: loop sequence of binder peptides

<400> SEQUENCE: 127

Asp Arg Lys Pro Trp Lys Thr Arg Gly
1               5

<210> SEQ ID NO 128
<211> LENGTH: 9
<212> TYPE: PRT
<213> ORGANISM: artificial
<220> FEATURE:
<223> OTHER INFORMATION: loop sequence of binder peptides

<400> SEQUENCE: 128

Phe Gly Leu Phe Ser Phe Pro Leu Leu
1               5

<210> SEQ ID NO 129
<211> LENGTH: 97
<212> TYPE: PRT
<213> ORGANISM: Homo sapiens

<400> SEQUENCE: 129

Gly Ser Ala Arg Val Leu Val Leu Ser Ala Ile Asp Ser Ala Lys Thr
1               5                   10                  15

Ser Ile Arg Met Met Ala Tyr Ser Phe Thr Ala Pro Ile Met Lys
            20                  25                  30

Ala Leu Val Ala Ala Lys Lys Arg Gly Val Asp Val Lys Ile Val Ile
                35                  40                  45

Asp Glu Arg Gly Asn Thr Gly Arg Ala Ser Ile Ala Ala Met Asn Tyr
        50                  55                  60
```

```
Ile Ala Asn Ser Gly Ile Pro Leu Arg Thr Asp Ser Asn Phe Pro Ile
 65                  70                  75                  80

Gln His Asp Lys Val Ile Val Asp Asn Val Thr Val Glu Thr Gly
                 85                  90                  95

Ser

<210> SEQ ID NO 130
<211> LENGTH: 142
<212> TYPE: PRT
<213> ORGANISM: Homo sapiens

<400> SEQUENCE: 130

Asn Pro Glu Glu Ser Ala Leu Arg Ala Leu Val Ala Ser Ala Lys Gly
 1               5                  10                  15

His Ile Glu Ile Ser Gln Gln Asp Leu Asn Ala Thr Cys Pro Pro Leu
                20                  25                  30

Pro Arg Tyr Asp Ile Arg Leu Tyr Asp Ala Leu Ala Ala Lys Met Ala
             35                  40                  45

Ala Gly Val Lys Val Arg Ile Val Val Ser Asp Pro Ala Asn Arg Gly
 50                  55                  60

Ala Val Gly Ser Gly Gly Tyr Ser Gln Ile Lys Ser Leu Ser Glu Ile
 65                  70                  75                  80

Ser Asp Thr Leu Arg Asn Arg Leu Ala Asn Ile Thr Gly Gly Gln Gln
                 85                  90                  95

Ala Ala Lys Thr Ala Met Cys Ser Asn Leu Gln Leu Ala Thr Phe Arg
            100                 105                 110

Ser Ser Pro Asn Gly Lys Trp Ala Asp Gly His Pro Tyr Ala Gln His
        115                 120                 125

His Lys Leu Val Ser Val Asp Ser Ser Thr Phe Tyr Ile Gly
    130                 135                 140

<210> SEQ ID NO 131
<211> LENGTH: 118
<212> TYPE: PRT
<213> ORGANISM: Homo sapiens

<400> SEQUENCE: 131

Lys Arg Leu Leu Ala Lys Met Thr Glu Asn Ile Gly Asn Ala Thr Arg
 1               5                  10                  15

Thr Val Asp Ile Ser Thr Leu Ala Pro Phe Pro Asn Gly Ala Phe Gln
                20                  25                  30

Asp Ala Ile Val Ala Gly Leu Lys Glu Ser Ala Ala Lys Gly Asn Ser
             35                  40                  45

Leu Lys Val Arg Ile Leu Val Gly Ala Ala Pro Val Tyr His Met Asn
 50                  55                  60

Gly Ile Pro Ser Lys Tyr Arg Asp Lys Leu Thr Ala Lys Leu Gly Lys
 65                  70                  75                  80

Ala Ala Glu Asn Ile Thr Leu Asn Val Ala Ser Met Thr Thr Ser Lys
                 85                  90                  95

Thr Ala Phe Ser Trp Asn His Ser Lys Ile Leu Val Val Asp Gly Gln
            100                 105                 110

Ser Ala Leu Thr Gly Gly
        115

<210> SEQ ID NO 132
<211> LENGTH: 103
```

```
<212> TYPE: PRT
<213> ORGANISM: Homo sapiens
<220> FEATURE:
<221> NAME/KEY: misc_feature
<222> LOCATION: (88)..(89)
<223> OTHER INFORMATION: Xaa can be any naturally occurring amino acid

<400> SEQUENCE: 132

Asn Ser Gly Ala Leu His Ile Lys Asp Ile Leu Ser Pro Leu Phe Gly
1               5                   10                  15

Thr Leu Val Ser Ser Ala Gln Phe Asn Tyr Cys Phe Asp Val Asp Trp
            20                  25                  30

Leu Val Lys Gln Tyr Pro Pro Glu Phe Arg Lys Lys Pro Ile Leu Leu
        35                  40                  45

Val His Gly Asp Lys Arg Glu Ala Lys Ala His Leu His Ala Gln Ala
    50                  55                  60

Lys Pro Tyr Glu Asn Ile Ser Leu Cys Gln Ala Lys Leu Asp Ile Ala
65                  70                  75                  80

Phe Gly Thr His His Thr Lys Xaa Xaa Leu Leu Tyr Glu Glu Gly
                85                  90                  95

Leu Arg Val Val Ile His Thr
            100

<210> SEQ ID NO 133
<211> LENGTH: 146
<212> TYPE: PRT
<213> ORGANISM: Homo sapiens
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid

<400> SEQUENCE: 133

Asn Trp Gly His Phe Arg Leu Lys Lys Leu Leu Lys Asp His Ala Ser
1               5                   10                  15

Ser Xaa Pro Asn Ala Glu Ser Trp Pro Val Val Gly Gln Phe Ser Ser
            20                  25                  30

Val Gly Ser Leu Gly Ala Asp Glu Ser Lys Trp Leu Cys Ser Glu Phe
        35                  40                  45

Lys Glu Ser Xaa Leu Thr Leu Gly Lys Glu Ser Lys Thr Pro Gly Lys
    50                  55                  60

Ser Ser Val Pro Leu Tyr Leu Ile Tyr Pro Ser Val Glu Asn Val Arg
65                  70                  75                  80

Thr Ser Leu Glu Gly Tyr Pro Ala Gly Gly Ser Leu Pro Tyr Ser Ile
                85                  90                  95

Gln Thr Ala Glu Lys Gln Asn Trp Leu His Ser Tyr Phe His Lys Trp
            100                 105                 110

Ser Ala Glu Thr Ser Gly Arg Ser Asn Ala Xaa Pro His Ile Lys Thr
        115                 120                 125

Tyr Xaa Arg Pro Ser Pro Asp Phe Ser Lys Ile Ala Trp Phe Leu Val
```

```
                130                 135                 140

Thr Ser
145

<210> SEQ ID NO 134
<211> LENGTH: 128
<212> TYPE: PRT
<213> ORGANISM: Homo sapiens

<400> SEQUENCE: 134

Leu Cys Asp Ala Leu Asn Ala Trp Gln Leu Val Lys Glu Leu Lys Gln
1               5                   10                  15

Ala Leu Gly Ile Pro Ala Ala Ser Phe Lys His Val Ser Pro Ala
            20                  25                  30

Gly Ala Ala Val Gly Ile Pro Leu Ser Glu Glu Ala Gln Val Cys
        35                  40                  45

Met Val His Asp Leu His Lys Thr Leu Thr Pro Leu Ala Ser Ala Tyr
    50                  55                  60

Ala Arg Ser Arg Gly Ala Asp Arg Met Ser Ser Phe Gly Asp Phe Ile
65                  70                  75                  80

Ala Leu Ser Asp Ile Cys Asp Val Pro Thr Ala Lys Ile Ile Ser Arg
                85                  90                  95

Glu Val Ser Asp Gly Val Val Ala Pro Gly Tyr Glu Glu Ala Leu
            100                 105                 110

Lys Ile Leu Ser Lys Lys Lys Asn Gly Gly Tyr Cys Val Leu Gln Met
        115                 120                 125

<210> SEQ ID NO 135
<211> LENGTH: 171
<212> TYPE: PRT
<213> ORGANISM: Homo sapiens

<400> SEQUENCE: 135

Val Arg Asp Leu Ile Val Ala Ser Ile Ala Val Lys Tyr Thr Gln Ser
1               5                   10                  15

Asn Ser Val Cys Tyr Ala Lys Asp Gly Gln Val Ile Gly Ile Gly Ala
            20                  25                  30

Gly Gln Gln Ser Arg Ile His Cys Thr Arg Leu Ala Gly Asp Lys Ala
        35                  40                  45

Asn Ser Trp Trp Leu Arg His His Pro Arg Val Leu Ser Met Lys Phe
    50                  55                  60

Lys Ala Gly Val Lys Arg Ala Glu Val Ser Asn Ala Ile Asp Gln Tyr
65                  70                  75                  80

Val Thr Gly Thr Ile Gly Glu Asp Glu Asp Leu Val Lys Trp Gln Ala
                85                  90                  95

Met Phe Glu Glu Val Pro Ala Gln Leu Thr Glu Ala Glu Lys Lys Gln
            100                 105                 110

Trp Ile Ala Lys Leu Thr Ala Val Ser Leu Ser Ser Asp Ala Phe Phe
        115                 120                 125

Pro Phe Arg Asp Asn Val Asp Arg Ala Lys Arg Ile Gly Val Gln Phe
    130                 135                 140

Ile Val Ala Pro Ser Gly Ser Ala Ala Asp Val Val Ile Glu Ala
145                 150                 155                 160

Cys Asn Glu Leu Gly Ile Thr Leu Ile His Thr
                165                 170
```

-continued

```
<210> SEQ ID NO 136
<211> LENGTH: 139
<212> TYPE: PRT
<213> ORGANISM: Homo sapiens

<400> SEQUENCE: 136

Asp Gly Arg Phe Arg Ile Ile Val Phe Ala Gly Lys Ala Thr Asp Ala
1               5                   10                  15

Thr Gln Met Ser Arg Ile Lys Lys Phe Ser Ala Tyr Leu Asp Ser Glu
            20                  25                  30

Asn Ser Val Ile Ser Leu Tyr Thr Pro Lys Val Ser Asp Arg Asn Ser
        35                  40                  45

Arg Ile Asp Val Ile Thr Ile His Ser Cys His Arg Asp Ile Glu
    50                  55                  60

Met His Asp Phe Pro Ala Pro Ala Leu His Pro Lys Trp Gln Tyr Asp
65                  70                  75                  80

Phe Ile Tyr Ala Asp Cys Asp Ser Trp His His Pro His Pro Lys Ser
                85                  90                  95

Tyr Gln Ala Trp Gly Val Asp Glu Thr Lys Gly Ala Val Val Val
            100                 105                 110

Arg Pro Asp Gly Tyr Thr Ser Leu Val Thr Asp Leu Glu Gly Thr Ala
            115                 120                 125

Glu Ile Asp Arg Tyr Phe Ser Gly Ile Leu Val
    130                 135

<210> SEQ ID NO 137
<211> LENGTH: 161
<212> TYPE: PRT
<213> ORGANISM: Homo sapiens
<220> FEATURE:
<221> NAME/KEY: misc_feature
<222> LOCATION: (13)..(13)
<223> OTHER INFORMATION: Xaa can be any naturally occurring amino acid

<400> SEQUENCE: 137

Gly Lys Val Leu Leu Ile Glu Asn Val Ala Ser Leu Xaa Gly Thr Thr
1               5                   10                  15

Val Arg Asp Tyr Thr Gln Met Asn Asp Leu Gln Arg Arg Leu Gly Pro
            20                  25                  30

Arg Gly Leu Val Val Leu Gly Phe Pro Cys Asn Gln Phe Gly His Gln
        35                  40                  45

Glu Asn Ala Lys Asn Glu Glu Ile Leu Asn Cys Leu Lys Tyr Val Arg
    50                  55                  60

Pro Gly Gly Gly Phe Glu Pro Asn Phe Met Leu Phe Glu Lys Cys Glu
65                  70                  75                  80

Val Asn Gly Glu Lys Ala His Pro Leu Phe Ala Phe Leu Arg Glu Val
                85                  90                  95

Leu Pro Thr Pro Ser Asp Asp Ala Thr Ala Leu Met Thr Asp Pro Lys
            100                 105                 110

Phe Ile Thr Trp Ser Pro Val Cys Arg Asn Asp Val Ser Trp Asn Phe
        115                 120                 125

Glu Lys Phe Leu Val Gly Pro Asp Gly Val Pro Val Arg Arg Tyr Ser
    130                 135                 140

Arg Arg Phe Leu Thr Ile Asp Ile Glu Pro Asp Ile Glu Thr Leu Leu
145                 150                 155                 160

Ser
```

```
<210> SEQ ID NO 138
<211> LENGTH: 114
<212> TYPE: PRT
<213> ORGANISM: Homo sapiens

<400> SEQUENCE: 138

Gly Lys Val Ser Leu Val Asn Val Trp Ala Ser Trp Cys Val Pro Cys
1               5                   10                  15

His Asp Glu Ala Pro Leu Leu Thr Glu Leu Gly Lys Asp Lys Arg Phe
            20                  25                  30

Gln Leu Val Gly Ile Asn Tyr Lys Asp Ala Ala Asp Asn Ala Arg Arg
        35                  40                  45

Phe Leu Gly Arg Tyr Gly Asn Pro Phe Gly Arg Val Gly Val Asp Ala
    50                  55                  60

Asn Gly Arg Ala Ser Ile Glu Trp Gly Val Tyr Gly Val Pro Glu Thr
65                  70                  75                  80

Phe Val Val Gly Arg Glu Gly Thr Ile Val Tyr Lys Leu Val Gly Pro
                85                  90                  95

Ile Thr Pro Asp Asn Leu Arg Ser Val Leu Pro Gln Met Glu Lys
            100                 105                 110

Ala Leu

<210> SEQ ID NO 139
<211> LENGTH: 121
<212> TYPE: PRT
<213> ORGANISM: Homo sapiens

<400> SEQUENCE: 139

Gly Lys Thr Leu Leu Val Asn Leu Trp Ala Thr Trp Cys Val Pro Cys
1               5                   10                  15

Arg Lys Glu Met Pro Ala Leu Asp Glu Leu Gln Gly Lys Leu Ser Gly
            20                  25                  30

Pro Asn Phe Glu Val Val Ala Ile Asn Ile Asp Thr Arg Asp Pro Glu
        35                  40                  45

Lys Pro Lys Thr Phe Leu Lys Glu Ala Asn Leu Thr Arg Leu Gly Tyr
    50                  55                  60

Phe Asn Asp Gln Lys Ala Lys Val Phe Gln Asp Leu Lys Ala Ile Gly
65                  70                  75                  80

Arg Ala Leu Gly Met Pro Thr Ser Val Leu Val Asp Pro Gln Gly Cys
                85                  90                  95

Glu Ile Ala Thr Ile Ala Gly Pro Ala Glu Trp Ala Ser Glu Asp Ala
            100                 105                 110

Leu Lys Leu Ile Arg Ala Ala Thr Gly
        115                 120

<210> SEQ ID NO 140
<211> LENGTH: 149
<212> TYPE: PRT
<213> ORGANISM: Homo sapiens
<220> FEATURE:
<221> NAME/KEY: misc_feature
<222> LOCATION: (17)..(17)
<223> OTHER INFORMATION: Xaa can be any naturally occurring amino acid

<400> SEQUENCE: 140

Asp Ser Trp Gly Ile Leu Phe Ser His Pro Arg Asp Phe Thr Pro Val
1               5                   10                  15

Xaa Thr Thr Glu Leu Gly Arg Ala Ala Lys Leu Ala Pro Glu Phe Ala
            20                  25                  30
```

```
Lys Arg Asn Val Lys Leu Ile Ala Leu Ser Ile Asp Ser Val Glu Asp
                35                  40                  45

His Leu Ala Trp Ser Lys Asp Ile Asn Ala Tyr Asn Ser Glu Glu Pro
 50                  55                  60

Thr Glu Lys Leu Pro Phe Pro Ile Ile Asp Asp Arg Asn Arg Glu Leu
 65                  70                  75                  80

Ala Ile Leu Leu Gly Met Leu Asp Pro Ala Glu Lys Asp Glu Lys Gly
                 85                  90                  95

Met Pro Val Thr Ala Arg Val Val Phe Val Phe Gly Pro Asp Lys Lys
                100                 105                 110

Leu Lys Leu Ser Ile Leu Tyr Pro Ala Thr Thr Gly Arg Asn Phe Asp
                115                 120                 125

Glu Ile Leu Arg Val Val Ile Ser Leu Gln Leu Thr Ala Glu Lys Arg
130                 135                 140

Val Ala Thr Pro Val
145

<210> SEQ ID NO 141
<211> LENGTH: 137
<212> TYPE: PRT
<213> ORGANISM: Homo sapiens

<400> SEQUENCE: 141

Gly Arg Trp Ser Val Phe Phe Phe Tyr Pro Ala Asp Phe Thr Phe Val
 1               5                  10                  15

Cys Pro Thr Glu Leu Gly Asp Val Ala Asp His Tyr Glu Glu Leu Gln
                20                  25                  30

Lys Leu Gly Val Asp Val Tyr Ser Val Ser Thr Asp Thr His Phe Thr
                35                  40                  45

His Lys Ala Trp His Ser Ser Ser Glu Thr Ile Ala Lys Ile Lys Tyr
 50                  55                  60

Ala Met Ile Gly Asp Pro Thr Gly Ala Leu Thr Arg Asn Phe Asp Asn
 65                  70                  75                  80

Met Arg Glu Asp Glu Gly Leu Ala Asp Arg Ala Thr Phe Val Val Asp
                 85                  90                  95

Pro Gln Gly Ile Ile Gln Ala Ile Glu Val Thr Ala Glu Gly Ile Gly
                100                 105                 110

Arg Asp Ala Ser Asp Leu Leu Arg Lys Ile Lys Ala Ala Gln Tyr Val
                115                 120                 125

Ala Ala His Pro Gly Glu Val Cys Pro
                130                 135

<210> SEQ ID NO 142
<211> LENGTH: 139
<212> TYPE: PRT
<213> ORGANISM: Homo sapiens
<220> FEATURE:
<221> NAME/KEY: misc_feature
<222> LOCATION: (17)..(17)
<223> OTHER INFORMATION: Xaa can be any naturally occurring amino acid

<400> SEQUENCE: 142

Gly Lys Tyr Val Val Leu Phe Phe Tyr Pro Leu Asp Phe Thr Phe Val
 1               5                  10                  15

Xaa Pro Thr Glu Ile Ile Ala Phe Ser Asn Arg Ala Glu Asp Phe Arg
                20                  25                  30

Lys Leu Gly Cys Glu Val Leu Gly Val Ser Val Asp Ser Gln Phe Thr
```

```
            35                  40                  45
His Leu Ala Trp Ile Asn Thr Pro Arg Lys Glu Gly Leu Gly Pro
 50                  55                  60
Leu Asn Ile Pro Leu Leu Ala Asp Val Thr Arg Arg Leu Ser Glu Asp
 65                  70                  75                  80
Tyr Gly Val Leu Lys Thr Asp Glu Gly Ile Ala Tyr Arg Gly Leu Phe
                 85                  90                  95
Ile Ile Asp Gly Lys Gly Val Leu Arg Gln Ile Thr Val Asn Asp Leu
            100                 105                 110
Pro Val Gly Arg Ser Val Asp Glu Ala Leu Arg Leu Val Gln Ala Phe
        115                 120                 125
Gln Tyr Thr Asp Glu His Gly Glu Val Cys Pro
130                 135

<210> SEQ ID NO 143
<211> LENGTH: 131
<212> TYPE: PRT
<213> ORGANISM: Homo sapiens

<400> SEQUENCE: 143

Gly Lys Lys Gly Val Leu Phe Gly Val Pro Gly Ala Phe Thr Pro Gly
  1               5                  10                  15
Cys Ser Lys Thr His Leu Pro Gly Phe Val Glu Gln Ala Glu Ala Leu
             20                  25                  30
Lys Ala Lys Gly Val Gln Val Val Ala Cys Leu Ser Val Asn Asp Ala
         35                  40                  45
Phe Val Thr Gly Glu Trp Gly Arg Ala His Lys Ala Glu Gly Lys Val
 50                  55                  60
Arg Leu Leu Ala Asp Pro Thr Gly Ala Phe Gly Lys Glu Thr Asp Leu
 65                  70                  75                  80
Leu Leu Asp Asp Ser Leu Val Ser Ile Phe Gly Asn Arg Arg Leu Lys
                 85                  90                  95
Arg Phe Ser Met Val Val Gln Asp Gly Ile Val Lys Ala Leu Asn Val
            100                 105                 110
Glu Pro Asp Gly Thr Gly Leu Thr Cys Ser Leu Ala Pro Asn Ile Ile
        115                 120                 125
Ser Gln Leu
130

<210> SEQ ID NO 144
<211> LENGTH: 133
<212> TYPE: PRT
<213> ORGANISM: Homo sapiens
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (107)..(107)
```

```
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid

<400> SEQUENCE: 144

Asn Lys Thr Val Ile Val Phe Ser Leu Pro Gly Ala Phe Thr Pro Thr
 1               5                  10                  15

Cys Ser Ser Ser His Leu Pro Arg Tyr Asn Glu Leu Ala Pro Val Phe
            20                  25                  30

Lys Lys Tyr Gly Val Asp Asp Ile Leu Val Val Ser Val Asn Asp Thr
        35                  40                  45

Phe Val Xaa Asn Ala Trp Lys Glu Asp Glu Lys Ser Glu Asn Ile Ser
 50                  55                  60

Phe Ile Pro Asp Gly Asn Gly Glu Phe Thr Gly Xaa Gly Xaa Leu
 65                  70                  75                  80

Val Gly Lys Glu Asp Leu Gly Phe Gly Lys Arg Ser Trp Arg Tyr Ser
                85                  90                  95

Xaa Leu Val Lys Asn Gly Val Val Glu Lys Xaa Phe Ile Glu Pro Asn
            100                 105                 110

Glu Pro Gly Asp Pro Phe Lys Val Ser Asp Ala Asp Thr Xaa Leu Lys
            115                 120                 125

Tyr Leu Ala Pro Gln
            130

<210> SEQ ID NO 145
<211> LENGTH: 117
<212> TYPE: PRT
<213> ORGANISM: Homo sapiens

<400> SEQUENCE: 145

Gly Lys Thr Val Phe Phe Tyr Phe Ser Ala Ser Trp Cys Pro Pro Ser
 1               5                  10                  15

Arg Ala Phe Thr Pro Gln Leu Ile Asp Phe Tyr Lys Ala His Ala Glu
            20                  25                  30

Lys Lys Asn Phe Glu Val Met Leu Ile Ser Trp Asp Glu Ser Ala Glu
        35                  40                  45

Asp Phe Lys Asp Tyr Tyr Ala Lys Met Pro Trp Leu Ala Leu Pro Phe
 50                  55                  60

Glu Asp Arg Lys Gly Met Glu Phe Leu Thr Thr Gly Phe Asp Val Lys
 65                  70                  75                  80

Ser Ile Pro Thr Leu Val Gly Val Glu Ala Asp Ser Gly Asn Ile Ile
                85                  90                  95

Thr Thr Gln Ala Arg Thr Met Val Val Lys Asp Pro Gly Ala Lys Asp
            100                 105                 110

Phe Pro Trp Pro Asn
            115

<210> SEQ ID NO 146
<211> LENGTH: 131
<212> TYPE: PRT
<213> ORGANISM: Homo sapiens

<400> SEQUENCE: 146

Glu Lys His Val Ile Thr Val Phe Thr Asp Ile Thr Cys Gly Tyr Cys
 1               5                  10                  15

His Lys Leu His Glu Gln Met Ala Asp Tyr Asn Ala Leu Gly Ile Thr
```

```
                    20                  25                  30

Val Arg Tyr Leu Ala Phe Pro Arg Gln Gly Leu Asp Ser Asp Ala Glu
            35                  40                  45

Lys Glu Met Lys Ala Ile Trp Cys Ala Lys Asp Lys Asn Lys Ala Phe
 50                  55                  60

Asp Asp Val Met Ala Gly Lys Ser Val Ala Pro Ala Ser Cys Asp Val
 65                  70                  75                  80

Asp Ile Ala Asp His Tyr Ala Leu Gly Val Gln Leu Gly Val Ser Gly
                    85                  90                  95

Thr Pro Ala Val Val Leu Ser Asn Gly Thr Leu Val Pro Gly Tyr Gln
                100                 105                 110

Pro Pro Lys Glu Met Lys Glu Phe Leu Asp Glu His Gln Lys Met Thr
                115                 120                 125

Ser Gly Lys
        130

<210> SEQ ID NO 147
<211> LENGTH: 86
<212> TYPE: PRT
<213> ORGANISM: Homo sapiens

<400> SEQUENCE: 147

Pro Gln Val Glu Leu Phe Val Lys Ala Gly Ser Asp Gly Ala Lys Ile
 1               5                  10                  15

Gly Asn Cys Pro Phe Ser Gln Arg Leu Phe Met Val Leu Trp Leu Lys
                20                  25                  30

Gly Val Thr Phe Asn Val Thr Thr Val Asp Thr Lys Arg Arg Thr Glu
                35                  40                  45

Thr Val Gln Lys Leu Cys Pro Gly Gly Glu Leu Pro Phe Leu Leu Tyr
 50                  55                  60

Gly Thr Glu Val His Thr Asp Thr Asn Lys Ile Glu Glu Phe Leu Glu
 65                  70                  75                  80

Ala Val Leu Cys Pro Pro
                85

<210> SEQ ID NO 148
<211> LENGTH: 83
<212> TYPE: PRT
<213> ORGANISM: Homo sapiens

<400> SEQUENCE: 148

Gly Asp Asp Leu Lys Leu Leu Gly Ala Trp Pro Ser Pro Phe Val Thr
 1               5                  10                  15

Arg Val Lys Leu Ala Leu Ala Leu Lys Gly Leu Ser Tyr Glu Asp Val
                20                  25                  30

Glu Glu Asp Leu Tyr Lys Lys Ser Glu Leu Leu Leu Lys Ser Asn Pro
                35                  40                  45

Val His Lys Lys Ile Pro Val Leu Ile His Asn Gly Ala Pro Val Cys
        50                  55                  60

Glu Ser Met Ile Ile Leu Gln Tyr Ile Asp Glu Val Phe Ala Ser Thr
 65                  70                  75                  80

Gly Pro Ser

<210> SEQ ID NO 149
<211> LENGTH: 79
<212> TYPE: PRT
<213> ORGANISM: Homo sapiens
```

<400> SEQUENCE: 149

Met Gly Leu Glu Leu Phe Leu Asp Leu Val Ser Gln Pro Ser Arg Ala
1               5                   10                  15

Val Tyr Ile Phe Ala Lys Lys Asn Gly Ile Pro Leu Glu Leu Arg Thr
            20                  25                  30

Val Asp Leu Val Lys Gly Gln His Lys Ser Lys Glu Phe Leu Gln Ile
        35                  40                  45

Asn Ser Leu Gly Lys Leu Pro Thr Leu Lys Asp Gly Asp Phe Ile Leu
    50                  55                  60

Thr Glu Ser Ser Ala Ile Leu Ile Tyr Leu Ser Cys Lys Tyr Gln
65                  70                  75

<210> SEQ ID NO 150
<211> LENGTH: 78
<212> TYPE: PRT
<213> ORGANISM: Homo sapiens

<400> SEQUENCE: 150

Ser Gly Lys Pro Val Leu His Tyr Phe Asn Ala Arg Gly Arg Met Glu
1               5                   10                  15

Cys Ile Arg Phe Leu Leu Ala Ala Ala Gly Val Glu Phe Asp Glu Lys
            20                  25                  30

Phe Ile Gln Ser Pro Glu Asp Leu Glu Lys Leu Lys Lys Asp Gly Asn
        35                  40                  45

Leu Met Phe Asp Gln Val Pro Met Val Glu Ile Asp Gly Met Lys Leu
    50                  55                  60

Ala Gln Thr Arg Ala Ile Leu Asn Tyr Ile Ala Thr Lys Tyr
65                  70                  75

<210> SEQ ID NO 151
<211> LENGTH: 78
<212> TYPE: PRT
<213> ORGANISM: Homo sapiens

<400> SEQUENCE: 151

Met Asp Phe Tyr Tyr Leu Pro Gly Ser Ala Pro Cys Arg Ala Val Gln
1               5                   10                  15

Met Thr Ala Ala Ala Val Gly Val Glu Leu Asn Leu Lys Leu Thr Asn
            20                  25                  30

Leu Met Ala Gly Glu His Met Lys Pro Glu Phe Leu Lys Ile Asn Pro
        35                  40                  45

Gln His Cys Ile Pro Thr Leu Val Asp Asn Gly Phe Ala Leu Trp Glu
    50                  55                  60

Ser Arg Ala Ile Cys Thr Tyr Leu Ala Glu Lys Tyr Gly Lys
65                  70                  75

<210> SEQ ID NO 152
<211> LENGTH: 83
<212> TYPE: PRT
<213> ORGANISM: Homo sapiens

<400> SEQUENCE: 152

Pro Glu Gly Ser Ile Arg Ile Tyr Ser Met Arg Phe Cys Pro Phe Ala
1               5                   10                  15

Glu Arg Thr Arg Leu Val Leu Lys Ala Lys Gly Ile Arg His Glu Val
            20                  25                  30

Ile Asn Ile Asn Leu Lys Asn Lys Pro Glu Trp Phe Phe Lys Lys Asn

```
                35                  40                  45
Pro Phe Gly Leu Val Pro Val Leu Glu Asn Ser Gln Gly Gln Leu Ile
 50                  55                  60
Tyr Glu Ser Ala Ile Thr Cys Glu Tyr Leu Asp Glu Ala Tyr Pro Gly
 65                  70                  75                  80
Lys Lys Leu

<210> SEQ ID NO 153
<211> LENGTH: 75
<212> TYPE: PRT
<213> ORGANISM: Homo sapiens
<220> FEATURE:
<221> NAME/KEY: misc_feature
<222> LOCATION: (64)..(64)
<223> OTHER INFORMATION: Xaa can be any naturally occurring amino acid

<400> SEQUENCE: 153

Met Ser Gln Gly Thr Leu Tyr Ala Asn Phe Arg Ile Arg Thr Trp Val
 1               5                  10                  15
Pro Arg Gly Leu Val Lys Ala Leu Lys Leu Asp Val Lys Val Val Thr
                20                  25                  30
Pro Asp Ala Ala Glu Gln Phe Ala Arg Asp Phe Pro Leu Lys Lys
                35                  40                  45
Val Pro Ala Phe Val Gly Pro Lys Gly Tyr Lys Leu Thr Glu Ala Xaa
 50                  55                  60
Ala Ile Asn Tyr Tyr Leu Val Lys Leu Ser Gln
 65                  70                  75

<210> SEQ ID NO 154
<211> LENGTH: 75
<212> TYPE: PRT
<213> ORGANISM: Homo sapiens

<400> SEQUENCE: 154

Pro Lys Tyr Thr Leu His Tyr Phe Pro Leu Met Gly Arg Ala Glu Leu
 1               5                  10                  15
Cys Arg Phe Val Leu Ala Ala His Gly Glu Glu Phe Thr Asp Arg Val
                20                  25                  30
Val Glu Met Ala Asp Trp Pro Asn Leu Lys Ala Thr Met Tyr Ser Asn
                35                  40                  45
Ala Met Pro Val Leu Asp Ile Asp Gly Thr Lys Met Ser Gln Ser Met
 50                  55                  60
Cys Ile Ala Arg His Leu Ala Arg Glu Phe Gly
 65                  70                  75

<210> SEQ ID NO 155
<211> LENGTH: 75
<212> TYPE: PRT
<213> ORGANISM: Homo sapiens

<400> SEQUENCE: 155

Met Pro Asn Tyr Lys Leu Leu Tyr Phe Asn Met Arg Gly Arg Ala Glu
 1               5                  10                  15
Ile Ile Arg Tyr Ile Phe Ala Tyr Leu Asp Ile Lys Tyr Glu Asp His
                20                  25                  30
Arg Ile Glu Gln Ala Asp Trp Pro Lys Ile Lys Pro Thr Leu Pro Phe
                35                  40                  45
Gly Lys Ile Pro Val Leu Glu Val Glu Gly Leu Thr Leu His Gln Ser
 50                  55                  60
```

```
Leu Ala Ile Ala Arg Tyr Leu Thr Lys Asn Thr
 65                  70                  75

<210> SEQ ID NO 156
<211> LENGTH: 84
<212> TYPE: PRT
<213> ORGANISM: Homo sapiens

<400> SEQUENCE: 156

Pro Met Ile Leu Gly Tyr Trp Asn Val Arg Gly Leu Thr His Pro Ile
 1               5                  10                  15

Arg Leu Leu Leu Glu Tyr Thr Asp Ser Ser Tyr Glu Glu Lys Arg Tyr
             20                  25                  30

Ala Met Gly Asp Ala Pro Asp Tyr Asp Arg Ser Gln Trp Leu Asn Glu
         35                  40                  45

Lys Phe Lys Leu Gly Leu Asp Phe Pro Asn Leu Pro Tyr Leu Ile Asp
     50                  55                  60

Gly Ser Arg Lys Ile Thr Gln Ser Asn Ala Ile Met Arg Tyr Leu Ala
 65                  70                  75                  80

Arg Lys His His

<210> SEQ ID NO 157
<211> LENGTH: 76
<212> TYPE: PRT
<213> ORGANISM: Homo sapiens

<400> SEQUENCE: 157

Pro Pro Tyr Thr Val Val Tyr Phe Pro Val Arg Gly Arg Cys Ala Ala
 1               5                  10                  15

Leu Arg Met Leu Leu Ala Asp Gln Gly Gln Ser Trp Lys Glu Glu Val
             20                  25                  30

Val Thr Val Glu Thr Trp Gln Glu Gly Ser Leu Lys Ala Ser Cys Leu
         35                  40                  45

Tyr Gly Gln Leu Pro Lys Phe Gln Asp Gly Asp Leu Thr Leu Tyr Gln
     50                  55                  60

Ser Asn Thr Ile Leu Arg His Leu Gly Arg Thr Leu
 65                  70                  75

<210> SEQ ID NO 158
<211> LENGTH: 80
<212> TYPE: PRT
<213> ORGANISM: Homo sapiens

<400> SEQUENCE: 158

Met Lys Leu Phe Ile Ser Pro Gly Ala Cys Ser Leu Ala Pro His Ile
 1               5                  10                  15

Ala Leu Arg Glu Thr Gly Ala Asp Phe Glu Ala Val Lys Val Asp Leu
             20                  25                  30

Ala Val Arg Lys Thr Glu Ala Gly Glu Asp Phe Leu Thr Val Asn Pro
         35                  40                  45

Ser Gly Lys Val Pro Ala Leu Thr Leu Asp Ser Gly Glu Thr Leu Thr
     50                  55                  60

Glu Asn Pro Ala Ile Leu Leu Tyr Ile Ala Asp Gln Asn Pro Ala Ser
 65                  70                  75                  80

<210> SEQ ID NO 159
<211> LENGTH: 91
<212> TYPE: PRT
```

<213> ORGANISM: Homo sapiens

<400> SEQUENCE: 159

Pro Leu Glu Gly Tyr Thr Leu Phe Ser His Arg Ser Ala Pro Asn Gly
1               5                   10                  15

Phe Lys Val Ala Ile Val Leu Ser Glu Leu Gly Phe His Tyr Asn Thr
            20                  25                  30

Ile Phe Leu Asp Phe Asn Leu Gly Glu His Arg Ala Pro Glu Phe Val
        35                  40                  45

Ser Val Asn Pro Asn Ala Arg Val Pro Ala Leu Ile Asp His Gly Met
    50                  55                  60

Asp Asn Leu Ser Ile Trp Glu Ser Gly Ala Ile Leu Leu His Leu Val
65                  70                  75                  80

Asn Lys Tyr Tyr Lys Glu Thr Gly Asn Pro Leu
                85                  90

<210> SEQ ID NO 160
<211> LENGTH: 83
<212> TYPE: PRT
<213> ORGANISM: Homo sapiens

<400> SEQUENCE: 160

Lys Pro Ile Leu Tyr Ser Tyr Phe Arg Ser Cys Ser Trp Arg Val
1               5                   10                  15

Arg Ile Ala Leu Ala Leu Lys Gly Ile Asp Tyr Lys Thr Val Pro Ile
            20                  25                  30

Asn Leu Ile Lys Asp Gly Gly Gln Gln Phe Ser Lys Asp Phe Gln Ala
        35                  40                  45

Leu Asn Pro Met Lys Gln Val Pro Thr Leu Lys Ile Asp Gly Ile Thr
    50                  55                  60

Ile His Gln Ser Leu Ala Ile Glu Tyr Leu Glu Glu Thr Arg Pro
65                  70                  75                  80

Thr Pro Arg

<210> SEQ ID NO 161
<211> LENGTH: 75
<212> TYPE: PRT
<213> ORGANISM: Homo sapiens

<400> SEQUENCE: 161

Met Lys Leu Tyr Ile Tyr Asp His Cys Pro Tyr Cys Leu Lys Ala Arg
1               5                   10                  15

Met Ile Phe Gly Leu Lys Asn Ile Pro Val Glu Leu His Val Leu Leu
            20                  25                  30

Asn Asp Asp Ala Glu Thr Pro Thr Arg Met Val Gly Gln Lys Gln Val
        35                  40                  45

Pro Ile Leu Gln Lys Asp Asp Ser Arg Tyr Met Pro Glu Ser Met Asp
    50                  55                  60

Ile Val His Tyr Val Asp Lys Leu Asp Gly Lys
65                  70                  75

<210> SEQ ID NO 162
<211> LENGTH: 73
<212> TYPE: PRT
<213> ORGANISM: Homo sapiens

<400> SEQUENCE: 162

Gln Val Gln Glu Ser Ile Ser Ile Phe Thr Lys Pro Gly Cys Pro Phe

```
                1               5                   10                  15
Cys Ala Lys Ala Lys Gln Leu Leu His Asp Lys Gly Leu Ser Phe Glu
                    20                  25                  30

Glu Ile Ile Leu Gly His Asp Ala Thr Ile Val Ser Val Arg Ala Val
            35                  40                  45

Ser Gly Arg Thr Thr Val Pro Gln Val Phe Ile Gly Lys His Ile
        50                  55                  60

Gly Gly Ser Asp Asp Leu Glu Lys Tyr
65                  70
```

<210> SEQ ID NO 163
<211> LENGTH: 80
<212> TYPE: PRT
<213> ORGANISM: Homo sapiens

<400> SEQUENCE: 163

```
Ala Pro Met Lys Leu Tyr Gly Ala Val Met Ser Trp Asn Leu Thr Arg
1               5                   10                  15

Cys Ala Thr Ala Leu Glu Glu Ala Gly Ser Asp Tyr Glu Ile Val Pro
                    20                  25                  30

Ile Asn Phe Ala Thr Ala Glu His Lys Ser Pro Glu His Leu Val Arg
            35                  40                  45

Asn Pro Phe Gly Gln Val Pro Ala Leu Gln Asp Gly Asp Leu Tyr Leu
        50                  55                  60

Phe Glu Ser Arg Ala Ile Cys Lys Tyr Ala Ala Arg Lys Asn Lys Pro
65                  70                  75                  80
```

<210> SEQ ID NO 164
<211> LENGTH: 87
<212> TYPE: PRT
<213> ORGANISM: Homo sapiens

<400> SEQUENCE: 164

```
Met Phe Lys Val Tyr Gly Tyr Asp Ser Asn Ile His Lys Cys Val Tyr
1               5                   10                  15

Cys Asp Asn Ala Lys Arg Leu Leu Thr Val Lys Lys Gln Pro Phe Glu
                    20                  25                  30

Phe Ile Asn Ile Met Pro Glu Lys Gly Val Phe Asp Asp Glu Lys Ile
            35                  40                  45

Ala Glu Leu Leu Thr Lys Leu Gly Arg Asp Thr Gln Ile Gly Leu Thr
        50                  55                  60

Met Pro Gln Val Phe Ala Pro Asp Gly Ser His Ile Gly Gly Phe Asp
65                  70                  75                  80

Gln Leu Arg Glu Tyr Phe Lys
                85
```

<210> SEQ ID NO 165
<211> LENGTH: 85
<212> TYPE: PRT
<213> ORGANISM: Homo sapiens

<400> SEQUENCE: 165

```
Met Gln Thr Val Ile Phe Gly Arg Ser Gly Cys Pro Tyr Ser Val Arg
1               5                   10                  15

Ala Lys Asp Leu Ala Glu Lys Leu Ser Asn Glu Arg Asp Asp Phe Gln
                    20                  25                  30

Tyr Gln Tyr Val Asp Ile Arg Ala Glu Gly Ile Thr Lys Glu Asp Leu
            35                  40                  45
```

Gln Gln Lys Ala Gly Lys Pro Val Glu Thr Val Pro Gln Ile Phe Val
            50                  55                  60

Asp Gln Gln His Ile Gly Gly Tyr Thr Asp Phe Ala Ala Trp Val Lys
65                  70                  75                  80

Glu Asn Leu Asp Ala
            85

<210> SEQ ID NO 166
<211> LENGTH: 95
<212> TYPE: PRT
<213> ORGANISM: Homo sapiens

<400> SEQUENCE: 166

Pro Gly Lys Val Val Phe Ile Lys Pro Thr Cys Pro Phe Cys Arg
1               5                   10                  15

Lys Thr Gln Glu Leu Leu Ser Gln Leu Pro Phe Lys Glu Gly Leu Leu
            20                  25                  30

Glu Phe Val Asp Ile Thr Ala Thr Ser Asp Thr Asn Glu Ile Gln Asp
        35                  40                  45

Tyr Leu Gln Gln Leu Thr Gly Ala Arg Thr Val Pro Arg Val Phe Ile
    50                  55                  60

Gly Lys Glu Cys Ile Gly Gly Cys Thr Asp Leu Glu Ser Met His Lys
65                  70                  75                  80

Arg Gly Glu Leu Leu Thr Arg Leu Gln Gln Val Gly Ala Val Lys
                85                  90                  95

<210> SEQ ID NO 167
<211> LENGTH: 82
<212> TYPE: PRT
<213> ORGANISM: Homo sapiens

<400> SEQUENCE: 167

Ala Asn Val Glu Ile Tyr Thr Lys Glu Thr Cys Pro Tyr Cys His Arg
1               5                   10                  15

Ala Lys Ala Leu Leu Ser Ser Lys Gly Val Ser Phe Gln Glu Leu Pro
            20                  25                  30

Ile Asp Gly Asn Ala Ala Lys Arg Glu Glu Met Ile Lys Arg Ser Gly
        35                  40                  45

Arg Thr Thr Val Pro Gln Ile Phe Ile Asp Ala Gln His Ile Gly Gly
    50                  55                  60

Tyr Asp Asp Leu Tyr Ala Leu Asp Ala Arg Gly Gly Leu Asp Pro Leu
65                  70                  75                  80

Leu Lys

<210> SEQ ID NO 168
<211> LENGTH: 76
<212> TYPE: PRT
<213> ORGANISM: Homo sapiens

<400> SEQUENCE: 168

Met Arg Ile Thr Ile Tyr Thr Arg Asn Asp Cys Val Gln Cys His Ala
1               5                   10                  15

Thr Lys Arg Ala Met Glu Asn Arg Gly Phe Asp Phe Glu Met Ile Asn
            20                  25                  30

Val Asp Arg Val Pro Glu Ala Ala Glu Ala Leu Arg Ala Gln Gly Phe
        35                  40                  45

Arg Gln Leu Pro Val Val Ile Ala Gly Asp Leu Ser Trp Ser Gly Phe

```
                    50                  55                  60
Arg Pro Asp Met Ile Asn Arg Leu His Pro Ala Pro
65                  70                  75

<210> SEQ ID NO 169
<211> LENGTH: 86
<212> TYPE: PRT
<213> ORGANISM: Homo sapiens

<400> SEQUENCE: 169

Asp Lys Leu Val Val Asp Phe Ser Ala Thr Trp Cys Gly Pro Cys
1               5                   10                  15

Lys Met Ile Lys Pro Phe Phe His Ser Leu Ser Glu Lys Tyr Ser Asn
                20                  25                  30

Val Ile Phe Leu Glu Val Asp Val Asp Cys Gln Asp Val Ala Ser
            35                  40                  45

Glu Cys Glu Val Lys Cys Met Pro Thr Phe Gln Phe Phe Lys Gly
        50                  55                  60

Gln Lys Val Gly Glu Phe Ser Gly Ala Asn Lys Glu Lys Leu Glu Ala
65                  70                  75                  80

Thr Ile Asn Glu Leu Val
                85

<210> SEQ ID NO 170
<211> LENGTH: 88
<212> TYPE: PRT
<213> ORGANISM: Homo sapiens

<400> SEQUENCE: 170

Asp Lys Pro Val Val Leu Asp Met Phe Thr Gln Trp Cys Gly Pro Cys
1               5                   10                  15

Lys Ala Met Ala Pro Lys Tyr Glu Lys Leu Ala Glu Glu Tyr Leu Asp
                20                  25                  30

Val Ile Phe Leu Lys Leu Asp Cys Asn Gln Glu Asn Lys Thr Leu Ala
            35                  40                  45

Lys Glu Leu Gly Ile Arg Val Val Pro Thr Phe Lys Ile Leu Lys Glu
        50                  55                  60

Asn Ser Val Val Gly Glu Val Thr Gly Ala Lys Tyr Asp Lys Leu Leu
65                  70                  75                  80

Glu Ala Ile Gln Ala Ala Arg Ser
                85

<210> SEQ ID NO 171
<211> LENGTH: 87
<212> TYPE: PRT
<213> ORGANISM: Homo sapiens

<400> SEQUENCE: 171

Ser Arg Leu Ala Val Val Lys Phe Thr Met Arg Gly Cys Gly Pro Cys
1               5                   10                  15

Leu Arg Ile Ala Pro Ala Phe Ser Ser Met Ser Asn Lys Tyr Pro Gln
                20                  25                  30

Ala Val Phe Leu Glu Val Asp Val His Gln Cys Gln Gly Thr Ala Ala
            35                  40                  45

Thr Asn Asn Ile Ser Ala Thr Pro Thr Phe Gln Phe Phe Arg Asn Lys
        50                  55                  60

Val Arg Ile Asp Gln Tyr Gln Gly Ala Asp Ala Val Gly Leu Glu Glu
65                  70                  75                  80
```

```
Lys Ile Lys Gln His Leu Glu
                85

<210> SEQ ID NO 172
<211> LENGTH: 89
<212> TYPE: PRT
<213> ORGANISM: Homo sapiens

<400> SEQUENCE: 172

His Lys Pro Ile Val Val Asp Phe Thr Ala Thr Trp Cys Gly Pro Cys
1               5                   10                  15

Lys Met Ile Ala Pro Leu Phe Glu Thr Leu Ser Asn Asp Tyr Ala Gly
            20                  25                  30

Lys Val Ile Phe Leu Lys Val Asp Val Asp Ala Val Ala Ala Val Ala
        35                  40                  45

Glu Ala Ala Gly Ile Thr Ala Met Pro Thr Phe His Val Tyr Lys Asp
    50                  55                  60

Gly Val Lys Ala Asp Asp Leu Val Gly Ala Ser Gln Asp Lys Leu Lys
65                  70                  75                  80

Ala Leu Val Ala Lys His Ala Ala Ala
                85

<210> SEQ ID NO 173
<211> LENGTH: 88
<212> TYPE: PRT
<213> ORGANISM: Homo sapiens

<400> SEQUENCE: 173

Asp Gly Ala Ile Leu Val Asp Phe Trp Ala Glu Trp Cys Gly Pro Cys
1               5                   10                  15

Lys Met Ile Ala Pro Ile Leu Asp Glu Ile Ala Asp Glu Tyr Gln Gly
            20                  25                  30

Lys Leu Thr Val Ala Lys Leu Asn Ile Asp Gln Asn Pro Gly Thr Ala
        35                  40                  45

Pro Lys Tyr Gly Ile Arg Gly Ile Pro Thr Leu Leu Leu Phe Lys Asn
    50                  55                  60

Gly Glu Val Ala Ala Thr Lys Val Gly Ala Leu Ser Lys Gly Gln Leu
65                  70                  75                  80

Lys Glu Phe Leu Asp Ala Asn Leu
                85

<210> SEQ ID NO 174
<211> LENGTH: 89
<212> TYPE: PRT
<213> ORGANISM: Homo sapiens

<400> SEQUENCE: 174

Glu Gln Pro Val Leu Val Tyr Phe Trp Ala Ser Trp Cys Gly Pro Cys
1               5                   10                  15

Gln Leu Met Ser Pro Leu Ile Asn Leu Ala Ala Asn Thr Tyr Ser Asp
            20                  25                  30

Arg Leu Lys Val Val Lys Leu Glu Ile Asp Pro Asn Pro Thr Thr Val
        35                  40                  45

Lys Lys Tyr Lys Val Glu Gly Val Pro Ala Leu Arg Leu Val Lys Gly
    50                  55                  60

Glu Gln Ile Leu Asp Ser Thr Glu Gly Val Ile Ser Lys Asp Lys Leu
65                  70                  75                  80
```

Leu Ser Phe Leu Asp Thr His Leu Asn
                85

<210> SEQ ID NO 175
<211> LENGTH: 77
<212> TYPE: PRT
<213> ORGANISM: Homo sapiens

<400> SEQUENCE: 175

Met Met Lys Ile Gln Ile Tyr Gly Thr Gly Cys Ala Asn Cys Gln Met
1               5                   10                  15

Leu Glu Lys Asn Ala Arg Glu Ala Val Lys Glu Leu Gly Ile Asp Ala
                20                  25                  30

Glu Phe Glu Lys Ile Lys Glu Met Asp Gln Ile Leu Glu Ala Gly Leu
            35                  40                  45

Thr Ala Leu Pro Gly Leu Ala Val Asp Gly Glu Leu Lys Ile Met Gly
    50                  55                  60

Arg Val Ala Ser Lys Glu Glu Ile Lys Lys Ile Leu Ser
65                  70                  75

<210> SEQ ID NO 176
<211> LENGTH: 85
<212> TYPE: PRT
<213> ORGANISM: Homo sapiens

<400> SEQUENCE: 176

Met Ser Lys Val Lys Ile Glu Leu Phe Thr Ser Pro Met Cys Pro His
1               5                   10                  15

Cys Pro Ala Ala Lys Arg Val Val Glu Val Ala Asn Glu Met Pro
                20                  25                  30

Asp Ala Val Glu Val Glu Tyr Ile Asn Val Met Glu Asn Pro Gln Lys
            35                  40                  45

Ala Met Glu Tyr Gly Ile Met Ala Val Pro Thr Ile Val Ile Asn Gly
    50                  55                  60

Asp Val Glu Phe Ile Gly Ala Pro Thr Lys Glu Ala Leu Val Glu Ala
65                  70                  75                  80

Ile Lys Lys Arg Leu
                85

<210> SEQ ID NO 177
<211> LENGTH: 117
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 177

Asn Ile Thr Ile Tyr His Asn Pro Ala Xaa Gly Thr Ser Arg Asn Thr
1               5                   10                  15

Leu Glu Met Ile Arg Asn Ser Gly Thr Glu Pro Thr Ile Ile Leu Tyr
                20                  25                  30

Leu Glu Asn Pro Pro Ser Arg Asp Glu Leu Val Lys Leu Ile Ala Asp
            35                  40                  45

Met Gly Ile Ser Val Arg Ala Leu Leu Arg Lys Asn Val Glu Pro Tyr
    50                  55                  60

Glu Gln Leu Gly Leu Ala Glu Asp Lys Phe Thr Asp Asp Gln Leu Ile
65                  70                  75                  80

```
Asp Phe Met Leu Gln His Pro Ile Leu Ile Asn Arg Pro Ile Val Val
                 85                  90                  95

Thr Pro Leu Gly Thr Arg Leu Cys Arg Pro Ser Glu Val Val Leu Asp
            100                 105                 110

Ile Leu Gln Asp Ala
        115

<210> SEQ ID NO 178
<211> LENGTH: 163
<212> TYPE: PRT
<213> ORGANISM: Homo sapiens

<400> SEQUENCE: 178

Ser Pro Val Val Ser Glu Phe Phe Ser Phe Tyr Cys Pro His Cys Asn
1               5                   10                  15

Thr Phe Glu Pro Ile Ile Ala Gln Leu Lys Gln Leu Pro Glu Gly
            20                  25                  30

Ala Lys Phe Gln Lys Asn His Val Ser Phe Met Gly Gly Asn Met Gly
        35                  40                  45

Gln Ala Met Ser Lys Ala Tyr Ala Thr Met Ile Ala Leu Glu Val Glu
    50                  55                  60

Asp Lys Met Val Pro Val Met Phe Asn Arg Ile His Thr Leu Arg Lys
65                  70                  75                  80

Pro Pro Lys Asp Glu Gln Glu Leu Arg Gln Ile Phe Leu Asp Glu Gly
                85                  90                  95

Ile Asp Ala Ala Lys Phe Asp Ala Ala Tyr Asn Gly Phe Ala Val Asp
            100                 105                 110

Ser Met Val Arg Arg Phe Asp Lys Gln Phe Gln Asp Ser Gly Leu Thr
        115                 120                 125

Gly Val Pro Ala Val Val Asn Asn Arg Tyr Leu Val Gln Gly Gln
    130                 135                 140

Ser Val Lys Ser Leu Asp Glu Tyr Phe Asp Leu Val Asn Tyr Leu Leu
145                 150                 155                 160

Thr Leu Lys

<210> SEQ ID NO 179
<211> LENGTH: 125
<212> TYPE: PRT
<213> ORGANISM: Homo sapiens

<400> SEQUENCE: 179

Leu Val Ala Gln Gln Glu Lys Ala Ala Asp Val Gln Leu Arg Gly
1               5                   10                  15

Val Pro Ala Met Phe Val Asn Gly Lys Tyr Gln Leu Asn Pro Gln Gly
            20                  25                  30

Met Asp Thr Ser Asn Met Asp Val Phe Val Gln Gln Tyr Ala Asp Thr
        35                  40                  45

Val Lys Tyr Leu Ser Glu Lys Lys Gly Gly Thr Gly Ala Gln Tyr
    50                  55                  60

Glu Asp Gly Lys Gln Tyr Thr Thr Leu Glu Lys Pro Val Ala Gly Ala
65                  70                  75                  80

Pro Gln Val Leu Glu Phe Phe Ser Phe Pro Cys Pro His Cys Tyr Gln
                85                  90                  95

Phe Glu Glu Val Leu His Ile Ser Asp Asn Val Lys Lys Lys Leu Pro
            100                 105                 110

Glu Gly Val Lys Met Thr Lys Tyr His Val Asn Phe Met
        115                 120                 125
```

115                 120                 125

<210> SEQ ID NO 180
<211> LENGTH: 98
<212> TYPE: PRT
<213> ORGANISM: Homo sapiens

<400> SEQUENCE: 180

Ile Thr Thr Ile Val Val His Ile Tyr Glu Asp Gly Ile Lys Gly Cys
1               5                   10                  15

Asp Ala Leu Asn Ser Ser Leu Ile Cys Leu Ala Ala Glu Tyr Pro Met
                20                  25                  30

Val Lys Phe Cys Lys Ile Lys Ala Ser Asn Thr Gly Ala Gly Asp Arg
            35                  40                  45

Phe Ser Ser Asp Val Leu Pro Thr Leu Leu Val Tyr Lys Gly Gly Glu
    50                  55                  60

Leu Leu Ser Asn Phe Ile Ser Val Thr Glu Gln Leu Ala Glu Glu Phe
65                  70                  75                  80

Phe Thr Gly Asp Val Glu Ser Phe Leu Asn Glu Tyr Gly Leu Leu Pro
                85                  90                  95

Glu Lys

<210> SEQ ID NO 181
<211> LENGTH: 84
<212> TYPE: PRT
<213> ORGANISM: Homo sapiens

<400> SEQUENCE: 181

Lys Pro Val Glu Leu Ile Ala Thr Leu Asp Asp Ser Ala Lys Ser Ala
1               5                   10                  15

Glu Ile Lys Glu Leu Leu Ala Glu Ile Ala Glu Leu Ser Asp Lys Val
                20                  25                  30

Thr Phe Lys Glu Asp Asn Thr Leu Pro Val Arg Lys Pro Ser Phe Leu
            35                  40                  45

Ile Thr Asn Pro Gly Ser Gln Gln Gly Pro Arg Phe Ala Gly Ser Pro
    50                  55                  60

Leu Gly His Glu Phe Thr Ser Leu Val Leu Ala Leu Leu Trp Thr Gly
65                  70                  75                  80

Gly His Pro Ser

<210> SEQ ID NO 182
<211> LENGTH: 98
<212> TYPE: PRT
<213> ORGANISM: Homo sapiens

<400> SEQUENCE: 182

Asn Pro Val Lys Leu Ile Val Phe Val Arg Lys Asp His Cys Gln Tyr
1               5                   10                  15

Cys Asp Gln Leu Lys Gln Leu Val Gln Glu Leu Ser Glu Leu Thr Asp
                20                  25                  30

Lys Leu Ser Tyr Glu Ile Val Asp Phe Asp Thr Pro Glu Gly Lys Glu
            35                  40                  45

Leu Ala Lys Arg Tyr Arg Ile Asp Arg Ala Pro Ala Thr Thr Ile Thr
    50                  55                  60

Gln Asp Gly Lys Asp Phe Gly Val Arg Tyr Phe Gly Leu Pro Ala Gly
65                  70                  75                  80

His Glu Phe Ala Ala Phe Leu Glu Asp Ile Val Asp Val Ser Arg Glu

Glu Thr

<210> SEQ ID NO 183
<211> LENGTH: 82
<212> TYPE: PRT
<213> ORGANISM: Homo sapiens

<400> SEQUENCE: 183

Gly Asp Phe Glu Phe Glu Thr Tyr Tyr Ser Leu Ser Cys His Asn Cys
1               5                   10                  15

Pro Asp Val Val Gln Ala Leu Asn Leu Met Ala Val Leu Asn Pro Arg
            20                  25                  30

Ile Lys His Thr Ala Ile Asp Gly Gly Thr Phe Gln Asn Glu Ile Thr
        35                  40                  45

Glu Arg Asn Val Met Gly Val Pro Ala Val Phe Val Asn Gly Lys Glu
    50                  55                  60

Phe Gly Gln Gly Arg Met Thr Leu Thr Glu Ile Ala Lys Val Asp
65                  70                  75                  80

Thr Gly

<210> SEQ ID NO 184
<211> LENGTH: 93
<212> TYPE: PRT
<213> ORGANISM: Homo sapiens

<400> SEQUENCE: 184

Gln Asp Val Arg Ile Leu Val Phe Val Thr Pro Thr Cys Pro Tyr Cys
1               5                   10                  15

Pro Leu Ala Val Arg Met Ala His Lys Phe Ala Ile Glu Asn Thr Lys
            20                  25                  30

Ala Gly Lys Gly Lys Ile Leu Gly Asp Met Val Glu Ala Ile Glu Tyr
        35                  40                  45

Pro Glu Trp Ala Asp Gln Tyr Asn Val Met Ala Val Pro Lys Ile Val
    50                  55                  60

Ile Gln Val Asn Gly Glu Asp Arg Val Glu Phe Glu Gly Ala Tyr Pro
65                  70                  75                  80

Glu Lys Met Phe Leu Glu Lys Leu Leu Ser Ala Leu Ser
            85                  90

<210> SEQ ID NO 185
<211> LENGTH: 96
<212> TYPE: PRT
<213> ORGANISM: Homo sapiens

<400> SEQUENCE: 185

Lys Tyr Leu Leu Val Glu Phe Tyr Ala Pro Trp Cys Gly His Cys Lys
1               5                   10                  15

Ala Leu Ala Pro Glu Tyr Ala Lys Ala Gly Lys Leu Lys Ala Glu
            20                  25                  30

Gly Ser Glu Ile Arg Leu Ala Lys Val Asp Ala Thr Glu Glu Ser Asp
        35                  40                  45

Leu Ala Gln Gln Tyr Gly Val Arg Gly Tyr Pro Thr Ile Lys Phe Phe
    50                  55                  60

Arg Asn Gly Asp Thr Ala Ser Pro Lys Glu Tyr Thr Ala Gly Arg Glu
65                  70                  75                  80

Ala Asp Asp Ile Val Asn Trp Leu Lys Lys Arg Thr Gly Pro Ala Ala

-continued

```
                    85                  90                  95
```

<210> SEQ ID NO 186
<211> LENGTH: 84
<212> TYPE: PRT
<213> ORGANISM: Homo sapiens

<400> SEQUENCE: 186

```
Ser Glu Val Ala Val Ile Gly Phe Phe Lys Asp Val Glu Ser Asp Ser
1               5                   10                  15

Ala Lys Gln Phe Leu Gln Ala Ala Glu Ala Ile Asp Ile Pro Phe
                20                  25                  30

Gly Ile Thr Ser Asn Ser Asp Val Phe Ser Lys Tyr Gln Leu Asp Lys
                35                  40                  45

Asp Gly Val Val Leu Phe Lys Lys Phe Asp Glu Gly Arg Asn Asn Phe
        50                  55                  60

Glu Gly Glu Val Thr Lys Glu Asn Leu Leu Asp Phe Ile Lys His Asn
65                  70                  75                  80

Gln Leu Pro Leu
```

<210> SEQ ID NO 187
<211> LENGTH: 85
<212> TYPE: PRT
<213> ORGANISM: Homo sapiens

<400> SEQUENCE: 187

```
Asp Glu Ile Lys Leu Ile Gly Tyr Phe Lys Asn Lys Asp Ser Glu His
1               5                   10                  15

Tyr Lys Ala Phe Lys Glu Ala Ala Glu Glu Phe His Pro Tyr Ile Pro
                20                  25                  30

Phe Phe Ala Thr Phe Asp Ser Lys Val Ala Lys Lys Leu Thr Leu Lys
                35                  40                  45

Leu Asn Glu Ile Asp Phe Tyr Glu Ala Phe Met Glu Glu Pro Val Thr
        50                  55                  60

Ile Pro Asp Lys Pro Asn Ser Glu Glu Glu Ile Val Asn Phe Val Glu
65                  70                  75                  80

Glu His Arg Arg Ser
                85
```

<210> SEQ ID NO 188
<211> LENGTH: 97
<212> TYPE: PRT
<213> ORGANISM: Homo sapiens

<400> SEQUENCE: 188

```
Tyr Glu Val Leu Ala Leu Leu Tyr His Glu Pro Pro Glu Asp Asp Lys
1               5                   10                  15

Ala Ser Gln Arg Gln Phe Glu Met Glu Glu Leu Ile Leu Glu Leu Ala
                20                  25                  30

Ala Gln Val Leu Glu Asp Lys Gly Val Gly Phe Gly Leu Val Asp Ser
                35                  40                  45

Glu Lys Asp Ala Ala Val Ala Lys Lys Leu Gly Leu Thr Glu Glu Asp
        50                  55                  60

Ser Ile Tyr Val Phe Lys Glu Asp Glu Val Ile Glu Tyr Asp Gly Glu
65                  70                  75                  80

Phe Ser Ala Asp Thr Leu Val Glu Phe Leu Leu Asp Val Leu Glu Asp
                85                  90                  95
```

Pro

<210> SEQ ID NO 189
<211> LENGTH: 101
<212> TYPE: PRT
<213> ORGANISM: Homo sapiens

<400> SEQUENCE: 189

Asp Gly Ile His Ile Val Ala Phe Ala Glu Ala Asp Pro Asp Gly
1               5                   10                  15

Tyr Glu Phe Leu Glu Ile Leu Lys Ser Val Ala Gln Asp Asn Thr Asp
            20                  25                  30

Asn Pro Asp Leu Ser Ile Ile Trp Ile Asp Pro Asp Phe Pro Leu
        35                  40                  45

Leu Val Pro Tyr Trp Glu Lys Thr Phe Asp Ile Asp Leu Ser Ala Pro
    50                  55                  60

Gln Ile Gly Val Val Asn Val Thr Asp Ala Asp Ser Val Trp Met Glu
65                  70                  75                  80

Met Asp Asp Glu Glu Asp Leu Pro Ser Ala Glu Leu Glu Asp Trp
                85                  90                  95

Leu Glu Asp Val Leu
            100

<210> SEQ ID NO 190
<211> LENGTH: 101
<212> TYPE: PRT
<213> ORGANISM: Homo sapiens

<400> SEQUENCE: 190

Lys Phe Val Leu Val Lys Phe Asp Thr Gln Tyr Pro Tyr Gly Glu Lys
1               5                   10                  15

Gln Asp Glu Phe Lys Arg Leu Ala Glu Asn Ser Ala Ser Ser Asp Asp
            20                  25                  30

Leu Leu Val Ala Glu Val Gly Ile Ser Asp Tyr Gly Asp Lys Leu Asn
        35                  40                  45

Met Glu Leu Ser Glu Lys Tyr Lys Leu Asp Lys Glu Ser Tyr Pro Val
    50                  55                  60

Phe Tyr Leu Phe Arg Asp Gly Asp Phe Glu Asn Pro Val Pro Tyr Ser
65                  70                  75                  80

Gly Ala Val Lys Val Gly Ala Ile Gln Arg Trp Leu Lys Gly Gln Gly
                85                  90                  95

Val Tyr Leu Gly Met
            100

<210> SEQ ID NO 191
<211> LENGTH: 105
<212> TYPE: PRT
<213> ORGANISM: Homo sapiens

<400> SEQUENCE: 191

Asp Arg Val Val Ile Arg Phe Gly His Asp Trp Asp Pro Thr Cys
1               5                   10                  15

Met Lys Met Asp Glu Val Leu Tyr Ser Ile Ala Glu Lys Val Lys Asn
            20                  25                  30

Phe Ala Val Ile Tyr Leu Val Asp Ile Thr Glu Val Pro Asp Phe Asn
        35                  40                  45

Lys Met Tyr Glu Leu Tyr Asp Pro Cys Thr Val Met Phe Phe Phe Arg
    50                  55                  60

```
Asn Lys His Ile Met Ile Asp Leu Gly Thr Gly Asn Asn Lys Ile
 65                  70                  75                  80

Asn Trp Ala Met Glu Asp Lys Gln Glu Met Val Asp Ile Ile Glu Thr
                 85                  90                  95

Val Tyr Arg Gly Ala Arg Lys Gly Arg
            100                 105
```

<210> SEQ ID NO 192
<211> LENGTH: 94
<212> TYPE: PRT
<213> ORGANISM: Homo sapiens

<400> SEQUENCE: 192

```
Ala Glu Phe Lys His Val Phe Val Cys Val Gln Asp Arg Pro Pro Gly
 1               5                  10                  15

His Pro Gln Gly Ser Cys Ala Gln Arg Gly Ser Arg Glu Val Phe Gln
                20                  25                  30

Ala Phe Met Glu Lys Ile Gln Thr Asp Pro Gln Leu Phe Met Thr Thr
             35                  40                  45

Val Ile Thr Pro Thr Gly Cys Met Asn Ala Cys Met Met Gly Pro Val
 50                  55                  60

Val Val Val Tyr Pro Asp Gly Val Trp Tyr Gly Gln Val Lys Pro Glu
 65                  70                  75                  80

Asp Val Asp Glu Ile Val Glu Lys His Leu Lys Gly Gly Glu
                85                  90
```

<210> SEQ ID NO 193
<211> LENGTH: 91
<212> TYPE: PRT
<213> ORGANISM: Homo sapiens

<400> SEQUENCE: 193

```
Ile Val Gln Met Arg Gly Glu Val Leu Leu Ala Gly Val Pro Arg His
 1               5                  10                  15

Val Ala Glu Arg Glu Ile Ala Thr Leu Ala Gly Ser Phe Ser Leu His
                20                  25                  30

Glu Gln Asn Ile His Asn Leu Pro Arg Asp Gln Gly Pro Gly Asn Thr
             35                  40                  45

Val Ser Leu Glu Val Ser Glu Asn Ile Thr Glu Arg Phe Phe Val
 50                  55                  60

Val Gly Glu Lys Arg Val Ser Ala Glu Val Val Ala Ala Gln Leu Val
 65                  70                  75                  80

Lys Glu Val Lys Arg Tyr Leu Ala Ser Thr Ala
                85                  90
```

<210> SEQ ID NO 194
<211> LENGTH: 76
<212> TYPE: PRT
<213> ORGANISM: Saccharomyces cerevisiae

<400> SEQUENCE: 194

```
Ser Gly Lys Tyr Thr Leu Gly Tyr Lys Ser Thr Val Lys Ser Leu Arg
 1               5                  10                  15

Gln Gly Lys Ser Lys Leu Ile Ile Ile Ala Ala Asn Thr Pro Val Leu
                20                  25                  30

Arg Lys Ser Glu Leu Glu Tyr Tyr Ala Met Leu Ser Lys Thr Lys Val
             35                  40                  45
```

Tyr Tyr Phe Gln Gly Gly Asn Asn Glu Leu Gly Thr Ala Val Gly Lys
50                  55                  60

Leu Phe Arg Val Gly Val Val Ser Ile Leu Glu Ala
65                  70                  75

<210> SEQ ID NO 195
<211> LENGTH: 76
<212> TYPE: PRT
<213> ORGANISM: Homo sapiens

<400> SEQUENCE: 195

Thr Gly Lys Ile Val Met Gly Ala Arg Lys Ser Ile Gln Tyr Ala Lys
1               5                   10                  15

Met Gly Gly Ala Lys Leu Ile Ile Val Ala Arg Asn Ala Arg Pro Asp
                20                  25                  30

Ile Lys Glu Asp Ile Glu Tyr Tyr Ala Arg Leu Ser Gly Ile Pro Val
            35                  40                  45

Tyr Glu Phe Glu Gly Thr Ser Val Glu Leu Gly Thr Leu Leu Gly Arg
50                  55                  60

Pro His Thr Val Ser Ala Leu Ala Val Val Asp Pro
65                  70                  75

<210> SEQ ID NO 196
<211> LENGTH: 76
<212> TYPE: PRT
<213> ORGANISM: Homo sapiens

<400> SEQUENCE: 196

Thr Gly Ala Val Lys Lys Gly Thr Asn Glu Thr Thr Lys Ser Ile Glu
1               5                   10                  15

Arg Gly Ser Ala Glu Leu Val Phe Val Ala Glu Asp Val Gln Pro Glu
                20                  25                  30

Glu Ile Val Met His Ile Pro Glu Leu Ala Asp Glu Lys Gly Val Pro
            35                  40                  45

Phe Ile Phe Val Glu Gln Gln Asp Asp Leu Gly His Ala Ala Gly Leu
50                  55                  60

Glu Val Gly Ser Ala Ala Ala Val Thr Asp Ala
65                  70                  75

<210> SEQ ID NO 197
<211> LENGTH: 76
<212> TYPE: PRT
<213> ORGANISM: Homo sapiens

<400> SEQUENCE: 197

Tyr Lys Gln Leu Arg Lys Gly Ala Asn Glu Ala Thr Lys Thr Leu Asn
1               5                   10                  15

Arg Gly Ile Ser Glu Phe Ile Val Met Ala Ala Asp Ala Glu Pro Leu
                20                  25                  30

Glu Ile Ile Leu His Leu Pro Leu Leu Cys Glu Asp Lys Asn Val Pro
            35                  40                  45

Tyr Val Phe Val Arg Ser Lys Gln Ala Leu Gly Arg Ala Cys Gly Val
50                  55                  60

Ser Arg Pro Val Ile Ala Cys Ser Val Thr Ile Lys
65                  70                  75

<210> SEQ ID NO 198
<211> LENGTH: 75
<212> TYPE: PRT

```
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 198

Ser Glu Xaa Ile Tyr Gly Ile His Ala Val Gln Ala Leu Leu Glu Arg
1               5                  10                  15

Ala Pro Glu Arg Phe Gln Glu Val Phe Ile Leu Lys Gly Arg Glu Asp
            20                  25                  30

Lys Arg Leu Leu Pro Leu Ile His Ala Leu Glu Ser Gln Gly Val Val
        35                  40                  45

Ile Gln Leu Ala Asn Arg Gln Tyr Leu Asp Glu Lys Ser Asp Gly Ala
    50                  55                  60

Val His Gln Gly Ile Ile Ala Arg Val Lys Pro
65                  70                  75

<210> SEQ ID NO 199
<211> LENGTH: 76
<212> TYPE: PRT
<213> ORGANISM: Homo sapiens

<400> SEQUENCE: 199

Arg Arg Phe Leu Ile Glu Gly Ala Arg Glu Ile Glu Arg Ala Leu Gln
1               5                  10                  15

Ala Gly Ile Glu Leu Glu Gln Ala Leu Val Trp Gly Gly Leu Asn
            20                  25                  30

Pro Glu Gln Gln Val Tyr Ala Leu Gly Arg Val Gly Arg Leu
        35                  40                  45

Ala Leu Leu Glu Val Ser Glu Ala Val Leu Lys Lys Leu Ser Val Arg
    50                  55                  60

Asp Asn Pro Ala Gly Leu Ile Ala Leu Ala Arg Met
65                  70                  75

<210> SEQ ID NO 200
<211> LENGTH: 117
<212> TYPE: PRT
<213> ORGANISM: Homo sapiens

<400> SEQUENCE: 200

Gly Lys Tyr Cys Phe Gly Val Glu Asp Thr Leu Lys Ala Leu Glu Met
1               5                  10                  15

Gly Ala Val Glu Ile Leu Ile Val Tyr Glu Asn Leu Asp Ile Met Arg
            20                  25                  30

Tyr Val Leu His Cys Gln Gly Thr Glu Glu Lys Ile Leu Tyr Leu
        35                  40                  45

Thr Pro Glu Gln Glu Lys Asp Lys Ser His Phe Thr Asp Lys Glu Thr
    50                  55                  60

Gly Gln Glu His Glu Leu Ile Glu Ser Met Pro Leu Leu Glu Trp Phe
65                  70                  75                  80

Ala Asn Asn Tyr Lys Lys Phe Gly Ala Thr Leu Glu Ile Val Thr Asp
                85                  90                  95

Lys Ser Gln Glu Gly Ser Gln Phe Val Lys Gly Phe Gly Ile Gly
                100                 105                 110

Gly Ile Leu Arg Tyr
            115
```

<210> SEQ ID NO 201
<211> LENGTH: 108
<212> TYPE: PRT
<213> ORGANISM: Homo sapiens

<400> SEQUENCE: 201

Thr Gly Asp Ala Leu Ser Gln Ala Ala Ile Ala Ala Asn Arg Ser
1               5                   10                  15

His Met Pro Tyr Ser Lys Ser Pro Ser Gly Val Ala Leu Glu Cys Lys
            20                  25                  30

Asp Gly Arg Ile Phe Ser Gly Ser Tyr Ala Glu Asn Ala Ala Phe Asn
        35                  40                  45

Pro Thr Leu Pro Pro Leu Gln Gly Ala Leu Ile Leu Leu Asn Leu Lys
    50                  55                  60

Gly Tyr Asp Tyr Pro Asp Ile Gln Arg Ala Val Leu Ala Glu Lys Ala
65                  70                  75                  80

Asp Ala Pro Leu Ile Gln Trp Asp Ala Thr Ser Ala Thr Leu Lys Ala
                85                  90                  95

Leu Gly Cys His Ser Ile Asp Arg Val Leu Leu Ala
            100                 105

<210> SEQ ID NO 202
<211> LENGTH: 103
<212> TYPE: PRT
<213> ORGANISM: Escherichia coli

<400> SEQUENCE: 202

Asp Glu Asp Ala Leu Ala Phe Ala Leu Leu Pro Leu Ala Ala Ala Cys
1               5                   10                  15

Ala Arg Thr Pro Leu Ser Asn Phe Asn Val Gly Ala Ile Ala Arg Gly
            20                  25                  30

Val Ser Gly Thr Trp Tyr Phe Gly Ala Asn Met Glu Phe Ile Gly Ala
        35                  40                  45

Thr Met Gln Gln Thr Val His Ala Glu Gln Ser Ala Ile Ser His Ala
    50                  55                  60

Trp Leu Ser Gly Glu Lys Ala Leu Ala Ala Ile Thr Val Asn Tyr Thr
65                  70                  75                  80

Pro Cys Gly His Cys Arg Gln Phe Met Asn Glu Leu Asn Ser Gly Leu
                85                  90                  95

Asp Leu Arg Ile His Leu Pro
            100

<210> SEQ ID NO 203
<211> LENGTH: 110
<212> TYPE: PRT
<213> ORGANISM: Homo sapiens

<400> SEQUENCE: 203

Met Asn Arg Gln Glu Leu Ile Thr Glu Ala Leu Lys Ala Arg Asp Met
1               5                   10                  15

Ala Tyr Ala Pro Tyr Ser Lys Phe Gln Val Gly Ala Ala Leu Leu Thr
            20                  25                  30

Lys Asp Gly Lys Val Tyr Arg Gly Cys Asn Ile Glu Asn Ala Ala Tyr
        35                  40                  45

Ser Met Cys Asn Cys Ala Glu Arg Thr Ala Leu Phe Lys Ala Val Ser
    50                  55                  60

Glu Gly Asp Thr Glu Phe Gln Met Leu Ala Val Ala Ala Asp Thr Pro
65                  70                  75                  80

-continued

Gly Pro Val Ser Pro Cys Gly Ala Cys Arg Gln Val Ile Ser Glu Leu
                85                  90                  95

Cys Thr Lys Asp Val Ile Val Val Leu Thr Asn Leu Gln Gly
            100                 105                 110

<210> SEQ ID NO 204
<211> LENGTH: 125
<212> TYPE: PRT
<213> ORGANISM: Homo sapiens

<400> SEQUENCE: 204

Ser Lys Trp Asp Gln Lys Gly Met Asp Ile Ala Tyr Glu Glu Ala Ala
1               5                   10                  15

Leu Gly Tyr Lys Glu Gly Gly Val Pro Ile Gly Gly Cys Leu Ile Asn
            20                  25                  30

Asn Lys Asp Gly Ser Val Leu Gly Arg Gly His Asn Met Arg Phe Gln
        35                  40                  45

Lys Gly Ser Ala Thr Leu His Gly Glu Ile Ser Thr Leu Glu Asn Cys
    50                  55                  60

Gly Arg Leu Glu Gly Lys Val Tyr Lys Asp Thr Thr Leu Tyr Thr Thr
65                  70                  75                  80

Leu Ser Pro Cys Asp Met Cys Thr Gly Ala Ile Ile Met Tyr Gly Ile
                85                  90                  95

Pro Arg Cys Val Val Gly Glu Asn Val Asn Phe Lys Ser Lys Gly Glu
            100                 105                 110

Lys Tyr Leu Gln Thr Arg Gly His Glu Val Val Val
        115                 120                 125

<210> SEQ ID NO 205
<211> LENGTH: 106
<212> TYPE: PRT
<213> ORGANISM: Homo sapiens

<400> SEQUENCE: 205

Phe Met Pro Gly Phe Ala Pro Leu Thr Ser Arg Gly Ser Gln Gln Tyr
1               5                   10                  15

Arg Ala Leu Thr Val Pro Glu Leu Thr Gln Gln Met Phe Asp Ala Lys
            20                  25                  30

Asn Met Met Ala Ala Cys Asp Pro Arg His Gly Arg Tyr Leu Thr Val
        35                  40                  45

Ala Ala Val Phe Arg Gly Arg Met Ser Met Lys Glu Val Asp Glu Gln
    50                  55                  60

Met Leu Asn Val Gln Asn Lys Asn Ser Ser Tyr Phe Val Glu Trp Ile
65                  70                  75                  80

Pro Asn Asn Val Lys Thr Ala Val Cys Asp Ile Pro Pro Arg Gly Leu
                85                  90                  95

Lys Met Ser Ala Thr Phe Ile Gly Asn Ser
            100                 105

<210> SEQ ID NO 206
<211> LENGTH: 114
<212> TYPE: PRT
<213> ORGANISM: Homo sapiens

<400> SEQUENCE: 206

Pro Leu Ala Thr Tyr Ala Pro Val Ile Ser Ala Glu Lys Ala Tyr His
1               5                   10                  15

Glu Gln Leu Ser Val Ala Glu Ile Thr Asn Ala Cys Phe Glu Pro Ala
                20                  25                  30

Asn Gln Met Val Lys Cys Asp Pro Arg His Gly Lys Tyr Met Ala Cys
            35                  40                  45

Cys Leu Leu Tyr Arg Gly Asp Val Val Pro Lys Asp Val Asn Ala Ala
        50                  55                  60

Ile Ala Thr Ile Lys Thr Lys Arg Thr Ile Gln Phe Val Asp Trp Cys
65                  70                  75                  80

Pro Thr Gly Phe Lys Val Gly Ile Asn Tyr Glu Pro Pro Thr Val Val
                85                  90                  95

Pro Gly Gly Asp Leu Ala Lys Val Gln Arg Ala Val Cys Met Leu Ser
                100                 105                 110

Asn Thr

<210> SEQ ID NO 207
<211> LENGTH: 91
<212> TYPE: PRT
<213> ORGANISM: Homo sapiens

<400> SEQUENCE: 207

Ala Met Ile Gly Ile Gly Glu Ser Asp Ser Lys Arg Ala Lys Glu
1               5                   10                  15

Ala Val Ser Met Ala Leu Asn Ser Pro Leu Asp Val Asp Ile Asp
                20                  25                  30

Gly Ala Thr Gly Ala Leu Ile His Val Met Gly Pro Glu Asp Leu Thr
            35                  40                  45

Leu Glu Glu Ala Arg Glu Val Val Ala Thr Val Ser Ser Arg Leu Asp
        50                  55                  60

Pro Asn Ala Thr Ile Ile Trp Gly Ala Thr Ile Asp Glu Asn Leu Glu
65                  70                  75                  80

Asn Thr Val Arg Val Leu Leu Val Ile Thr Gly
                85                  90

<210> SEQ ID NO 208
<211> LENGTH: 92
<212> TYPE: PRT
<213> ORGANISM: Homo sapiens

<400> SEQUENCE: 208

Ala Met Met Gly Thr Gly Cys Ala Ser Gly Pro Asn Arg Ala Arg Glu
1               5                   10                  15

Ala Thr Glu Ala Ala Ile Arg Asn Pro Leu Leu Glu Asp Val Asn Leu
                20                  25                  30

Gln Gly Ala Arg Gly Ile Leu Val Asn Ile Thr Ala Gly Pro Asp Leu
            35                  40                  45

Ser Leu Gly Glu Tyr Ser Asp Val Gly Asn Ile Ile Glu Gln Phe Ala
        50                  55                  60

Ser Glu His Ala Thr Val Lys Val Gly Thr Val Ile Asp Ala Asp Met
65                  70                  75                  80

Arg Asp Glu Leu His Val Thr Val Val Ala Thr Gly
                85                  90

<210> SEQ ID NO 209
<211> LENGTH: 151
<212> TYPE: PRT
<213> ORGANISM: Homo sapiens

<400> SEQUENCE: 209

```
Gly His Ser Ile Gly Ile Ala Leu Gly Ala Cys Thr Val Pro Ala Ala
1               5                   10                  15

Gly Lys Pro Ser Phe Thr Leu Ala Asp Asn Glu Met Glu Phe Gly Val
            20                  25                  30

Gly Ile His Gly Glu Pro Gly Ile Asp Arg Arg Pro Phe Ser Ser Leu
            35                  40                  45

Asp Gln Thr Val Asp Glu Met Phe Asp Thr Leu Leu Val Asn Gly Ser
        50                  55                  60

Tyr His Arg Thr Leu Arg Phe Trp Asp Tyr Gln Gln Gly Ser Trp Gln
65                  70                  75                  80

Glu Glu Gln Gln Thr Lys Gln Pro Leu Gln Ser Gly Asp Arg Val Ile
                85                  90                  95

Ala Leu Val Asn Asn Leu Gly Ala Thr Pro Leu Ser Glu Leu Tyr Gly
                100                 105                 110

Val Tyr Asn Arg Leu Thr Thr Arg Cys Gln Gln Ala Gly Leu Thr Ile
                115                 120                 125

Glu Arg Asn Leu Ile Gly Ala Tyr Cys Thr Ser Leu Asp Met Thr Gly
            130                 135                 140

Phe Ser Ile Thr Leu Leu Lys
145                 150

<210> SEQ ID NO 210
<211> LENGTH: 92
<212> TYPE: PRT
<213> ORGANISM: Homo sapiens

<400> SEQUENCE: 210

Arg Gly Ile Arg Gly Ala Thr Thr Val Glu Arg Asp Thr Glu Glu Glu
1               5                   10                  15

Ile Leu Gln Lys Thr Lys Gln Leu Leu Glu Lys Ile Ile Glu Glu Asn
            20                  25                  30

His Thr Lys Pro Glu Asp Val Val Gln Met Leu Leu Ser Ala Thr Pro
        35                  40                  45

Asp Leu His Ala Val Phe Pro Ala Lys Ala Val Arg Glu Leu Ser Gly
    50                  55                  60

Trp Gln Tyr Val Pro Val Thr Cys Met Gln Glu Met Asp Val Thr Gly
65                  70                  75                  80

Gly Leu Lys Lys Cys Ile Arg Val Met Met Thr Val
                85                  90

<210> SEQ ID NO 211
<211> LENGTH: 92
<212> TYPE: PRT
<213> ORGANISM: Homo sapiens

<400> SEQUENCE: 211

Arg Gly Ile Arg Gly Ala Ile Thr Val Glu Glu Asp Thr Pro Glu Ala
1               5                   10                  15

Ile His Gln Ala Thr Arg Glu Leu Leu Leu Lys Met Leu Glu Ala Asn
            20                  25                  30

Gly Ile Gln Ser Tyr Glu Glu Leu Ala Ala Val Ile Phe Thr Val Thr
        35                  40                  45

Glu Asp Leu Thr Ser Ala Phe Pro Ala Glu Ala Arg Gln Ile Gly
    50                  55                  60

Met His Arg Val Pro Leu Leu Ser Ala Arg Glu Val Pro Val Pro Gly
65                  70                  75                  80
```

```
Ser Leu Pro Arg Val Ile Arg Val Leu Ala Leu Trp
            85                  90
```

<210> SEQ ID NO 212
<211> LENGTH: 95
<212> TYPE: PRT
<213> ORGANISM: Homo sapiens

<400> SEQUENCE: 212

```
Tyr Ser Ser Gly Gln Ile Pro Leu Thr Pro Ser Gly Glu Met Val Asn
1               5                   10                  15

Gly Asp Ile Lys Glu Gln Thr His Gln Val Phe Ser Asn Leu Lys Ala
            20                  25                  30

Val Leu Glu Glu Ala Gly Ala Ser Phe Glu Thr Val Val Lys Ala Thr
        35                  40                  45

Val Phe Ile Ala Asp Met Glu Gln Phe Ala Glu Val Asn Glu Val Tyr
    50                  55                  60

Gly Gln Tyr Phe Asp Thr His Lys Pro Ala Arg Ser Cys Val Glu Val
65                  70                  75                  80

Ala Arg Leu Pro Lys Asp Ala Leu Val Glu Ile Glu Val Ile Ala
                85                  90                  95
```

<210> SEQ ID NO 213
<211> LENGTH: 96
<212> TYPE: PRT
<213> ORGANISM: Homo sapiens

<400> SEQUENCE: 213

```
Tyr Ile Ser Gly Gln Ile Gly Met Asp Pro Ser Ser Gly Gln Leu Val
1               5                   10                  15

Ser Gly Gly Val Ala Glu Glu Ala Lys Gln Ala Leu Lys Asn Met Gly
            20                  25                  30

Glu Ile Leu Lys Ala Ala Gly Cys Asp Phe Thr Asn Val Val Lys Thr
        35                  40                  45

Thr Val Leu Leu Ala Asp Ile Asn Asp Phe Asn Thr Val Asn Glu Ile
    50                  55                  60

Tyr Lys Gln Tyr Phe Lys Ser Asn Phe Pro Ala Arg Ala Ala Tyr Gln
65                  70                  75                  80

Val Ala Ala Leu Pro Lys Gly Ser Arg Ile Glu Ile Glu Ala Val Ala
                85                  90                  95
```

<210> SEQ ID NO 214
<211> LENGTH: 98
<212> TYPE: PRT
<213> ORGANISM: Homo sapiens
<220> FEATURE:
<221> NAME/KEY: misc_feature
<222> LOCATION: (80)..(80)
<223> OTHER INFORMATION: Xaa can be any naturally occurring amino acid

<400> SEQUENCE: 214

```
Ile Thr Ser Gly Gln Ile Pro Val Asn Pro Lys Thr Gly Glu Val Pro
1               5                   10                  15

Ala Asp Val Ala Ala Gln Ala Arg Gln Ser Leu Asp Asn Val Lys Ala
            20                  25                  30

Ile Val Glu Ala Ala Gly Leu Lys Val Gly Asp Ile Val Lys Thr Thr
        35                  40                  45

Val Phe Val Lys Asp Leu Asn Asp Phe Ala Thr Val Asn Ala Thr Tyr
    50                  55                  60
```

```
Glu Ala Phe Phe Thr Glu His Asn Ala Thr Phe Pro Ala Arg Ser Xaa
 65                  70                  75                  80

Val Glu Val Ala Arg Leu Pro Lys Asp Val Lys Ile Glu Ile Glu Ala
                 85                  90                  95

Ile Ala

<210> SEQ ID NO 215
<211> LENGTH: 153
<212> TYPE: PRT
<213> ORGANISM: Homo sapiens
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid

<400> SEQUENCE: 215

Arg Ile Gly His Gly Phe Asp Val His Ala Phe Gly Gly Glu Gly Pro
 1               5                  10                  15

Ile Ile Ile Gly Gly Val Arg Ile Pro Tyr Glu Lys Gly Leu Leu Ala
                 20                  25                  30

His Ser Asp Gly Asp Val Ala Leu His Ala Leu Thr Asp Ala Leu Leu
             35                  40                  45

Gly Ala Ala Leu Gly Asp Ile Gly Lys Leu Phe Pro Asp Thr Asp
 50                  55                  60

Pro Ala Phe Lys Gly Ala Asp Ser Arg Glu Leu Leu Arg Glu Ala Trp
 65                  70                  75                  80

Arg Arg Ile Gln Ala Lys Gly Tyr Thr Leu Gly Asn Val Asp Val Thr
                 85                  90                  95

Ile Ile Ala Gln Ala Pro Lys Xaa Leu Pro His Ile Pro Gln Xaa Arg
            100                 105                 110

Val Phe Ile Ala Glu Asp Leu Gly Cys His Xaa Asp Asp Val Asn Val
            115                 120                 125

Lys Ala Thr Thr Thr Glu Lys Leu Gly Phe Thr Gly Arg Gly Glu Gly
        130                 135                 140

Ile Ala Cys Glu Ala Val Ala Leu Leu
145                 150

<210> SEQ ID NO 216
<211> LENGTH: 149
<212> TYPE: PRT
<213> ORGANISM: Homo sapiens

<400> SEQUENCE: 216

Arg Ile Gly Tyr Gly Glu Asp Ser His Arg Leu Glu Glu Gly Arg Pro
 1               5                  10                  15

Leu Tyr Leu Cys Gly Leu Leu Ile Pro Ser Pro Val Gly Ala Leu Ala
                 20                  25                  30

His Ser Asp Gly Asp Ala Ala Leu His Ala Leu Thr Asp Ala Leu Leu
             35                  40                  45

Ser Ala Tyr Gly Leu Gly Asp Ile Gly Leu Leu Phe Pro Asp Thr Asp
 50                  55                  60
```

```
Pro Arg Trp Arg Gly Glu Arg Ser Glu Val Phe Leu Arg Glu Ala Leu
 65                  70                  75                  80

Arg Leu Val Glu Ala Arg Gly Ala Lys Leu Leu Gln Ala Ser Leu Val
                 85                  90                  95

Leu Thr Leu Asp Arg Pro Lys Leu Gly Pro His Arg Lys Ala Leu Val
            100                 105                 110

Asp Ser Leu Ser Arg Leu Leu Arg Leu Pro Gln Asp Arg Ile Gly Leu
        115                 120                 125

Thr Phe Lys Thr Ser Glu Gly Leu Ala Pro Ser His Val Gln Ala Arg
    130                 135                 140

Ala Val Val Leu Leu
145

<210> SEQ ID NO 217
<211> LENGTH: 102
<212> TYPE: PRT
<213> ORGANISM: Homo sapiens

<400> SEQUENCE: 217

Val Ser Gly Thr Asp Gly Val Gly Thr Lys Leu Arg Leu Ala Met Asp
  1               5                  10                  15

Leu Lys Arg His Asp Thr Ile Gly Ile Asp Leu Val Ala Met Cys Val
                 20                  25                  30

Asn Asp Leu Val Val Gln Gly Ala Glu Pro Leu Phe Phe Leu Asp Tyr
            35                  40                  45

Tyr Ala Thr Gly Lys Leu Asp Val Asp Thr Ala Ser Ala Val Ile Ser
    50                  55                  60

Gly Ile Ala Glu Gly Cys Leu Gln Ser Gly Cys Ser Leu Val Gly Gly
 65                  70                  75                  80

Glu Thr Ala Glu Met Pro Gly Met Tyr His Gly Glu Asp Tyr Asp Val
                 85                  90                  95

Ala Gly Phe Cys Val Gly
            100

<210> SEQ ID NO 218
<211> LENGTH: 129
<212> TYPE: PRT
<213> ORGANISM: bacteriophage HK97

<400> SEQUENCE: 218

Asp Thr Arg Ala Asp Ile Ile Ala His Ala Ile Tyr Gln Val Thr Glu
  1               5                  10                  15

Ser Glu Phe Ser Ala Ser Gly Ile Val Leu Asn Pro Arg Asp Trp His
                 20                  25                  30

Asn Ile Ala Leu Leu Lys Asp Asn Glu Gly Arg Tyr Ile Phe Gly Gly
            35                  40                  45

Pro Gln Ala Phe Thr Ser Asn Ile Met Trp Gly Leu Pro Val Val Pro
    50                  55                  60

Thr Lys Ala Gln Ala Ala Gly Thr Phe Thr Val Gly Gly Phe Asp Met
 65                  70                  75                  80

Ala Ser Gln Val Trp Asp Arg Met Asp Ala Thr Val Glu Val Ser Arg
                 85                  90                  95

Glu Asp Arg Asp Asn Phe Val Lys Asn Met Leu Thr Ile Leu Cys Glu
            100                 105                 110

Glu Arg Leu Ala Leu Ala His Tyr Arg Pro Thr Ala Ile Ile Lys Gly
        115                 120                 125
```

Thr

<210> SEQ ID NO 219
<211> LENGTH: 105
<212> TYPE: PRT
<213> ORGANISM: Homo sapiens

<400> SEQUENCE: 219

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Asp Ala Gln Asp
    50                  55                  60

Val Ala Ser Glu Ala Glu Val Lys Ala Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 220
<211> LENGTH: 116
<212> TYPE: PRT
<213> ORGANISM: artificial
<220> FEATURE:
<223> OTHER INFORMATION: mutated human thioredoxin sequence

<400> SEQUENCE: 220

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Ser
            20                  25                  30

Gly Pro Ser Lys Met Ile Lys Pro Phe Phe His Ser Leu Ser Glu Lys
        35                  40                  45

Tyr Ser Asn Val Ile Phe Leu Glu Val Asp Val Asp Asp Ala Gln Asp
    50                  55                  60

Val Ala Ser Glu Ala Glu Val Lys Ala Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val Ala Ala Leu Glu His His
            100                 105                 110

His His His His
        115

<210> SEQ ID NO 221
<211> LENGTH: 484
<212> TYPE: PRT
<213> ORGANISM: artificial
<220> FEATURE:
<223> OTHER INFORMATION: fusion protein containing the extracellular
      domain of CD5

<400> SEQUENCE: 221

Met Pro Met Gly Ser Leu Gln Pro Leu Ala Thr Leu Tyr Leu Leu Gly
1               5                   10                  15

```
Met Leu Val Ala Ser Cys Leu Gly Arg Leu Ser Trp Tyr Asp Pro Asp
            20                  25                  30

Phe Gln Ala Arg Leu Thr Arg Ser Asn Ser Lys Cys Gln Gly Gln Leu
        35                  40                  45

Glu Val Tyr Leu Lys Asp Gly Trp His Met Val Cys Ser Gln Ser Trp
    50                  55                  60

Gly Arg Ser Ser Lys Gln Trp Glu Asp Pro Ser Gln Ala Ser Lys Val
 65                  70                  75                  80

Cys Gln Arg Leu Asn Cys Gly Val Pro Leu Ser Leu Gly Pro Phe Leu
                85                  90                  95

Val Thr Tyr Thr Pro Gln Ser Ser Ile Ile Cys Tyr Gly Gln Leu Gly
            100                 105                 110

Ser Phe Ser Asn Cys Ser His Ser Arg Asn Asp Met Cys His Ser Leu
        115                 120                 125

Gly Leu Thr Cys Leu Glu Pro Gln Lys Thr Thr Pro Thr Thr Arg
130                 135                 140

Pro Pro Pro Thr Thr Thr Pro Glu Pro Thr Ala Pro Pro Arg Leu Gln
145                 150                 155                 160

Leu Val Ala Gln Ser Gly Gly Gln His Cys Ala Gly Val Val Glu Phe
                165                 170                 175

Tyr Ser Gly Ser Leu Gly Gly Thr Ile Ser Tyr Glu Ala Gln Asp Lys
            180                 185                 190

Thr Gln Asp Leu Glu Asn Phe Leu Cys Asn Asn Leu Gln Cys Gly Ser
        195                 200                 205

Phe Leu Lys His Leu Pro Glu Thr Glu Ala Gly Arg Ala Gln Asp Pro
210                 215                 220

Gly Glu Pro Arg Glu His Gln Pro Leu Pro Ile Gln Trp Lys Ile Gln
225                 230                 235                 240

Asn Ser Ser Cys Thr Ser Leu Glu His Cys Phe Arg Lys Ile Lys Pro
                245                 250                 255

Gln Lys Ser Gly Arg Val Leu Ala Leu Leu Cys Ser Gly Phe Gln Pro
            260                 265                 270

Lys Val Gln Ser Arg Leu Val Gly Gly Ser Ser Ile Cys Glu Gly Thr
        275                 280                 285

Val Glu Val Arg Gln Gly Ala Gln Trp Ala Ala Leu Cys Asp Ser Ser
290                 295                 300

Ser Ala Arg Ser Ser Leu Arg Trp Glu Glu Val Cys Arg Glu Gln Gln
305                 310                 315                 320

Cys Gly Ser Val Asn Ser Tyr Arg Val Leu Asp Ala Gly Asp Pro Thr
                325                 330                 335

Ser Arg Gly Leu Phe Cys Pro His Gln Lys Leu Ser Gln Cys His Glu
            340                 345                 350

Leu Trp Glu Arg Asn Ser Tyr Cys Lys Lys Val Phe Val Thr Cys Gln
        355                 360                 365

Asp Pro Gly Pro Ser Gly Gly Pro Gly Gly Ser Pro Gly Gly
370                 375                 380

Ser Gly Glu Asn Leu Tyr Phe Gln Ser Gly Ser Gly Gly Pro Gly Ser
385                 390                 395                 400

Gly Glu Asn Leu Tyr Phe Gln Gly Gly Ser Pro Ser Gly Gly Ala
                405                 410                 415

Gly Gly Gly Gly Gly Ser Gly Gly Glu Phe Gly Gly Gly Ser Met Asp
            420                 425                 430

Glu Lys Thr Thr Gly Trp Arg Gly Gly His Val Val Glu Gly Leu Ala
```

```
        435                 440                 445

Gly Glu Leu Glu Gln Leu Arg Ala Arg Leu Glu His His Pro Gln Gly
    450                 455                 460

Gln Arg Glu Pro Gly Thr Gly Gly Gly Ser His His His His His His
465                 470                 475                 480

His His Pro Ala

<210> SEQ ID NO 222
<211> LENGTH: 11
<212> TYPE: PRT
<213> ORGANISM: artificial
<220> FEATURE:
<223> OTHER INFORMATION: TRX-3 insertion site for CD5 binders
<220> FEATURE:
<221> NAME/KEY: MISC_FEATURE
<222> LOCATION: (2)..(10)
<223> OTHER INFORMATION: residues 2 to 10 can be SEQ ID NO:39
<220> FEATURE:
<221> NAME/KEY: MISC_FEATURE
<222> LOCATION: (2)..(10)
<223> OTHER INFORMATION: residues 2 to 10 can be SEQ ID NO:35
<220> FEATURE:
<221> NAME/KEY: MISC_FEATURE
<222> LOCATION: (2)..(10)
<223> OTHER INFORMATION: residues 2 to 10 can be SEQ ID NO:41
<220> FEATURE:
<221> NAME/KEY: MISC_FEATURE
<222> LOCATION: (2)..(10)
<223> OTHER INFORMATION: residues 2 to 10 can be SEQ ID NO:37

<400> SEQUENCE: 222

Thr Xaa Xaa Xaa Xaa Xaa Xaa Xaa Xaa Xaa Trp
1               5                   10

<210> SEQ ID NO 223
<211> LENGTH: 11
<212> TYPE: PRT
<213> ORGANISM: artificial
<220> FEATURE:
<223> OTHER INFORMATION: TRX-3 insertion site for CD5 binders
<220> FEATURE:
<221> NAME/KEY: MISC_FEATURE
<222> LOCATION: (2)..(10)
<223> OTHER INFORMATION: residues 2 to 10 can be SEQ ID NO:40
<220> FEATURE:
<221> NAME/KEY: MISC_FEATURE
<222> LOCATION: (2)..(10)
<223> OTHER INFORMATION: residues 2 to 10 can be SEQ ID NO:36
<220> FEATURE:
<221> NAME/KEY: MISC_FEATURE
<222> LOCATION: (2)..(10)
<223> OTHER INFORMATION: residues 2 to 10 can be SEQ ID NO:42
<220> FEATURE:
<221> NAME/KEY: MISC_FEATURE
<222> LOCATION: (2)..(10)
<223> OTHER INFORMATION: residues 2 to 10 can be SEQ ID NO:38
<220> FEATURE:
<221> NAME/KEY: MISC_FEATURE
<222> LOCATION: (2)..(10)
<223> OTHER INFORMATION: residues 2 to 10 can be SEQ ID NO:224

<400> SEQUENCE: 223

Ala Xaa Xaa Xaa Xaa Xaa Xaa Xaa Xaa Xaa Pro
1               5                   10

<210> SEQ ID NO 224
<211> LENGTH: 5
<212> TYPE: PRT
<213> ORGANISM: Homo sapiens

<400> SEQUENCE: 224
```

```
Val Lys Ala Met Pro
1               5

<210> SEQ ID NO 225
<211> LENGTH: 21
<212> TYPE: PRT
<213> ORGANISM: artificial
<220> FEATURE:
<223> OTHER INFORMATION: schematic of TRX-L1 library
<220> FEATURE:
<221> NAME/KEY: REPEAT
<222> LOCATION: (1)..(4)
<223> OTHER INFORMATION: residues 1 to 4 can be present 1, 2, or 3 times
<220> FEATURE:
<221> NAME/KEY: NON_CONS
<222> LOCATION: (4)..(5)
<223> OTHER INFORMATION: residues 4 to 5 are non-consecutive
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (11)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: NON_CONS
<222> LOCATION: (17)..(18)
<223> OTHER INFORMATION: residues 17 to 18 are non-consecutive
<220> FEATURE:
<221> NAME/KEY: misc_feature
<222> LOCATION: (19)..(21)
<223> OTHER INFORMATION: Xaa can be any naturally occurring amino acid

<400> SEQUENCE: 225

Xaa Xaa Xaa Xaa Xaa Xaa Xaa Xaa Val Ala Xaa Xaa Xaa Xaa Val Xaa
1               5                   10                  15

Xaa Xaa Xaa Xaa Xaa
            20

<210> SEQ ID NO 226
<211> LENGTH: 21
<212> TYPE: PRT
<213> ORGANISM: artificial
<220> FEATURE:
<223> OTHER INFORMATION: schematic of TRX-L2 library
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: NON_CONS
<222> LOCATION: (4)..(4)
<223> OTHER INFORMATION: residues 4 to 5 are non-consecutive
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (11)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: NON_CONS
<222> LOCATION: (17)..(18)
<223> OTHER INFORMATION: residues 17 to 18 are non-consecutive
```

```
<220> FEATURE:
<221> NAME/KEY: misc_feature
<222> LOCATION: (19)..(21)
<223> OTHER INFORMATION: Xaa can be any naturally occurring amino acid

<400> SEQUENCE: 226

Xaa Xaa Xaa Xaa Xaa Xaa Xaa Xaa Val Ala Xaa Xaa Xaa Xaa Val Xaa
1               5                   10                  15

Xaa Xaa Xaa Xaa Xaa
            20

<210> SEQ ID NO 227
<211> LENGTH: 18
<212> TYPE: PRT
<213> ORGANISM: artificial
<220> FEATURE:
<223> OTHER INFORMATION: schematic of TRX-L3 library
<220> FEATURE:
<221> NAME/KEY: REPEAT
<222> LOCATION: (1)..(1)
<223> OTHER INFORMATION: residues 1 can be present 4, 5, 6, or 7 times
<220> FEATURE:
<221> NAME/KEY: NON_CONS
<222> LOCATION: (1)..(2)
<223> OTHER INFORMATION: residues 1 to 2 are non-consecutive
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: NON_CONS
<222> LOCATION: (14)..(15)
<223> OTHER INFORMATION: residues 14 to 15 are non-consecutive
<220> FEATURE:
<221> NAME/KEY: misc_feature
<222> LOCATION: (16)..(18)
<223> OTHER INFORMATION: Xaa can be any naturally occurring amino acid

<400> SEQUENCE: 227

Xaa Xaa Xaa Xaa Xaa Val Ala Xaa Xaa Xaa Xaa Val Xaa Xaa Xaa Xaa
1               5                   10                  15

Xaa Xaa

<210> SEQ ID NO 228
<211> LENGTH: 29
<212> TYPE: PRT
<213> ORGANISM: artificial
<220> FEATURE:
<223> OTHER INFORMATION: loop sequence of binder peptides

<400> SEQUENCE: 228

Ser Tyr Tyr Ser Ser Ser Tyr Ser Ser Tyr Ser Ser Ser Ser Tyr Ser
1               5                   10                  15

Val Ala Ser Ser Ser Tyr Val Tyr Ser Ser Gly Ala Asn
            20                  25

<210> SEQ ID NO 229
<211> LENGTH: 21
<212> TYPE: PRT
<213> ORGANISM: artificial
<220> FEATURE:
<223> OTHER INFORMATION: loop sequence of binder peptides
```

<400> SEQUENCE: 229

Pro Gly Arg Thr Glu Ser Arg Met Val Ala Thr Ala Glu Pro Val Ala
1               5                   10                  15

Leu Ser Gly Asp Lys
            20

<210> SEQ ID NO 230
<211> LENGTH: 21
<212> TYPE: PRT
<213> ORGANISM: artificial
<220> FEATURE:
<223> OTHER INFORMATION: loop sequence of binder peptides

<400> SEQUENCE: 230

Pro Glu Ser His Val Gly Arg His Val Ala Gly Ile Glu Asn Val Gly
1               5                   10                  15

Asn Tyr Gly Ser Lys
            20

<210> SEQ ID NO 231
<211> LENGTH: 21
<212> TYPE: PRT
<213> ORGANISM: artificial
<220> FEATURE:
<223> OTHER INFORMATION: loop sequence of binder peptides

<400> SEQUENCE: 231

Pro Ala Ser Tyr Val Leu Pro Ser Val Ala Gly Glu Asp Arg Val Val
1               5                   10                  15

Gln Tyr Gly Thr Asn
            20

<210> SEQ ID NO 232
<211> LENGTH: 21
<212> TYPE: PRT
<213> ORGANISM: artificial
<220> FEATURE:
<223> OTHER INFORMATION: loop sequence of binder peptides

<400> SEQUENCE: 232

Pro Ala Ser Phe Arg Ser Asp Asn Val Ala Val Gln Thr Gly Val Ala
1               5                   10                  15

Leu Ser Gly Ala Asn
            20

<210> SEQ ID NO 233
<211> LENGTH: 22
<212> TYPE: PRT
<213> ORGANISM: artificial
<220> FEATURE:
<223> OTHER INFORMATION: loop sequence of binder peptides

<400> SEQUENCE: 233

Pro Ala Arg Tyr Gly Glu Pro Leu Tyr Val Ala Lys Asp Gly Glu Val
1               5                   10                  15

Val Leu Ser Gly Ala Asp
            20

<210> SEQ ID NO 234
<211> LENGTH: 22
<212> TYPE: PRT
<213> ORGANISM: artificial
<220> FEATURE:

<223> OTHER INFORMATION: loop sequence of binder peptides

<400> SEQUENCE: 234

Pro Gly Ala Tyr Gly Ala His Arg Ala Val Ala Ser Gly Gly Gln Val
1               5                   10                  15

Val Leu Ser Gly Ala Asn
            20

<210> SEQ ID NO 235
<211> LENGTH: 22
<212> TYPE: PRT
<213> ORGANISM: artificial
<220> FEATURE:
<223> OTHER INFORMATION: loop sequence of binder peptides

<400> SEQUENCE: 235

Pro Gly Arg His Ala Gly Ala Gln Asp Val Ala Tyr Glu Ala Glu Val
1               5                   10                  15

Val Leu Ser Gly Ser Lys
            20

<210> SEQ ID NO 236
<211> LENGTH: 22
<212> TYPE: PRT
<213> ORGANISM: artificial
<220> FEATURE:
<223> OTHER INFORMATION: loop sequence of binder peptides

<400> SEQUENCE: 236

Pro Gly Ser Tyr Ala Tyr Leu Gln Gly Val Ala Pro Glu Met Glu Val
1               5                   10                  15

Val Leu Ser Gly Phe His
            20

<210> SEQ ID NO 237
<211> LENGTH: 22
<212> TYPE: PRT
<213> ORGANISM: artificial
<220> FEATURE:
<223> OTHER INFORMATION: loop sequence of binder peptides

<400> SEQUENCE: 237

Pro Ser Ser Tyr Ala Asp His Ser Asp Val Ala Pro Thr Tyr Glu Val
1               5                   10                  15

Met Leu Ser Gly Ala Asn
            20

<210> SEQ ID NO 238
<211> LENGTH: 22
<212> TYPE: PRT
<213> ORGANISM: artificial
<220> FEATURE:
<223> OTHER INFORMATION: loop sequence of binder peptides

<400> SEQUENCE: 238

Pro Gly Arg Phe Ser Asp Ala Tyr Asp Val Ala Thr Glu Tyr Glu Val
1               5                   10                  15

Met Leu Ser Gly Ala Asn
            20

<210> SEQ ID NO 239
<211> LENGTH: 22
<212> TYPE: PRT
<213> ORGANISM: artificial

```
<220> FEATURE:
<223> OTHER INFORMATION: loop sequence of binder peptides

<400> SEQUENCE: 239

Pro Ala Pro Tyr Ala Asp Ala His Asp Val Ala Thr Glu Pro Ala Val
1               5                   10                  15

Val Leu Ser Gly Val Asn
            20

<210> SEQ ID NO 240
<211> LENGTH: 22
<212> TYPE: PRT
<213> ORGANISM: artificial
<220> FEATURE:
<223> OTHER INFORMATION: loop sequence of binder peptides

<400> SEQUENCE: 240

Pro Gly Pro Tyr Ser Gly Ala Trp Gly Val Ala Ser Glu Ser His Val
1               5                   10                  15

Val Leu Ser Gly Ala Ala
            20

<210> SEQ ID NO 241
<211> LENGTH: 22
<212> TYPE: PRT
<213> ORGANISM: artificial
<220> FEATURE:
<223> OTHER INFORMATION: loop sequence of binder peptides

<400> SEQUENCE: 241

Pro Gly Gln Thr Thr Tyr Ala Gln Asn Val Ala Gly Glu Gly Gly Val
1               5                   10                  15

Val Leu Ser Gly Arg Thr
            20

<210> SEQ ID NO 242
<211> LENGTH: 22
<212> TYPE: PRT
<213> ORGANISM: artificial
<220> FEATURE:
<223> OTHER INFORMATION: loop sequence of binder peptides

<400> SEQUENCE: 242

Pro Lys Pro Tyr Ala Tyr Ala Arg Gly Val Ala Arg Glu Ala Glu Val
1               5                   10                  15

Val Leu Ser Gly Ala Asp
            20

<210> SEQ ID NO 243
<211> LENGTH: 22
<212> TYPE: PRT
<213> ORGANISM: artificial
<220> FEATURE:
<223> OTHER INFORMATION: loop sequence of binder peptides

<400> SEQUENCE: 243

Pro Arg Thr Tyr Gln Gly Gly Ser Gly Val Ala Lys Gly Asp Gln Val
1               5                   10                  15

Val Ile Ser Gly Ala Asp
            20

<210> SEQ ID NO 244
<211> LENGTH: 22
<212> TYPE: PRT
```

```
<213> ORGANISM: artificial
<220> FEATURE:
<223> OTHER INFORMATION: loop sequence of binder peptides

<400> SEQUENCE: 244

Pro Val Thr Val Ala Tyr Gly Gln Ala Val Ala Tyr Glu Thr Glu Val
1               5                   10                  15

Val Arg Ala Gly Pro Tyr
            20

<210> SEQ ID NO 245
<211> LENGTH: 22
<212> TYPE: PRT
<213> ORGANISM: artificial
<220> FEATURE:
<223> OTHER INFORMATION: loop sequence of binder peptides

<400> SEQUENCE: 245

Pro Thr Gln Tyr Lys Glu Ala Arg Asp Val Ala Ser Gln Pro Glu Val
1               5                   10                  15

Val Leu Ser Gly Ala Asp
            20

<210> SEQ ID NO 246
<211> LENGTH: 22
<212> TYPE: PRT
<213> ORGANISM: artificial
<220> FEATURE:
<223> OTHER INFORMATION: loop sequence of binder peptides
<220> FEATURE:
<221> NAME/KEY: misc_feature
<222> LOCATION: (22)..(22)
<223> OTHER INFORMATION: Xaa can be any naturally occurring amino acid

<400> SEQUENCE: 246

Pro Gly Gln Phe His Asp Ala Gln Ala Val Ala Ser Glu Gly Gly Val
1               5                   10                  15

Val Leu Ser Gly Ala Xaa
            20

<210> SEQ ID NO 247
<211> LENGTH: 22
<212> TYPE: PRT
<213> ORGANISM: artificial
<220> FEATURE:
<223> OTHER INFORMATION: loop sequence of binder peptides

<400> SEQUENCE: 247

Pro Arg Thr Tyr Gln Tyr Asn Gln Asp Val Ala Ser Gln Asp Val Val
1               5                   10                  15

Ala Ser Ser Gly Val His
            20

<210> SEQ ID NO 248
<211> LENGTH: 22
<212> TYPE: PRT
<213> ORGANISM: artificial
<220> FEATURE:
<223> OTHER INFORMATION: loop sequence of binder peptides

<400> SEQUENCE: 248

Pro Tyr Ala Tyr Gly Lys Thr Lys Ser Val Ala Ser Glu Glu Glu Val
1               5                   10                  15

Val Leu Ser Gly Gly His
            20
```

<210> SEQ ID NO 249
<211> LENGTH: 23
<212> TYPE: PRT
<213> ORGANISM: artificial
<220> FEATURE:
<223> OTHER INFORMATION: loop sequence of binder peptides

<400> SEQUENCE: 249

Pro Gly Pro Leu Ser Trp Tyr Ala Arg Asp Val Ala Pro Glu Ala Ala
1               5                   10                  15

Val Ala Gln Phe Gly Ala Asn
            20

<210> SEQ ID NO 250
<211> LENGTH: 11
<212> TYPE: PRT
<213> ORGANISM: artificial
<220> FEATURE:
<223> OTHER INFORMATION: TRX-3 insertion site for specific binders to
      various protein targets, including CD3, CD5, CD19, CD22, EpCAM,
      LGR5, and HSA
<220> FEATURE:
<221> NAME/KEY: MISC_FEATURE
<222> LOCATION: (2)..(10)
<223> OTHER INFORMATION: residues 2 to 10 can be SEQ ID NO:45
<220> FEATURE:
<221> NAME/KEY: MISC_FEATURE
<222> LOCATION: (2)..(10)
<223> OTHER INFORMATION: residues 2 to 10 can be SEQ ID NO:39
<220> FEATURE:
<221> NAME/KEY: MISC_FEATURE
<222> LOCATION: (2)..(10)
<223> OTHER INFORMATION: residues 2 to 10 can be SEQ ID NO:53
<220> FEATURE:
<221> NAME/KEY: MISC_FEATURE
<222> LOCATION: (2)..(10)
<223> OTHER INFORMATION: residues 2 to 10 can be SEQ ID NO:56
<220> FEATURE:
<221> NAME/KEY: MISC_FEATURE
<222> LOCATION: (2)..(10)
<223> OTHER INFORMATION: residues 2 to 10 can be SEQ ID NO:62
<220> FEATURE:
<221> NAME/KEY: MISC_FEATURE
<222> LOCATION: (2)..(10)
<223> OTHER INFORMATION: residues 2 to 10 can be SEQ ID NO:111
<220> FEATURE:
<221> NAME/KEY: MISC_FEATURE
<222> LOCATION: (2)..(10)
<223> OTHER INFORMATION: residues 2 to 10 can be SEQ ID NO:119

<400> SEQUENCE: 250

Thr Xaa Xaa Xaa Xaa Xaa Xaa Xaa Xaa Xaa Trp
1               5                   10

<210> SEQ ID NO 251
<211> LENGTH: 11
<212> TYPE: PRT
<213> ORGANISM: artificial
<220> FEATURE:
<223> OTHER INFORMATION: TRX-3 insertion site for specific binders to
      various protein targets, including CD3, CD5, CD19, CD22, EpCAM,
      LGR5, and HSA
<220> FEATURE:
<221> NAME/KEY: MISC_FEATURE
<222> LOCATION: (2)..(10)
<223> OTHER INFORMATION: residues 2 to 10 can be SEQ ID NO:46
<220> FEATURE:
<221> NAME/KEY: MISC_FEATURE
<222> LOCATION: (2)..(10)

```
<223> OTHER INFORMATION: residues 2 to 10 can be SEQ ID NO:40
<220> FEATURE:
<221> NAME/KEY: MISC_FEATURE
<222> LOCATION: (2)..(10)
<223> OTHER INFORMATION: residues 2 to 10 can be SEQ ID NO:54
<220> FEATURE:
<221> NAME/KEY: MISC_FEATURE
<222> LOCATION: (2)..(10)
<223> OTHER INFORMATION: residues 2 to 10 can be SEQ ID NO:57
<220> FEATURE:
<221> NAME/KEY: MISC_FEATURE
<222> LOCATION: (2)..(10)
<223> OTHER INFORMATION: residues 2 to 10 can be SEQ ID NO:63
<220> FEATURE:
<221> NAME/KEY: MISC_FEATURE
<222> LOCATION: (2)..(10)
<223> OTHER INFORMATION: residues 2 to 10 can be SEQ ID NO:112
<220> FEATURE:
<221> NAME/KEY: MISC_FEATURE
<222> LOCATION: (2)..(10)
<223> OTHER INFORMATION: residues 2 to 10 can be SEQ ID NO:120

<400> SEQUENCE: 251

Ala Xaa Xaa Xaa Xaa Xaa Xaa Xaa Xaa Xaa Pro
1               5                   10

<210> SEQ ID NO 252
<211> LENGTH: 6
<212> TYPE: PRT
<213> ORGANISM: artificial
<220> FEATURE:
<223> OTHER INFORMATION: loop sequence of binder peptides

<400> SEQUENCE: 252

Ala Glu Val Lys Ala Met
1               5

<210> SEQ ID NO 253
<211> LENGTH: 8
<212> TYPE: PRT
<213> ORGANISM: artificial
<220> FEATURE:
<223> OTHER INFORMATION: loop sequence of binder peptides

<400> SEQUENCE: 253

Ala Asn Glu Gln Ala Thr Lys Ala
1               5

<210> SEQ ID NO 254
<211> LENGTH: 9
<212> TYPE: PRT
<213> ORGANISM: artificial
<220> FEATURE:
<223> OTHER INFORMATION: loop sequence of binder peptides

<400> SEQUENCE: 254

Phe Cys Phe Phe Cys Phe Pro Thr Phe
1               5
```